United States Patent
Krystek, Jr. et al.

(10) Patent No.: US 10,766,946 B2
(45) Date of Patent: Sep. 8, 2020

(54) FAST-OFF RATE SERUM ALBUMIN BINDING FIBRONECTIN TYPE III DOMAINS

(71) Applicant: BRISTOL-MYERS SQUIBB COMPANY, Princeton, NJ (US)

(72) Inventors: Stanley Richard Krystek, Jr., Ringoes, NJ (US); Tracy S. Mitchell, Andover, MA (US); Michael L. Gosselin, Boston, MA (US); Dasa Lipovsek, Cambridge, MA (US); Juhi Juneja, Lexington, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 95 days.

(21) Appl. No.: 15/760,413

(22) PCT Filed: Sep. 22, 2016

(86) PCT No.: PCT/US2016/053183
§ 371 (c)(1),
(2) Date: Mar. 15, 2018

(87) PCT Pub. No.: WO2017/053617
PCT Pub. Date: Mar. 30, 2017

(65) Prior Publication Data
US 2018/0258158 A1   Sep. 13, 2018

Related U.S. Application Data

(60) Provisional application No. 62/222,508, filed on Sep. 23, 2015.

(51) Int. Cl.
C07K 14/78 (2006.01)
C07K 14/765 (2006.01)
C12N 15/85 (2006.01)

(52) U.S. Cl.
CPC ............ *C07K 14/78* (2013.01); *C07K 14/765* (2013.01); *C12N 15/85* (2013.01); *C07K 2319/30* (2013.01); *C12N 2015/8518* (2013.01)

(58) Field of Classification Search
None
See application file for complete search history.

(56) References Cited

U.S. PATENT DOCUMENTS

| | | | |
|---|---|---|---|
| 5,235,041 A | 8/1993 | Cappello et al. |
| 5,514,581 A | 5/1996 | Ferrari et al. |
| 5,545,620 A | 8/1996 | Wahl et al. |
| 5,641,648 A | 6/1997 | Ferrari et al. |
| 5,770,697 A | 6/1998 | Ferrari et al. |
| 5,792,742 A | 8/1998 | Gold et al. |
| 6,018,030 A | 1/2000 | Ferrari et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,316,412 B1 | 11/2001 | Ginsberg et al. |
| 6,342,219 B1 | 1/2002 | Thorpe et al. |
| 6,383,775 B1 | 5/2002 | Duff et al. |
| 6,462,189 B1 | 10/2002 | Koide |
| 6,518,018 B1 | 2/2003 | Szostak et al. |
| 6,559,126 B2 | 5/2003 | Tournaire et al. |
| 6,660,492 B1 | 12/2003 | Bode et al. |
| 6,818,418 B1 | 11/2004 | Lipovsek et al. |
| 7,115,396 B2 | 10/2006 | Lipovsek et al. |
| 7,556,925 B2 | 7/2009 | Koide et al. |
| 7,598,352 B2 | 10/2009 | Koide |
| 7,847,062 B2 | 12/2010 | Chen et al. |
| 7,858,739 B2 | 12/2010 | Chen et al. |
| 8,067,201 B2 | 11/2011 | Morin et al. |
| 8,221,765 B2 | 7/2012 | Camphausen et al. |
| 8,258,265 B2 | 9/2012 | Koide |
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 8,343,501 B2 | 1/2013 | Emanuel et al. |
| 8,420,098 B2 | 4/2013 | Camphausen et al. |
| 8,470,332 B2 | 6/2013 | Camphausen et al. |
| 8,524,244 B2 | 9/2013 | Camphausen et al. |
| 8,609,613 B2 | 12/2013 | Chen et al. |

(Continued)

FOREIGN PATENT DOCUMENTS

| | | | |
|---|---|---|---|
| CA | 2293632 A1 | 12/1998 |
| DE | 19646372 C1 | 6/1997 |

(Continued)

OTHER PUBLICATIONS

Roberts, Richard W., "Totally in vitro protein selection using mRNA-protein fusions and ribosome display," Current Opinion in Chemical Biology, vol. 3:268-273 (1999).
Rottgen, Peter et al., "A human pancreatic secretory trypsin inhibitor presenting a hypervariable highly constrained epitope via monovalent phagemid display," Gene, vol. 164:243-250 (1995).
Scott, Jamie K. et al., "Searching for Peptide Ligands with an Epitope Library," Science, vol. 249:386-390 (1990).
Shibata, K. et al., "An attempt to substitute the cell binding domain of human fibronectin in lambda phage J protein: Computer design and expression," Biochimie, vol. 75:459-465 (1993).

(Continued)

*Primary Examiner* — James H Alstrum-Acevedo
*Assistant Examiner* — Tara L Martinez
(74) *Attorney, Agent, or Firm* — Nelson Mullins Riley & Scarborough LLP; Jane E. Remillard, Esq.; Christopher L. Frank

(57) ABSTRACT

Provided herein are polypeptides which include tenth fibronectin type III domains ($^{10}$Fn3) that binds to serum albumin. Also provided are fusion molecules comprising a serum albumin binding $^{10}$Fn3 joined to a heterologous protein for use in diagnostic and therapeutic applications.

11 Claims, 11 Drawing Sheets

Specification includes a Sequence Listing.

(56) References Cited

U.S. PATENT DOCUMENTS

| | | |
|---|---|---|
| 8,728,483 B2 | 5/2014 | Camphausen et al. |
| 8,969,289 B2 | 3/2015 | Gosselin et al. |
| 9,017,655 B2 | 4/2015 | Emanuel et al. |
| 9,416,170 B2 | 8/2016 | Davis et al. |
| 9,522,951 B2 | 12/2016 | Davis et al. |
| 9,540,424 B2 | 1/2017 | Gosselin et al. |
| 9,605,039 B2 | 3/2017 | Lipovsek et al. |
| 9,765,132 B2 | 9/2017 | Davis et al. |
| 9,902,762 B2 | 2/2018 | Camphausen et al. |
| 10,221,438 B2 | 3/2019 | Gosselin et al. |
| 2002/0019517 A1 | 2/2002 | Koide |
| 2002/0061307 A1 | 5/2002 | Whitlow et al. |
| 2003/0104520 A1 | 6/2003 | Ellington et al. |
| 2003/0170753 A1 | 9/2003 | Koide |
| 2003/0186385 A1 | 10/2003 | Koide |
| 2005/0255548 A1 | 11/2005 | Lipovsek et al. |
| 2006/0246059 A1 | 11/2006 | Lipovsek et al. |
| 2007/0071675 A1 | 3/2007 | Wu et al. |
| 2007/0082365 A1 | 4/2007 | Lipovsek et al. |
| 2007/0160533 A1 | 7/2007 | Chen et al. |
| 2008/0108798 A1 | 5/2008 | Lipovsek et al. |
| 2008/0193445 A1 | 8/2008 | Goetsch et al. |
| 2008/0220049 A1 | 9/2008 | Chen et al. |
| 2009/0176654 A1 | 7/2009 | Cappuccilli et al. |
| 2010/0144601 A1 | 6/2010 | Jacobs et al. |
| 2010/0152063 A1 | 6/2010 | Cappuccilli et al. |
| 2010/0273216 A1 | 10/2010 | Morin et al. |
| 2010/0298541 A1 | 11/2010 | Wu et al. |
| 2011/0021746 A1 | 1/2011 | Cappuccilli et al. |
| 2011/0038866 A1 | 2/2011 | Hastewell et al. |
| 2011/0123545 A1 | 5/2011 | Marsh et al. |
| 2011/0124527 A1 | 5/2011 | Cappuccilli et al. |
| 2011/0275535 A1 | 11/2011 | Loew |
| 2012/0094909 A1 | 4/2012 | Camphausen et al. |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0210703 A1 | 8/2013 | Camphausen et al. |
| 2013/0310317 A1 | 11/2013 | Camphausen et al. |
| 2014/0038893 A1 | 2/2014 | Camphausen et al. |
| 2014/0094595 A1 | 4/2014 | Lipovsek et al. |
| 2014/0179896 A1 | 6/2014 | Chen et al. |
| 2014/0349929 A1 | 11/2014 | Camphausen et al. |
| 2015/0152147 A1 | 6/2015 | Gosselin et al. |
| 2016/0159883 A1 | 6/2016 | Camphausen et al. |
| 2017/0137494 A1 | 5/2017 | Davis et al. |
| 2017/0145464 A1 | 5/2017 | Gosselin et al. |
| 2017/0174748 A1 | 6/2017 | Mitchell et al. |
| 2017/0183393 A1 | 6/2017 | Lipovsek |
| 2017/0275342 A1 | 9/2017 | Lipovsek et al. |
| 2017/0334958 A1 | 11/2017 | Lipovsek et al. |

FOREIGN PATENT DOCUMENTS

| | | |
|---|---|---|
| EP | 0962527 A1 | 12/1999 |
| EP | 1266025 B1 | 11/2006 |
| EP | 0985039 B1 | 2/2008 |
| EP | 1477561 B1 | 12/2008 |
| EP | 1137941 B1 | 8/2009 |
| EP | 2141243 A2 | 1/2010 |
| EP | 2385067 A1 | 11/2011 |
| EP | 2439212 A1 | 4/2012 |
| EP | 2379718 B1 | 3/2013 |
| WO | 92/02536 A1 | 2/1992 |
| WO | 93/03172 A1 | 2/1993 |
| WO | 95/11922 A1 | 5/1995 |
| WO | 96/22391 A1 | 7/1996 |
| WO | 98/12226 A1 | 3/1998 |
| WO | 98/31700 A1 | 7/1998 |
| WO | 98/056915 A2 | 12/1998 |
| WO | 98/56915 A2 | 12/1998 |
| WO | 99/51773 A1 | 10/1999 |
| WO | 2000/34784 A1 | 6/2000 |
| WO | 2000/34787 A1 | 6/2000 |
| WO | 2001/07657 A1 | 2/2001 |
| WO | 2001/64942 A1 | 9/2001 |
| WO | 2002/04523 A2 | 1/2002 |
| WO | 2002/32925 A2 | 4/2002 |
| WO | 2002/081497 A2 | 10/2002 |
| WO | 2002/088171 A2 | 11/2002 |
| WO | 2003/022858 A2 | 3/2003 |
| WO | 2003/104418 A2 | 12/2003 |
| WO | 2005/056764 A2 | 6/2005 |
| WO | 2006/020258 A2 | 2/2006 |
| WO | 2007/012614 A2 | 2/2007 |
| WO | 2007/044688 A1 | 4/2007 |
| WO | 2007/062188 A2 | 5/2007 |
| WO | 2007/092537 A2 | 8/2007 |
| WO | 2007/096076 A2 | 8/2007 |
| WO | 2007/121894 A2 | 11/2007 |
| WO | 2008/031098 A1 | 3/2008 |
| WO | 2008/048970 A2 | 4/2008 |
| WO | 2008/066752 A2 | 6/2008 |
| WO | 2008/096158 A2 | 8/2008 |
| WO | 2008/097497 A2 | 8/2008 |
| WO | 2008/108986 A2 | 9/2008 |
| WO | 2009/023184 A2 | 2/2009 |
| WO | 2009/025806 A2 | 2/2009 |
| WO | 2009/058379 A2 | 5/2009 |
| WO | 2009/073115 A1 | 6/2009 |
| WO | 2009/083804 A2 | 7/2009 |
| WO | 2009/086116 A2 | 7/2009 |
| WO | 2009/102421 A2 | 8/2009 |
| WO | 2009/133208 A1 | 11/2009 |
| WO | 2009/142773 A2 | 11/2009 |
| WO | 2010/051274 A2 | 5/2010 |
| WO | 2010/051310 A2 | 5/2010 |
| WO | 2010/060095 A1 | 5/2010 |
| WO | 2010/069913 A1 | 6/2010 |
| WO | 2010/093627 A2 | 8/2010 |
| WO | 2010/093771 A1 | 8/2010 |
| WO | 2011/020033 A2 | 2/2011 |
| WO | 2011/035202 A2 | 3/2011 |
| WO | 2011/051333 A1 | 5/2011 |
| WO | 2011/051466 A1 | 5/2011 |
| WO | 2011/092233 A1 | 8/2011 |
| WO | 2011/100700 A2 | 8/2011 |
| WO | 2011/103105 A1 | 8/2011 |
| WO | 2011/130324 A1 | 10/2011 |
| WO | 2011/130328 A1 | 10/2011 |
| WO | 2011/130354 A1 | 10/2011 |
| WO | 2011/137319 A2 | 11/2011 |
| WO | 2011/140086 A2 | 11/2011 |
| WO | 2011/150133 A2 | 12/2011 |
| WO | 2012/016245 A2 | 2/2012 |
| WO | 2012/088006 A1 | 6/2012 |
| WO | 2012/142515 A2 | 10/2012 |
| WO | 2012/158678 A1 | 11/2012 |
| WO | 2012/158739 A1 | 11/2012 |
| WO | 2013/049275 A1 | 4/2013 |
| WO | 2013/067029 A2 | 5/2013 |
| WO | 2014/165093 A2 | 10/2014 |
| WO | 2015/143199 A1 | 9/2015 |
| WO | 2017053617 A1 | 3/2017 |

OTHER PUBLICATIONS

Skolnick, Jeffrey et al., "From genes to protein structure and function: novel applications of computational approaches in the genomic era," TibTech, vol. 18:34-39 (2000).

Sleep D. et al., "Albumin as a versatile platform for drug half-life extension",; Biochimica et Biophysica Acta (BBA) General Subjects, vol. 1830(12):5526-5534 (2013).

Smith, George P. et al., "Phage Display," Chem. Rev., vol. 97:391-410 (1997).

Smith, Temple F. et al., "The challenges of genome sequence annotation of 'The devil is in the details,'" Nature Biotechnology, vol. 15:1222-1223 (1997).

Tang, Lisa et al., "Pharmacokinetic Aspects of Biotechnology Products," Journal of Pharmaceutical Sciences, vol. 93(9):2184-2204 (2004).

(56) References Cited

OTHER PUBLICATIONS

Tokuriki, Nobuhiko et al., "Stability effects of mutations and protein evolvability," Current Opinion in Structural Biology, vol. 19:596-604 (2009).
Tramontano, Anna et al., "The Making of the Minibody: an Engineered beta-Protein for the Display of Conformationally Constrained Peptides," Journal of Molecular Recognition, vol. 7:9-24 (1994).
Trinh, Ryan et al., "Optimization of codon pair use within the (GGGGS)3 linker sequence results in enhanced protein expression," Molecular Immunology, vol. 40:717-722 (2004).
Vuento, Matti et al., "Purification of Fibronectin from Human Plasma by Affinity Chromatography under Non-Denaturing Conditions," Biochem. J., vol. 183:331-337 (1979).
Wang, Cheng-I et al., "Isolation of a High Affinity Inhibitor of Urokinase-type Plasminogen Activator by Phage Display of Ecotin," The Journal of Biological Chemistry, vol. 270(20):12250-12256 (1995).
Watanabe, Takeshi et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, vol. 265:15659-15665 (1990).
Wells, James A., "Additivity of Mutational Effects in Proteins," Biochemistry, vol. 29(37):8509-8517 (1990).
Williams, Alan F. et al., "The Immunoglobulin Superfamily—Domains for Cell Surface Recognition," Ann. Rev. Immunol., vol. 6:381-405 (1988).
Williams, Michael J. et al., "Solution Structures of Modular Proteins by Nuclear Magnetic Resonance," Methods in Enzymology, vol. 245:451-469 (1994).
Wilson, David S. et al., "The use of mRNA display to select high-affinity protein-binding peptides," PNAS, vol. 98(7):3750-3755 (2001).
Written Opinion for Application No. PCT/US01/06414, 5 pages, dated Feb. 7, 2002.
Xu, Lihui et al., "Directed Evolution of High-Affinity Antibody Mimics Using mRNA Display," Chemistry & Biology, vol. 9:933-942 (2002).
Zdanov, Alexander et al., Structure of a single-chain antibody variable domain (Fv) fragment complexed with a carbohydrate antigen at 1.7-A resolution, Proc. Natl. Acad. Sci. USA, vol. 91:6423-6427 (1994).
Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).
Apte, Aaron N. et al., "Anchor-Ligated cDNA Libraries: A Technique for Generating a cDNA Library for the Immediate Cloning of the 5' Ends of mRNAs," BioTechniques, vol. 15(5):890-893 (1993).
Baggio, Rick et al., "Identification of epitope-like consensus motifs using mRNA display," Journal of Molecular Recognition, vol. 15:126-134 (2002).
Baron, Martin et al., "H NMR Assignment and Secondary Structure of the Cell Adhesion Type III Module of Fibronectin," Biochemistry, vol. 31:2068-2073 (1992).
Baron, Martin et al., "Protein modules," TIBS, vol. 16:13-17 (1991).
Batori, Vincent et al., "Exploring the potential of the monobody scaffold: effects of loop elongation on the stability of a fibronectin type III domain," Protein Engineering, vol. 15(12):1015-1020 (2002).
Bianchi, Elisabetta et al., "High Level Expression and Rational Mutagenesis of a Designed Protein, the Minibody," J. Mol. Biol., vol. 236:649-659 (1994).
Boder, Eric T. et al., "Directed evolution of antibody fragments with monovalent femtomolar antigen-binding affinity," PNAS, vol. 97(20):10701-10705 (2000).
Boder, Eric T. et al., "Yeast surface display for screening combinatorial polypeptide libraries," Nature Biotechnology, vol. 15:553-557 (1997).

Bork, P. et al.,"The Immunoglobulin Fold, Structural Classification, Sequence Patterns and Common Core," J. Mol. Biol., vol. 242:309-320 (1994).
Bork, Peer et al., "Go hunting in sequence databases but watch out for the traps," TIG, vol. 12(10):425-427 (1996).
Bork, Peer et al., "Proposed acquisition of an animal protein domain by bacteria," Proc. Natl. Acad. Sci. USA, vol. 89:8990-8994 (1992).
Bork, Peer, "Powers and Pitfalls in Sequence Analysis: The 70% Hurdle," Genome Research, vol. 10:398-400 (2000).
Brenner, Steven E., "Errors in genome annotation," TIG, vol. 15(4):132-133 (1999).
Brock, Kenny V. et al., "Nucleotide sequencing of 5' and 3' termini of bovine viral diarrhea virus by RNA ligation and PCR," Journal of Virological Methods, vol. 38:39-46 (1992).
Bruzik, James P. et al., "Spliced leader RNAs from lower eukaryotes are trans-spliced in mammalian cells," Nature, vol. 360(6405):692-695 (1992).
Caliceti, Paolo et al., "Pharmacokinetic and biodistribution properties of poly(ethylene glycol)-protein conjugates," Advanced Drug Delivery Reviews, vol. 55:1261-1277 (2003).
Campbell, Iain D. et al., "Building proteins with fibronectin type III modules, Fibronectin type III modules are versatile components of many proteins. Recent structures of module pairs show how these modules are joined together," Structure, vol. 2:333-337 (1994).
Choy, E.H.S. et al., "Efficacy of a novel PEGylated humanized anti-TNF fragment (CDP870) in patients with rheumatoid arthritis: a phase II double-blinded, randomized, dose-escalating trial," Rheumatology, vol. 41:1133-1137 (2002).
Clackson, Tim et al., "In vitro selection from protein and peptide libraries," TibTech, vol. 12(5):173-184 (1994).
Clackson, Tim et al., "Making antibody fragments using phage display libraries," Nature, vol. 352:624-628 (1991).
Clarke, Jane et al., "Folding and Stability of a Fibronectin Type III Domain of Human Tenascin," J. Mol. Biol., vol. 270:771-778 (1997).
Connelly, Roberta et al., "Mitogenic properties of a bispecific single-chain Fv-Ig fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).
Cota, Ernesto et al., "Two Proteins with the Same Structure Respond very Differently to Mutation: The Role of Plasticity in Protein Stability," J. Mol. Biol., vol. 302:713-725 (2000).
Cujec, Thomas P. et al., "Selection of v-Abl Tyrosine Kinase Substrate Sequences from Randomized Peptide and Cellular Proteomic Libraries Using mRNA Display," Chemistry & Biology, vol. 9:253-264 (2002).
Devlin, James J. et al., "Random Peptide Libraries: A Source of Specific Protein Binding Molecules," Science, vol. 249:404-406 (1990).
DGENE Search Results, 33 pages (2005).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Doerks, Tobias et al., "Protein annotation: detective work for function prediction," TIG, vol. 14(6):248-250 (1998).
Duan, Jinzhu et al., "Fibronectin Type III Domain Based Monobody with High Avidity," Biochemistry, vol. 46:12656-12664 (2007).
Ely, Kathryn R. et al., "Common molecular scaffold for two unrelated RGD molecules," Protein Engineering, vol. 8(8):823-827 (1995).
Emanuel, Stuart L. et al., "A fibronectin scaffold approach to bispecific inhibitors of epidermal growth factor receptor and insulin-like growth factor-I receptor," MAbs, vol. 3(1):38-48 (2011).
Emanuel, Stuart L. et al., "Adnectins as a platform for multi-specific targeted biologics: A novel bispecific inhibitor of EGFR and IGF-IR

(56) References Cited

OTHER PUBLICATIONS growth factor receptors," Cancer Research, vol. 70(8 Suppl. 1), Abstract 2586, 1 page, AACR 101st Annual Meeting (2010).
Fenton, Bruce et al., "Pathophysiological effects of antibodies to IGF-1R and VEGFR-2 plus fractionated radiation in DU145 prostate carcinoma xenografts," Radiation Research Society 2005 Annual Meeting, Abstract No. PP109, 1 page (2005).
Ferguson, Kimberly C. et al., "The SL1 trans-spliced leader RNA performs an essential embryonic function in Caenorhabditis elegans that can also be supplied by SL2 RNA," Genes & Development, vol. 10:1543-1556 (1996).
GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages, (1996).
GenBank Accession No. CAA26536, Kornblihtt, A.R. et al., "Primary structure of human fibronectin: differential splicing may generate at least 10 polypeptides froma single gene," EMBO J., vol. 4(7):1755-1759 (1985), 7 pages, (1996).
GenBank Accession No. P07589, Skorstengaard, K. et al., "Complete primary structure of bovine plasma fibronectin," Eur. J. Biochem., vol. 161(2):441-453 (1986), 9 pages, (1997).
GenBank Accession No. X02761, Kornblihtt, A.R. et al., "Primary structure of human fibronectin: differential splicing may generate at least 10 polypeptides from a single gene," EMBO J., vol. 4(7):1755-1759 (1985), 4 pages, (1996).
Ghosh, Gourisankar et al., "Structure of NF-kappaB p50 homodimer bound to a kappaB site," Nature, vol. 373:303-310 (1995).
Goedert, M. et al., "Cloning and sequencing of the cDNA encoding an isoform of microtubule-associated protein tau containing four tandem repeats: differential expression of tau protein mRNAs in human brain," The EMBO Journal, vol. 8(2):393-399 (1989).
Grant, Richard P. et al., "Structural Requirements for Biological Activity of the Ninth and Tenth Fill Domains of Human Fibronectin," The Journal of Biological Chemistry, vol. 272(10):6159-6166 (1997).
Hackel, B. et al., "Picomolar affinity fibronectin domains engineered utilizing loop length diversity, recursive mutagenesis, and loop shuffling", Journal of Molecular Biology, vol. 381(5):1238-1252 (2008).
Hamers-Casterman, C. et al., "Naturally occurring antibodies devoid of light chains," Nature, vol. 363:446-448 (1993).
Hammond, Philip W. et al., "In Vitro Selection and Characterization of Bcl-XL-binding Proteins from a Mix of Tissue-specific mRNA Display Libraries," The Journal of Biological Chemistry, vol. 276(24):20898-20906 (2001).
Harpaz, Yahouda et al., "Many of the Immunoglobulin Superfamily Domains in Cell Adhesion Molecules and Surface Receptors Belong to a New Structural Set Which is Close to That Containing Variable Domains," J. Mol. Biol., vol. 238:528-539 (1994).
Hocking, Denise C. et al., "A Novel Role for the Integrin-binding III-10 Module in Fibronectin Matrix Assembly," The Journal of Cell Biology, vol. 133(2):431-444 (1996).
Hocking, Denise C. et al., "Activation of Distinct alpha5beta1-mediated Signaling Pathways by Fibronectin's Cell Adhesion and Matrix Assembly Domains," The Journal of Cell Biology, vol. 141(1):241-253 (1998).
Husimi, Y. et al., "Role of the Virus-type Strategy in Encoded Molecular Evolution," Progress in Biophysics and Molecular Biology, vol. 65(Suppl. 1):64 (1996).
Hynes, Richard O. et al., "Integrins: Versatility, Modulation, and Signaling in Cell Adhesion," Cell, vol. 69:11-25 (1992).
International Preliminary Report on Patentability, PCT/US2016/053183, dated Mar. 27, 2018, 7 pages.
International Search Report and Written Opinion, PCT/US2016/053183, dated Jan. 11, 2017, 11 pages.
Jung, Gyoo Yeol et al., "A Functional Protein Chip for Pathway Optimization and in Vitro Metabolic Engineering," Science, vol. 304:428-431 (2004).
Keefe, Anthony D. et al., "Functional proteins from a random-sequence library," Nature, vol. 410:715-718 (2001).
King, Catherine A. et al., "DNA vaccines with single-chain Fv fused to fragment C of tetanus toxin induce protective immunity against lymphoma and myeloma," Nature Medicine, vol. 4(11):1281-1286 (1998).
Klohn P-C et al., "IBC's 23nd Annual Antibody Engineering, 10th Annual Antibody Therapeutics International Conferences and the 2012 Annual Meeting of the Antibody Society: Dec. 3-6, 2012,San Diego, CA", MABS, vol. 5(2): 178-201 (2013).
Kohler, G. et al., "Continuous cultures of fused cells secreting antibody of predefined specificity," Nature, vol. 256:495-497 (1975).
Koide, Akiko et al., "Monobodies. Antibody Mimics Based on the Scaffold of the Fibronectin Type III Domain," Methods in Molecular Biology, vol. 352: Protein Engineering Protocols, K.M. Arndt (Ed.), Humana Press, Totowa, NJ, Chapter 6, pp. 95-109 (2007).
Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Akiko et al., "The Fibronectin Type III Domain as a Scaffold for Novel Binding Proteins," J. Mol. Biol., vol. 284:1141-1151 (1998).
Koide, Shohei et al., "Directed Evolution of Fibronectin Type III Domain to Novel Ligand Binding Proteins," FASEB J., vol. 11(9 Suppl.), Poster No. M40, p. A837, (1997).
Koide, Shohei et al., "Directed Evolution of Fibronectin Type III Domain to Novel Ligand Binding Proteins," The Faseb Journal, vol. 11(9):A1155, Poster No. 1739 (1997).
Ku, Jung et al., "Alternate protein frameworks for molecular recognition," Proc. Natl. Acad. Sci. USA, vol. 92:6552-6556 (1995).
Kurz, Markus et al., "Psoralen photo-crosslinked mRNA-puromycin conjugates: a novel template for the rapid and facile preparation of mRNA-protein fusions," Nucleic Acids Research, vol. 28(18):e83, 5 pages (2000).
Leahy, Daniel J. et al., "2.0 A Crystal Structure of a Four-Domain Segment of Human Fibronectin Encompassing the RGD Loop and Synergy Region," Cell, vol. 84:155-164 (1996).
Leahy, Daniel J. et al., "Structure of a Fibronectin Type III Domain from Tenascin Phased by MAD Analysis of the Selenomethionyl Protein," Science, vol. 258:987-991 (1992).
Lee, Grace et al., "Strong Inhibition of Fibrinogen Binding to Platelet Receptor Alpha2b beta 3 by RGD Sequences installed into the Presentation Scaffold," Prot. Eng., vol. 6:745-754 (1993).
Lipovsek D: "Adnectins: engineered target-binding protein therapeutics," Protein Engineering, Design and Selection, vol. 24 (1-2):3-9 (2010).
Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368:1024-1041 (2007).
Lipovsek, Dasa et al., "In-vitro protein evolution by ribosome display and mRNA display," Journal of Immunological Methods, vol. 290:51-67 (2004).
Litvinovich, Sergei V. et al., "Interactions Between Type III Domains in the 110 kDa Cell-binding Fragment of Fibronectin," J. Mol. Biol., vol. 248:611-626 (1995).
Lombardo, A. et al., "Conformational flexibility and crystallization of tandemly linked type III modules of human fibronectin," Protein Science, vol. 5:1934-1938 (1996).
Lu, Dan et al., "Simultaneous Blockade of Both the Epidermal Growth Factor Receptor and the Insulin-like Growth Factor Receptor Signaling Pathways in Cancer Cells with a Fully Human Recombinant Bispecific Antibody," The Journal of Biological Chemistry, vol. 279(4):2856-2865 (2004).
Main, Alison L. et al., "The Three-Dimensional Structure of the Tenth Type III Module of Fibronectin: An Insight into RGD-Mediated Interactions," Cell, vol. 71:671-678 (1992).
Mao, Yong et al., "Fibronectin fibrillogenesis, a cell-mediated matrix assembly process," Matrix Biology, vol. 24:389-399 (2005).
Markland, William et al., "Iterative Optimization of High-Affinity Protease Inhibitors Using Phage Display. 1. Plasmin," Biochemistry, vol. 35:8045-8057 (1996).

(56) References Cited

OTHER PUBLICATIONS

Markland, William et al., "Iterative Optimization of High-Affinity Protease Inhibitors Using Phage Display. 2. Plasma Kallikrein and Thrombin," Biochemistry, vol. 35:8058-8067 (1996).
Maruyama, Kazuo et al., "Oligo-capping: a simple method to replace the cap structure of eukaryotic mRNAs with oligoribonucleotides," Gene, vol. 138:171-174 (1994).
Mattheakis, Larry C. et al., "An in vitro polysome display system for identifying ligands from very large peptide libraries," Proc. Natl. Acad. Sci. USA, vol. 91:9022-9026 (1994).
McConnell, Stephen J. et al., "Tendamistat as a Scaffold for Conformationally Constrained Phage Peptide Libraries," J. Mol. Biol., vol. 250:460-470 (1995).
Meinke, A. et al., "Cellulose-Binding Polypeptides from Cellulomonas fimi: Endoglucanase D (CenD), a Family A beta-1,4-Glucanase," Journal of Bacteriology, vol. 175(7):1910-1918 (1993).
Muller, Christoph W. et al., "Structure of the NF-kappaB p50 homodimer bound to DNA," Nature, vol. 373:311-317 (1995).
Muyldermans, Serge, "Single domain camel antibodies: current status," Reviews in Molecular Biotechnology, vol. 74:277-302 (2001).
Nemoto, Naoto et al., "In vitro virus: Bonding of mRNA bearing puromycin at the 3'-terminal end to the C-terminal end of its encoded protein on the ribosome in vitro," FEBS Letters, vol. 414:405-408 (1997).
Ngo, J. Thomas et al., "Computational Complexity Protein Structure Prediction, and the Levinthal Paradox," The Protein Folding Problem and Tertiary Structure Prediction, Birkhauser, Boston, MA, K. Merz (Ed.), Chapter 14, pp. 491-495 (1994).
Niemeyer, Christof M. et al., "Oligonucleotide-directed self-assembly of proteins: semisynthetic DNA—streptavidin hybrid molecules as connectors for the generation of macroscopic arrays and the construction of supramolecular bioconjugates," Nucleic Acids Research, vol. 22(25):5530-5539 (1994).
Nilsen, Timothy W., "Trans-Splicing in Protozoa and Helminths," Infectious Agents and Disease, vol. 1:212-218 (1992).
Nord, Karin et al., "A combinatorial library of an alpha-helical bacterial receptor domain," Prot. Eng., vol. 8:601-608 (1995).
Nord, Karin et al., "Binding proteins selected from combinatorial libraries of an alpha-helical bacterial receptor domain," Nature Biotechnology, vol. 15:772-777 (1997).
Notice of Opposition to European Patent No. 1137941 (Application No. 99 967 261.1), 29 pages, dated May 11, 2010.
Nygren, Per-Ake et al., "Scaffolds for engineering novel binding sites in proteins," Current Opinion in Structural Biology, vol. 7:463-469 (1997).
Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).
Partial European Search Report for Application No. 01981621.4, 5 pages, dated Feb. 25, 2005.
Plaxco, Kevin W. et al., "A Comparison of the Folding Kinetics and Thermodynamics of Two Homologous Fibronectin Type III Modules," J. Mol. Biol., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Potts, Jennifer R. et al., "Fibronectin structure and assembly," Current Biology, vol. 6:648-655 (1994).
Potts, Jennifer R. et al., "Structure and Function of Fibronectin Modules," Matrix Biology, vol. 15:313-320 (1996).
Roberts, Richard W. et al., "RNA-peptide fusions for the in vitro selection of peptides and proteins," Proc. Natl. Acad. Sci. USA, vol. 94:12297-12302 (1997).
U.S. Appl. No. 15/127,166, Oct. 19, 2018.
U.S. Appl. No. 15/363,724, Oct. 11, 2018.

SEQUENCE LISTING

<160> NUMBER OF SEQ ID NOS: 173

<210> SEQ ID NO 1
<211> LENGTH: 94
<212> TYPE: PRT
<213> ORGANISM: Homo sapiens
<220> FEATURE:
<221> NAME/KEY: misc_feature
<223> OTHER INFORMATION: Wild-type human 10Fn3 domain

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp

```
                 65                  70                  75                  80
Ser Pro Ala Ser Ser Lys Pro Ile Ser Ile Asn Tyr Arg Thr
                         85                  90

<210> SEQ ID NO 2
<211> LENGTH: 166
<212> TYPE: PRT
<213> ORGANISM: Homo sapiens
<220> FEATURE:
<221> NAME/KEY: misc_feature
<223> OTHER INFORMATION: Wild-type human 10Fn3 domain w/loop sequences
      generically defined
<220> FEATURE:
<221> NAME/KEY: misc_feature
<222> LOCATION: (14)..(33)
<223> OTHER INFORMATION: At least 2 and up to 20 Xaa may be present; if
      present, Xaa can be any naturally occurring amino acid
<220> FEATURE:
<221> NAME/KEY: misc_feature
<222> LOCATION: (39)..(58)
<223> OTHER INFORMATION: At least 2 and up to 20 Xaa may be present; if
      present, Xaa can be any naturally occurring amino acid
<220> FEATURE:
<221> NAME/KEY: misc_feature
<222> LOCATION: (64)..(83)
<223> OTHER INFORMATION: At least 2 and up to 20 Xaa may be present; if
      present, Xaa can be any naturally occurring amino acid
<220> FEATURE:
<221> NAME/KEY: misc_feature
<222> LOCATION: (87)..(106)
<223> OTHER INFORMATION: At least 2 and up to 20 Xaa may be present; if
      present, Xaa can be any naturally occurring amino acid
<220> FEATURE:
<221> NAME/KEY: misc_feature
<222> LOCATION: (113)..(132)
<223> OTHER INFORMATION: At least 2 and up to 20 Xaa may be present; if
      present, Xaa can be any naturally occurring amino acid
<220> FEATURE:
<221> NAME/KEY: misc_feature
<222> LOCATION: (140)..(159)
<223> OTHER INFORMATION: At least 2 and up to 20 Xaa may be present; if
      present, Xaa can be any naturally occurring amino acid

<400> SEQUENCE: 2

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
            85                  90                  95

Xaa Xaa Xaa Xaa Xaa Xaa Xaa Xaa Xaa Ala Thr Ile Ser Gly Leu
                100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr
                165
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic: N-terminal leader

<400> SEQUENCE: 3

Met Gly Val Ser Asp Val Pro Arg Asp Leu
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic: N-terminal leader

<400> SEQUENCE: 4

Gly Val Ser Asp Val Pro Arg Asp Leu
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(5)
<223> OTHER INFORMATION: Any one or all Xaa can either be present or
      absent; if present, Xaa can be any naturally occurring amino acid

<400> SEQUENCE: 5

Xaa Xaa Xaa Xaa Xaa Ser Asp Val Pro Arg Asp Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(5)
<223> OTHER INFORMATION: Any one or all Xaa can either be present or
      absent; if present, Xaa can be any naturally occurring amino acid

<400> SEQUENCE: 6

Xaa Xaa Xaa Xaa Xaa Asp Val Pro Arg Asp Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(5)
<223> OTHER INFORMATION: Any one or all Xaa can either be present or
      absent; if present, Xaa can be any naturally occurring amino acid

<400> SEQUENCE: 7

Xaa Xaa Xaa Xaa Xaa Val Pro Arg Asp Leu
```

-continued

```
1               5                   10
```

<210> SEQ ID NO 8
<211> LENGTH: 9
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(5)
<223> OTHER INFORMATION: Any one or all Xaa can either be present or
      absent; if present, Xaa can be any naturally occurring amino acid

<400> SEQUENCE: 8

Xaa Xaa Xaa Xaa Xaa Pro Arg Asp Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(5)
<223> OTHER INFORMATION: Any one or all Xaa can either be present or
      absent; if present, Xaa can be any naturally occurring amino acid

<400> SEQUENCE: 9

Xaa Xaa Xaa Xaa Xaa Arg Asp Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(5)
<223> OTHER INFORMATION: Any one or all Xaa can either be present or
      absent; if present, Xaa can be any naturally occurring amino acid

<400> SEQUENCE: 10

Xaa Xaa Xaa Xaa Xaa Asp Leu
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic: N-terminal leader

<400> SEQUENCE: 11

Met Ala Ser Thr Ser Gly
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 12

```
Glu Ile Glu Lys
1

<210> SEQ ID NO 13
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 13

Glu Gly Ser Gly Cys
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 14

Glu Ile Glu Lys Pro Cys Gln
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 15

Glu Ile Glu Lys Pro Ser Gln
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 16

Glu Ile Glu Lys Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 17

Glu Ile Glu Lys Pro Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 18

Glu Ile Glu Lys Pro Cys
```

```
1               5

<210> SEQ ID NO 19
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 19

Glu Ile Asp Lys
1

<210> SEQ ID NO 20
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 20

Glu Ile Asp Lys Pro Cys Gln
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 21

Glu Ile Asp Lys Pro Ser Gln
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic: 6X His tail

<400> SEQUENCE: 22

His His His His His His
1               5

<210> SEQ ID NO 23
<211> LENGTH: 93
<212> TYPE: PRT
<213> ORGANISM: Artificial Sequence
<220> FEATURE:
<223> OTHER INFORMATION: Synthetic: 7016_A01 core (aka 2629_E06; parent
      PKE2 Adnectin)

<400> SEQUENCE: 23

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
65                  70                  75                  80
```

```
Pro Ala Ser Ser Lys Pro Ile Ser Ile Asn Tyr Arg Thr
                85                  90
```

```
<210> SEQ ID NO 24
<211> LENGTH: 116
<212> TYPE: PRT
<213> ORGANISM: Artificial Sequence
<220> FEATURE:
<223> OTHER INFORMATION: Synthetic: 7016_A01

<400> SEQUENCE: 24

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
            35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115
```

```
<210> SEQ ID NO 25
<211> LENGTH: 101
<212> TYPE: PRT
<213> ORGANISM: Artificial Sequence
<220> FEATURE:
<223> OTHER INFORMATION: Synthetic: 7016_A01 w/o his tag, C-terminal
      tail, and N-terminal MG

<400> SEQUENCE: 25

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Arg Glu Val Gln Lys Tyr Ser Asp Leu Gly Pro
            35                  40                  45

Leu Tyr Ile Tyr Gln Glu Phe Thr Val Pro Gly Ser Lys Ser Thr Ala
    50                  55                  60

Thr Ile Ser Gly Leu Lys Pro Gly Val Asp Tyr Thr Ile Thr Val Tyr
65                  70                  75                  80

Ala Val Thr Gly Ser Gly Glu Ser Pro Ala Ser Ser Lys Pro Ile Ser
                85                  90                  95

Ile Asn Tyr Arg Thr
            100
```

```
<210> SEQ ID NO 26
<211> LENGTH: 94
<212> TYPE: PRT
<213> ORGANISM: Artificial Sequence
<220> FEATURE:
<223> OTHER INFORMATION: Synthetic: 7016_A01 core with C-terminal
      proline
```

-continued

```
<400> SEQUENCE: 26

Glu Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90

<210> SEQ ID NO 27
<211> LENGTH: 102
<212> TYPE: PRT
<213> ORGANISM: Artificial Sequence
<220> FEATURE:
<223> OTHER INFORMATION: Synthetic: 7016_A01 w/o his tag, C-terminail
      tail, and N-terminal MG and w/ C-terminal proline

<400> SEQUENCE: 27

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Arg Glu Val Gln Lys Tyr Ser Asp Leu Gly Pro
        35                  40                  45

Leu Tyr Ile Tyr Gln Glu Phe Thr Val Pro Gly Ser Lys Ser Thr Ala
50                  55                  60

Thr Ile Ser Gly Leu Lys Pro Gly Val Asp Tyr Thr Ile Thr Val Tyr
65                  70                  75                  80

Ala Val Thr Gly Ser Gly Glu Ser Pro Ala Ser Ser Lys Pro Ile Ser
                85                  90                  95

Ile Asn Tyr Arg Thr Pro
            100

<210> SEQ ID NO 28
<211> LENGTH: 18
<212> TYPE: PRT
<213> ORGANISM: Artificial Sequence
<220> FEATURE:
<223> OTHER INFORMATION: Synthetic: 7016_A01 CD loop

<400> SEQUENCE: 28

Gly Arg Glu Val Gln Lys Tyr Ser Asp Leu Gly Pro Leu Tyr Ile Tyr
1               5                   10                  15

Gln Glu

<210> SEQ ID NO 29
<211> LENGTH: 13
<212> TYPE: PRT
<213> ORGANISM: Artificial Sequence
<220> FEATURE:
<223> OTHER INFORMATION: Synthetic: 7016_A01 FG loop

<400> SEQUENCE: 29

Val Thr Gly Ser Gly Glu Ser Pro Ala Ser Ser Lys Pro
1               5                   10
```

<210> SEQ ID NO 30
<211> LENGTH: 93
<212> TYPE: PRT
<213> ORGANISM: Artificial Sequence
<220> FEATURE:
<223> OTHER INFORMATION: Synthetic: 7016_G01 (Y44S) core (aka 6727_G02)

<400> SEQUENCE: 30

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ile Ser Gln Glu Phe Thr
            35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 31
<211> LENGTH: 116
<212> TYPE: PRT
<213> ORGANISM: Artificial Sequence
<220> FEATURE:
<223> OTHER INFORMATION: Synthetic: 7016_G01

<400> SEQUENCE: 31

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
            35                  40                  45

Gly Pro Leu Tyr Ile Ser Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
                100                 105                 110

His His His His
        115

<210> SEQ ID NO 32
<211> LENGTH: 101
<212> TYPE: PRT
<213> ORGANISM: Artificial Sequence
<220> FEATURE:
<223> OTHER INFORMATION: Synthetic: 7016_G01 w/o his tag, C-terminal
      tail, and N-terminal MG

<400> SEQUENCE: 32

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Arg Glu Val Gln Lys Tyr Ser Asp Leu Gly Pro
            35                  40                  45

Leu Tyr Ile Ser Gln Glu Phe Thr Val Pro Gly Ser Lys Ser Thr Ala
    50                  55                  60

Thr Ile Ser Gly Leu Lys Pro Gly Val Asp Tyr Thr Ile Thr Val Tyr
65                  70                  75                  80

Ala Val Thr Gly Ser Gly Glu Ser Pro Ala Ser Ser Lys Pro Ile Ser
                85                  90                  95

Ile Asn Tyr Arg Thr
            100

<210> SEQ ID NO 33
<211> LENGTH: 94
<212> TYPE: PRT
<213> ORGANISM: Artificial Sequence
<220> FEATURE:
<223> OTHER INFORMATION: Synthetic: 7016_G01 core with C-terminal
      proline

<400> SEQUENCE: 33

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ile Ser Gln Glu Phe Thr
            35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90

<210> SEQ ID NO 34
<211> LENGTH: 102
<212> TYPE: PRT
<213> ORGANISM: Artificial Sequence
<220> FEATURE:
<223> OTHER INFORMATION: Synthetic: 7016_G01 w/o his tag, C-terminail
      tail, and N-terminal MG and w/ C-terminal proline

<400> SEQUENCE: 34

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Arg Glu Val Gln Lys Tyr Ser Asp Leu Gly Pro
            35                  40                  45

Leu Tyr Ile Ser Gln Glu Phe Thr Val Pro Gly Ser Lys Ser Thr Ala
    50                  55                  60

Thr Ile Ser Gly Leu Lys Pro Gly Val Asp Tyr Thr Ile Thr Val Tyr
65                  70                  75                  80

Ala Val Thr Gly Ser Gly Glu Ser Pro Ala Ser Ser Lys Pro Ile Ser
                85                  90                  95

Ile Asn Tyr Arg Thr Pro
            100

<210> SEQ ID NO 35

```
<211> LENGTH: 18
<212> TYPE: PRT
<213> ORGANISM: Artificial Sequence
<220> FEATURE:
<223> OTHER INFORMATION: Synthetic: 7016_G01 CD loop, ADX_6727_A07 CD
      loop, ADX_6727_F07 CD loop, ADX_6727_G04 CD loop

<400> SEQUENCE: 35

Gly Arg Glu Val Gln Lys Tyr Ser Asp Leu Gly Pro Leu Tyr Ile Ser
1               5                   10                  15

Gln Glu

<210> SEQ ID NO 36
<211> LENGTH: 93
<212> TYPE: PRT
<213> ORGANISM: Artificial Sequence
<220> FEATURE:
<223> OTHER INFORMATION: Synthetic: 7016_E02 (L38T) core (aka 6727_E08)

<400> SEQUENCE: 36

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Thr Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 37
<211> LENGTH: 116
<212> TYPE: PRT
<213> ORGANISM: Artificial Sequence
<220> FEATURE:
<223> OTHER INFORMATION: Synthetic: 7016_E02

<400> SEQUENCE: 37

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Thr
        35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
                100                 105                 110

His His His His
        115

<210> SEQ ID NO 38
<211> LENGTH: 101
```

```
<212> TYPE: PRT
<213> ORGANISM: Artificial Sequence
<220> FEATURE:
<223> OTHER INFORMATION: Synthetic: 7016_E02 w/o his tag, C-terminal
      tail, and N-terminal MG

<400> SEQUENCE: 38

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Arg Glu Val Gln Lys Tyr Ser Asp Thr Gly Pro
        35                  40                  45

Leu Tyr Ile Tyr Gln Glu Phe Thr Val Pro Gly Ser Lys Ser Thr Ala
    50                  55                  60

Thr Ile Ser Gly Leu Lys Pro Gly Val Asp Tyr Thr Ile Thr Val Tyr
65                  70                  75                  80

Ala Val Thr Gly Ser Gly Glu Ser Pro Ala Ser Ser Lys Pro Ile Ser
                85                  90                  95

Ile Asn Tyr Arg Thr
                100

<210> SEQ ID NO 39
<211> LENGTH: 94
<212> TYPE: PRT
<213> ORGANISM: Artificial Sequence
<220> FEATURE:
<223> OTHER INFORMATION: Synthetic: 7016_E02 core with C-terminal
      proline

<400> SEQUENCE: 39

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Thr Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90

<210> SEQ ID NO 40
<211> LENGTH: 102
<212> TYPE: PRT
<213> ORGANISM: Artificial Sequence
<220> FEATURE:
<223> OTHER INFORMATION: Synthetic: 7016_E02 w/o his tag, C-terminail
      tail, and N-terminal MG and w/ C-terminal proline

<400> SEQUENCE: 40

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Arg Glu Val Gln Lys Tyr Ser Asp Thr Gly Pro
        35                  40                  45

Leu Tyr Ile Tyr Gln Glu Phe Thr Val Pro Gly Ser Lys Ser Thr Ala
```

```
                50                  55                  60
Thr Ile Ser Gly Leu Lys Pro Gly Val Asp Tyr Thr Ile Thr Val Tyr
 65                  70                  75                  80

Ala Val Thr Gly Ser Gly Glu Ser Pro Ala Ser Ser Lys Pro Ile Ser
                 85                  90                  95

Ile Asn Tyr Arg Thr Pro
            100

<210> SEQ ID NO 41
<211> LENGTH: 18
<212> TYPE: PRT
<213> ORGANISM: Artificial Sequence
<220> FEATURE:
<223> OTHER INFORMATION: Synthetic: 7016_E02 CD loop, ADX_6727_B09 CD
      loop, ADX_6727_H08 CD loop

<400> SEQUENCE: 41

Gly Arg Glu Val Gln Lys Tyr Ser Asp Thr Gly Pro Leu Tyr Ile Tyr
 1               5                  10                  15

Gln Glu

<210> SEQ ID NO 42
<211> LENGTH: 93
<212> TYPE: PRT
<213> ORGANISM: Artificial Sequence
<220> FEATURE:
<223> OTHER INFORMATION: Synthetic: 7016_C03 (Y44Q) core (aka 6727_B03)

<400> SEQUENCE: 42

Glu Val Val Ala Ala Thr Pro Thr Ser Leu Leu Ile Ser Trp Asp Ala
 1               5                  10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ile Gln Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
 65                  70                  75                  80

Pro Ala Ser Ser Lys Pro Ile Ser Ile Asn Tyr Arg Thr
                 85                  90

<210> SEQ ID NO 43
<211> LENGTH: 116
<212> TYPE: PRT
<213> ORGANISM: Artificial Sequence
<220> FEATURE:
<223> OTHER INFORMATION: Synthetic: 7016_C03

<400> SEQUENCE: 43

Met Gly Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
            35                  40                  45

Gly Pro Leu Tyr Ile Gln Gln Glu Phe Thr Val Pro Gly Ser Lys Ser
        50                  55                  60

Thr Ala Thr Ile Ser Gly Leu Lys Pro Gly Val Asp Tyr Thr Ile Thr
 65                  70                  75                  80
```

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115

<210> SEQ ID NO 44
<211> LENGTH: 101
<212> TYPE: PRT
<213> ORGANISM: Artificial Sequence
<220> FEATURE:
<223> OTHER INFORMATION: Synthetic: 7016_C03 w/o his tag, C-terminal
      tail, and N-terminal MG

<400> SEQUENCE: 44

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Arg Glu Val Gln Lys Tyr Ser Asp Leu Gly Pro
        35                  40                  45

Leu Tyr Ile Gln Gln Glu Phe Thr Val Pro Gly Ser Lys Ser Thr Ala
50                  55                  60

Thr Ile Ser Gly Leu Lys Pro Gly Val Asp Tyr Thr Ile Thr Val Tyr
65                  70                  75                  80

Ala Val Thr Gly Ser Gly Glu Ser Pro Ala Ser Ser Lys Pro Ile Ser
                85                  90                  95

Ile Asn Tyr Arg Thr
            100

<210> SEQ ID NO 45
<211> LENGTH: 94
<212> TYPE: PRT
<213> ORGANISM: Artificial Sequence
<220> FEATURE:
<223> OTHER INFORMATION: Synthetic: 7016_C03 core with C-terminal
      proline

<400> SEQUENCE: 45

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ile Gln Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90

<210> SEQ ID NO 46
<211> LENGTH: 102
<212> TYPE: PRT
<213> ORGANISM: Artificial Sequence
<220> FEATURE:
<223> OTHER INFORMATION: Synthetic: 7016_C03 w/o his tag, C-terminail
      tail, and N-terminal MG and w/ C-terminal proline

```
<400> SEQUENCE: 46

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Arg Glu Val Gln Lys Tyr Ser Asp Leu Gly Pro
            35                  40                  45

Leu Tyr Ile Gln Gln Glu Phe Thr Val Pro Gly Ser Lys Ser Thr Ala
    50                  55                  60

Thr Ile Ser Gly Leu Lys Pro Gly Val Asp Tyr Thr Ile Thr Val Tyr
65                  70                  75                  80

Ala Val Thr Gly Ser Gly Glu Ser Pro Ala Ser Ser Lys Pro Ile Ser
                85                  90                  95

Ile Asn Tyr Arg Thr Pro
            100

<210> SEQ ID NO 47
<211> LENGTH: 18
<212> TYPE: PRT
<213> ORGANISM: Artificial Sequence
<220> FEATURE:
<223> OTHER INFORMATION: Synthetic: 7016_C03 CD loop, ADX_6727_H06 CD
      loop

<400> SEQUENCE: 47

Gly Arg Glu Val Gln Lys Tyr Ser Asp Leu Gly Pro Leu Tyr Ile Gln
1               5                   10                  15

Gln Glu

<210> SEQ ID NO 48
<211> LENGTH: 93
<212> TYPE: PRT
<213> ORGANISM: Artificial Sequence
<220> FEATURE:
<223> OTHER INFORMATION: Synthetic: ADX_6727_C01 (K85A) core

<400> SEQUENCE: 48

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Ala Pro Ile Ser Ile Asn Tyr Arg Thr
                85                  90

<210> SEQ ID NO 49
<211> LENGTH: 116
<212> TYPE: PRT
<213> ORGANISM: Artificial Sequence
<220> FEATURE:
<223> OTHER INFORMATION: Synthetic: ADX_6727_C01

<400> SEQUENCE: 49

Met Gly Val Ser Asp Val Pro Arg Asp Leu Glu Val Val Ala Ala Thr
```

```
                1               5                   10                  15
        Pro Thr Ser Leu Leu Ile Ser Trp Asp Ala Pro Ala Val Thr Val Arg
                        20                  25                  30

Tyr Tyr Arg Ile Thr Tyr Gly Arg Glu Val Gln Lys Tyr Ser Asp Leu
                    35                  40                  45

Gly Pro Leu Tyr Ile Tyr Gln Glu Phe Thr Val Pro Gly Ser Lys Ser
                50                  55                  60

Thr Ala Thr Ile Ser Gly Leu Lys Pro Gly Val Asp Tyr Thr Ile Thr
         65                 70                  75                  80

Val Tyr Ala Val Thr Gly Ser Gly Glu Ser Pro Ala Ser Ser Ala Pro
                        85                  90                  95

Ile Ser Ile Asn Tyr Arg Thr Glu Ile Asp Lys Pro Ser Gln His His
                       100                 105                 110

His His His His
                115

<210> SEQ ID NO 50
<211> LENGTH: 13
<212> TYPE: PRT
<213> ORGANISM: Artificial Sequence
<220> FEATURE:
<223> OTHER INFORMATION: Synthetic: ADX_6727_C01 FG loop, ADX_6727_G10
      FG loop, ADX_6727_F04 FG loop, ADX_6727_G05 FG loop, ADX_6727_F07
      FG loop

<400> SEQUENCE: 50

Val Thr Gly Ser Gly Glu Ser Pro Ala Ser Ser Ala Pro
1               5                   10

<210> SEQ ID NO 51
<211> LENGTH: 93
<212> TYPE: PRT
<213> ORGANISM: Artificial Sequence
<220> FEATURE:
<223> OTHER INFORMATION: Synthetic: ADX_6727_D01 (K85T) core

<400> SEQUENCE: 51

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
 65                 70                  75                  80

Pro Ala Ser Ser Thr Pro Ile Ser Ile Asn Tyr Arg Thr
                85                  90

<210> SEQ ID NO 52
<211> LENGTH: 116
<212> TYPE: PRT
<213> ORGANISM: Artificial Sequence
<220> FEATURE:
<223> OTHER INFORMATION: Synthetic: ADX_6727_D01

<400> SEQUENCE: 52

Met Gly Val Ser Asp Val Pro Arg Asp Leu Glu Val Val Ala Ala Thr
1               5                   10                  15
```

```
Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Thr Pro
                85                  90                  95

Ile Ser Ile Asn Tyr Arg Thr Glu Ile Asp Lys Pro Ser Gln His His
                100                 105                 110

His His His His
        115
```

<210> SEQ ID NO 53
<211> LENGTH: 13
<212> TYPE: PRT
<213> ORGANISM: Artificial Sequence
<220> FEATURE:
<223> OTHER INFORMATION: Synthetic: ADX_6727_D01 FG loop, ADX_6727_F06 FG loop,
      ADX_6727_B05 FG loop, ADX_6727_D10 FG loop, ADX_6727_B09 FG loop,
      ADX_6727_F10 FG loop, ADX_6727_A07 FG loop, ADX_6727_H08 FG loop,
      ADX_6727_H06 FG loop

<400> SEQUENCE: 53

```
Val Thr Gly Ser Gly Glu Ser Pro Ala Ser Ser Thr Pro
1               5                   10
```

<210> SEQ ID NO 54
<211> LENGTH: 93
<212> TYPE: PRT
<213> ORGANISM: Artificial Sequence
<220> FEATURE:
<223> OTHER INFORMATION: Synthetic: ADX_6727_B01 (K85S) core

<400> SEQUENCE: 54

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Ser Pro Ile Ser Ile Asn Tyr Arg Thr
                85                  90
```

<210> SEQ ID NO 55
<211> LENGTH: 116
<212> TYPE: PRT
<213> ORGANISM: Artificial Sequence
<220> FEATURE:
<223> OTHER INFORMATION: Synthetic: ADX_6727_B01

<400> SEQUENCE: 55

```
Met Gly Val Ser Asp Val Pro Arg Asp Leu Glu Val Val Ala Ala Thr
1               5                   10                  15
```

```
Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
            35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Ser Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 56
<211> LENGTH: 13
<212> TYPE: PRT
<213> ORGANISM: Artificial Sequence
<220> FEATURE:
<223> OTHER INFORMATION: Synthetic: ADX_6727_B01 FG loop, ADX_6727_B04
      FG loop, ADX_6727_C07 FG loop, ADX_6727_D06 FG loop, ADX_6727_B11
      FG loop, ADX_6727_G06 FG loop, ADX_6727_G04 FG loop, ADX_6727_H10
      FG loop

<400> SEQUENCE: 56

```
Val Thr Gly Ser Gly Glu Ser Pro Ala Ser Ser Ser Pro
1               5                   10
```

<210> SEQ ID NO 57
<211> LENGTH: 93
<212> TYPE: PRT
<213> ORGANISM: Artificial Sequence
<220> FEATURE:
<223> OTHER INFORMATION: Synthetic: ADX_6727_B04 (Y35S/K85S) core

<400> SEQUENCE: 57

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Ser Ser Asp Leu Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Ser Pro Ile Ser Ile Asn Tyr Arg Thr
                85                  90
```

<210> SEQ ID NO 58
<211> LENGTH: 116
<212> TYPE: PRT
<213> ORGANISM: Artificial Sequence
<220> FEATURE:
<223> OTHER INFORMATION: Synthetic: ADX_6727_B04

<400> SEQUENCE: 58

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
```

```
                    20                  25                  30
Tyr Tyr Arg Ile Thr Tyr Gly Arg Glu Val Gln Lys Ser Ser Asp Leu
            35                  40                  45

Gly Pro Leu Tyr Ile Tyr Gln Glu Phe Thr Val Pro Gly Ser Lys Ser
        50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Ser Pro
                85                  90                  95

Ile Ser Ile Asn Tyr Arg Thr Glu Ile Asp Lys Pro Ser Gln His His
            100                 105                 110

His His His His
        115

<210> SEQ ID NO 59
<211> LENGTH: 18
<212> TYPE: PRT
<213> ORGANISM: Artificial Sequence
<220> FEATURE:
<223> OTHER INFORMATION: Synthetic: ADX_6727_B04 CD loop, ADX_6727_G10
      CD loop, ADX_6727_C03 CD loop

<400> SEQUENCE: 59

Gly Arg Glu Val Gln Lys Ser Ser Asp Leu Gly Pro Leu Tyr Ile Tyr
1               5                   10                  15

Gln Glu

<210> SEQ ID NO 60
<211> LENGTH: 93
<212> TYPE: PRT
<213> ORGANISM: Artificial Sequence
<220> FEATURE:
<223> OTHER INFORMATION: Synthetic: ADX_6727_G10 (Y35S/K85A) core

<400> SEQUENCE: 60

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Ser Ser Asp Leu Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
65                  70                  75                  80

Pro Ala Ser Ser Ala Pro Ile Ser Ile Asn Tyr Arg Thr
                85                  90

<210> SEQ ID NO 61
<211> LENGTH: 116
<212> TYPE: PRT
<213> ORGANISM: Artificial Sequence
<220> FEATURE:
<223> OTHER INFORMATION: Synthetic: ADX_6727_G10

<400> SEQUENCE: 61

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30
```

```
Tyr Tyr Arg Ile Thr Tyr Gly Arg Glu Val Gln Lys Ser Ser Asp Leu
            35                  40                  45

Gly Pro Leu Tyr Ile Tyr Gln Glu Phe Thr Val Pro Gly Ser Lys Ser
        50                  55                  60

Thr Ala Thr Ile Ser Gly Leu Lys Pro Gly Val Asp Tyr Thr Ile Thr
 65                  70                  75                  80

Val Tyr Ala Val Thr Gly Ser Gly Glu Ser Pro Ala Ser Ser Ala Pro
                    85                  90                  95

Ile Ser Ile Asn Tyr Arg Thr Glu Ile Asp Lys Pro Ser Gln His His
                100                 105                 110

His His His His
        115

<210> SEQ ID NO 62
<211> LENGTH: 93
<212> TYPE: PRT
<213> ORGANISM: Artificial Sequence
<220> FEATURE:
<223> OTHER INFORMATION: Synthetic: ADX_6727_C07 (R30A/K85S) core

<400> SEQUENCE: 62

Glu Val Val Ala Ala Thr Pro Thr Ser Leu Leu Ile Ser Trp Asp Ala
 1               5                  10                  15

Pro Ala Val Thr Val Arg Tyr Tyr Arg Ile Thr Tyr Gly Ala Glu Val
                20                  25                  30

Gln Lys Tyr Ser Asp Leu Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
 65                  70                  75                  80

Pro Ala Ser Ser Ser Pro Ile Ser Ile Asn Tyr Arg Thr
                85                  90

<210> SEQ ID NO 63
<211> LENGTH: 116
<212> TYPE: PRT
<213> ORGANISM: Artificial Sequence
<220> FEATURE:
<223> OTHER INFORMATION: Synthetic: ADX_6727_C07

<400> SEQUENCE: 63

Met Gly Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
                20                  25                  30

Tyr Tyr Arg Ile Thr Tyr Gly Ala Glu Val Gln Lys Tyr Ser Asp Leu
            35                  40                  45

Gly Pro Leu Tyr Ile Tyr Gln Glu Phe Thr Val Pro Gly Ser Lys Ser
        50                  55                  60

Thr Ala Thr Ile Ser Gly Leu Lys Pro Gly Val Asp Tyr Thr Ile Thr
 65                  70                  75                  80

Val Tyr Ala Val Thr Gly Ser Gly Glu Ser Pro Ala Ser Ser Ser Pro
                    85                  90                  95

Ile Ser Ile Asn Tyr Arg Thr Glu Ile Asp Lys Pro Ser Gln His His
                100                 105                 110

His His His His
```

```
        115

<210> SEQ ID NO 64
<211> LENGTH: 18
<212> TYPE: PRT
<213> ORGANISM: Artificial Sequence
<220> FEATURE:
<223> OTHER INFORMATION: Synthetic: ADX_6727_C07 CD loop

<400> SEQUENCE: 64

Gly Ala Glu Val Gln Lys Tyr Ser Asp Leu Gly Pro Leu Tyr Ile Tyr
1               5                   10                  15

Gln Glu

<210> SEQ ID NO 65
<211> LENGTH: 93
<212> TYPE: PRT
<213> ORGANISM: Artificial Sequence
<220> FEATURE:
<223> OTHER INFORMATION: Synthetic: ADX_6727_C03 (Y35S) core

<400> SEQUENCE: 65

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Ser Ser Asp Leu Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 66
<211> LENGTH: 116
<212> TYPE: PRT
<213> ORGANISM: Artificial Sequence
<220> FEATURE:
<223> OTHER INFORMATION: Synthetic: ADX_6727_C03

<400> SEQUENCE: 66

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Ser Ser Asp Leu
        35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 67
<211> LENGTH: 93
<212> TYPE: PRT
<213> ORGANISM: Artificial Sequence
<220> FEATURE:
<223> OTHER INFORMATION: Synthetic: ADX_6727_D02 (R30N) core

<400> SEQUENCE: 67

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Asn Glu Val
                20                  25                  30

Gln Lys Tyr Ser Asp Leu Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 68
<211> LENGTH: 116
<212> TYPE: PRT
<213> ORGANISM: Artificial Sequence
<220> FEATURE:
<223> OTHER INFORMATION: Synthetic: ADX_6727_D02

<400> SEQUENCE: 68

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Asn Glu Val Gln Lys Tyr Ser Asp Leu
            35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
                100                 105                 110

His His His His
        115

<210> SEQ ID NO 69
<211> LENGTH: 18
<212> TYPE: PRT
<213> ORGANISM: Artificial Sequence
<220> FEATURE:
<223> OTHER INFORMATION: Synthetic: ADX_6727_D02 CD loop

<400> SEQUENCE: 69

Gly Asn Glu Val Gln Lys Tyr Ser Asp Leu Gly Pro Leu Tyr Ile Tyr
1               5                   10                  15

Gln Glu

<210> SEQ ID NO 70

```
<211> LENGTH: 93
<212> TYPE: PRT
<213> ORGANISM: Artificial Sequence
<220> FEATURE:
<223> OTHER INFORMATION: Synthetic: ADX_6727_F06 (L41A/K85T) core

<400> SEQUENCE: 70

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Ala Tyr Ile Tyr Gln Glu Phe Thr
            35                  40                  45

Val Pro Gly Ser Lys Ser Thr Ala Thr Ile Ser Gly Leu Lys Pro Gly
50                  55                  60

Val Asp Tyr Thr Ile Thr Val Tyr Ala Val Thr Gly Ser Gly Glu Ser
65                  70                  75                  80

Pro Ala Ser Ser Thr Pro Ile Ser Ile Asn Tyr Arg Thr
                85                  90

<210> SEQ ID NO 71
<211> LENGTH: 116
<212> TYPE: PRT
<213> ORGANISM: Artificial Sequence
<220> FEATURE:
<223> OTHER INFORMATION: Synthetic: ADX_6727_F06

<400> SEQUENCE: 71

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
            35                  40                  45

Gly Pro Ala Tyr Ile Tyr Gln Glu Phe Thr Val Pro Gly Ser Lys Ser
50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Thr Pro
                85                  90                  95

Ile Ser Ile Asn Tyr Arg Thr Glu Ile Asp Lys Pro Ser Gln His His
            100                 105                 110

His His His His
        115

<210> SEQ ID NO 72
<211> LENGTH: 18
<212> TYPE: PRT
<213> ORGANISM: Artificial Sequence
<220> FEATURE:
<223> OTHER INFORMATION: Synthetic: ADX_6727_F06 CD loop, ADX_6727_G01
      CD loop

<400> SEQUENCE: 72

Gly Arg Glu Val Gln Lys Tyr Ser Asp Leu Gly Pro Ala Tyr Ile Tyr
1               5                   10                  15

Gln Glu

<210> SEQ ID NO 73
<211> LENGTH: 93
```

<212> TYPE: PRT
<213> ORGANISM: Artificial Sequence
<220> FEATURE:
<223> OTHER INFORMATION: Synthetic: ADX_6727_G01 (L41A) core

<400> SEQUENCE: 73

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Ala Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 74
<211> LENGTH: 116
<212> TYPE: PRT
<213> ORGANISM: Artificial Sequence
<220> FEATURE:
<223> OTHER INFORMATION: Synthetic: ADX_6727_G01

<400> SEQUENCE: 74

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45

Gly Pro Ala Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Gly Ile Asp Lys Pro Ser Gln His His
            100                 105                 110

His His His His
        115

<210> SEQ ID NO 75
<211> LENGTH: 93
<212> TYPE: PRT
<213> ORGANISM: Artificial Sequence
<220> FEATURE:
<223> OTHER INFORMATION: Synthetic: ADX_6727_F03 (I43A) core

<400> SEQUENCE: 75

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ala Tyr Gln Glu Phe Thr
        35                  40                  45

Val Pro Gly Ser Lys Ser Thr Ala Thr Ile Ser Gly Leu Lys Pro Gly

```
                    50                  55                  60
Val Asp Tyr Thr Ile Thr Val Tyr Ala Val Thr Gly Ser Gly Glu Ser
 65                  70                  75                  80

Pro Ala Ser Ser Lys Pro Ile Ser Ile Asn Tyr Arg Thr
                 85                  90

<210> SEQ ID NO 76
<211> LENGTH: 116
<212> TYPE: PRT
<213> ORGANISM: Artificial Sequence
<220> FEATURE:
<223> OTHER INFORMATION: Synthetic: ADX_6727_F03

<400> SEQUENCE: 76

Met Gly Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
             35                  40                  45

Gly Pro Leu Tyr Ala Tyr Gln Glu Phe Thr Val Pro Gly Ser Lys Ser
 50                  55                  60

Thr Ala Thr Ile Ser Gly Leu Lys Pro Gly Val Asp Tyr Thr Ile Thr
 65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
                100                 105                 110

His His His His
        115

<210> SEQ ID NO 77
<211> LENGTH: 18
<212> TYPE: PRT
<213> ORGANISM: Artificial Sequence
<220> FEATURE:
<223> OTHER INFORMATION: Synthetic: ADX_6727_F03 CD loop

<400> SEQUENCE: 77

Gly Arg Glu Val Gln Lys Tyr Ser Asp Leu Gly Pro Leu Tyr Ala Tyr
 1               5                  10                  15

Gln Glu

<210> SEQ ID NO 78
<211> LENGTH: 93
<212> TYPE: PRT
<213> ORGANISM: Artificial Sequence
<220> FEATURE:
<223> OTHER INFORMATION: Synthetic: ADX_6727_D06 (Y44A/K85S) core

<400> SEQUENCE: 78

Glu Val Val Ala Ala Thr Pro Thr Ser Leu Leu Ile Ser Trp Asp Ala
 1               5                  10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ile Ala Gln Glu Phe Thr
             35                  40                  45

Val Pro Gly Ser Lys Ser Thr Ala Thr Ile Ser Gly Leu Lys Pro Gly
 50                  55                  60
```

```
Val Asp Tyr Thr Ile Thr Val Tyr Ala Val Thr Gly Ser Gly Glu Ser
 65                  70                  75                  80

Pro Ala Ser Ser Ser Pro Ile Ser Ile Asn Tyr Arg Thr
                 85                  90

<210> SEQ ID NO 79
<211> LENGTH: 116
<212> TYPE: PRT
<213> ORGANISM: Artificial Sequence
<220> FEATURE:
<223> OTHER INFORMATION: Synthetic: ADX_6727_D06

<400> SEQUENCE: 79

Met Gly Val Ser Asp Val Pro Arg Asp Leu Glu Val Val Ala Ala Thr
  1               5                  10                  15

Pro Thr Ser Leu Leu Ile Ser Trp Asp Ala Pro Ala Val Thr Val Arg
                 20                  25                  30

Tyr Tyr Arg Ile Thr Tyr Gly Arg Glu Val Gln Lys Tyr Ser Asp Leu
             35                  40                  45

Gly Pro Leu Tyr Ile Ala Gln Glu Phe Thr Val Pro Gly Ser Lys Ser
 50                  55                  60

Thr Ala Thr Ile Ser Gly Leu Lys Pro Gly Val Asp Tyr Thr Ile Thr
 65                  70                  75                  80

Val Tyr Ala Val Thr Gly Ser Gly Glu Ser Pro Ala Ser Ser Ser Pro
                 85                  90                  95

Ile Ser Ile Asn Tyr Arg Thr Glu Ile Asp Lys Pro Ser Gln His His
            100                 105                 110

His His His His
        115

<210> SEQ ID NO 80
<211> LENGTH: 18
<212> TYPE: PRT
<213> ORGANISM: Artificial Sequence
<220> FEATURE:
<223> OTHER INFORMATION: Synthetic: ADX_6727_D06 CD loop, ADX_6727_F04
      CD loop

<400> SEQUENCE: 80

Gly Arg Glu Val Gln Lys Tyr Ser Asp Leu Gly Pro Leu Tyr Ile Ala
  1               5                  10                  15

Gln Glu

<210> SEQ ID NO 81
<211> LENGTH: 93
<212> TYPE: PRT
<213> ORGANISM: Artificial Sequence
<220> FEATURE:
<223> OTHER INFORMATION: Synthetic: ADX_6727_F04 (Y44A/K85A) core

<400> SEQUENCE: 81

Glu Val Val Ala Ala Thr Pro Thr Ser Leu Leu Ile Ser Trp Asp Ala
  1               5                  10                  15

Pro Ala Val Thr Val Arg Tyr Tyr Arg Ile Thr Tyr Gly Arg Glu Val
                 20                  25                  30

Gln Lys Tyr Ser Asp Leu Gly Pro Leu Tyr Ile Ala Gln Glu Phe Thr
             35                  40                  45

Val Pro Gly Ser Lys Ser Thr Ala Thr Ile Ser Gly Leu Lys Pro Gly
 50                  55                  60

Val Asp Tyr Thr Ile Thr Val Tyr Ala Val Thr Gly Ser Gly Glu Ser
```

```
                65                  70                  75                  80
Pro Ala Ser Ser Ala Pro Ile Ser Ile Asn Tyr Arg Thr
                    85                  90

<210> SEQ ID NO 82
<211> LENGTH: 116
<212> TYPE: PRT
<213> ORGANISM: Artificial Sequence
<220> FEATURE:
<223> OTHER INFORMATION: Synthetic: ADX_6727_F04

<400> SEQUENCE: 82

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
            35                  40                  45

Gly Pro Leu Tyr Ile Ala Gln Glu Phe Thr Val Pro Gly Ser Lys Ser
        50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Ala Pro
                85                  90                  95

Ile Ser Ile Asn Tyr Arg Thr Glu Ile Asp Lys Pro Ser Gln His His
                100                 105                 110

His His His His
        115

<210> SEQ ID NO 83
<211> LENGTH: 93
<212> TYPE: PRT
<213> ORGANISM: Artificial Sequence
<220> FEATURE:
<223> OTHER INFORMATION: Synthetic: ADX_6727_B05 (I43S/K85T) core

<400> SEQUENCE: 83

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ser Tyr Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
65                  70                  75                  80

Pro Ala Ser Ser Thr Pro Ile Ser Ile Asn Tyr Arg Thr
                85                  90

<210> SEQ ID NO 84
<211> LENGTH: 116
<212> TYPE: PRT
<213> ORGANISM: Artificial Sequence
<220> FEATURE:
<223> OTHER INFORMATION: Synthetic: ADX_6727_B05

<400> SEQUENCE: 84

Met Gly Val Ser Asp Val Pro Arg Asp Leu Glu Val Val Ala Ala Thr
1               5                   10                  15
```

```
Pro Thr Ser Leu Leu Ile Ser Trp Asp Ala Pro Ala Val Thr Val Arg
        20                  25                  30

Tyr Tyr Arg Ile Thr Tyr Gly Arg Glu Val Gln Lys Tyr Ser Asp Leu
        35                  40                  45

Gly Pro Leu Tyr Ser Tyr Gln Glu Phe Thr Val Pro Gly Ser Lys Ser
50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Thr Pro
                85                  90                  95

Ile Ser Ile Asn Tyr Arg Thr Glu Ile Asp Lys Pro Ser Gln His His
            100                 105                 110

His His His His
        115

<210> SEQ ID NO 85
<211> LENGTH: 18
<212> TYPE: PRT
<213> ORGANISM: Artificial Sequence
<220> FEATURE:
<223> OTHER INFORMATION: Synthetic: ADX_6727_H02 CD loop, ADX_6727_G05
      CD loop

<400> SEQUENCE: 85

Gly Arg Glu Val Gln Lys Tyr Ser Asp Leu Gly Pro Leu Tyr Ser Tyr
1               5                   10                  15

Gln Glu

<210> SEQ ID NO 86
<211> LENGTH: 93
<212> TYPE: PRT
<213> ORGANISM: Artificial Sequence
<220> FEATURE:
<223> OTHER INFORMATION: Synthetic: ADX_6727_B11 (Q33D/K85S) core

<400> SEQUENCE: 86

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Asp Lys Tyr Ser Asp Leu Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
65                  70                  75                  80

Pro Ala Ser Ser Ser Pro Ile Ser Ile Asn Tyr Arg Thr
                85                  90

<210> SEQ ID NO 87
<211> LENGTH: 116
<212> TYPE: PRT
<213> ORGANISM: Artificial Sequence
<220> FEATURE:
<223> OTHER INFORMATION: Synthetic: ADX_6727_B11

<400> SEQUENCE: 87

Met Gly Val Ser Asp Val Pro Arg Asp Leu Glu Val Val Ala Ala Thr
1               5                   10                  15
```

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Asp Lys Tyr Ser Asp Leu
        35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Ser Pro
                85                  90                  95

Ile Ser Ile Asn Tyr Arg Thr Glu Ile Asp Lys Pro Ser Gln His His
            100                 105                 110

His His His His
        115

<210> SEQ ID NO 88
<211> LENGTH: 18
<212> TYPE: PRT
<213> ORGANISM: Artificial Sequence
<220> FEATURE:
<223> OTHER INFORMATION: Synthetic: ADX_6727_B11 CD loop, ADX_6727_D10
      CD loop

<400> SEQUENCE: 88

Gly Arg Glu Val Asp Lys Tyr Ser Asp Leu Gly Pro Leu Tyr Ile Tyr
1               5                   10                  15

Gln Glu

<210> SEQ ID NO 89
<211> LENGTH: 93
<212> TYPE: PRT
<213> ORGANISM: Artificial Sequence
<220> FEATURE:
<223> OTHER INFORMATION: Synthetic: ADX_6727_D10 (Q33D/K85T) core

<400> SEQUENCE: 89

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Asp Lys Tyr Ser Asp Leu Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Thr Pro Ile Ser Ile Asn Tyr Arg Thr
                85                  90

<210> SEQ ID NO 90
<211> LENGTH: 116
<212> TYPE: PRT
<213> ORGANISM: Artificial Sequence
<220> FEATURE:
<223> OTHER INFORMATION: Synthetic: ADX_6727_D10

<400> SEQUENCE: 90

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg 20                  25                  30

Tyr Tyr Arg Ile Thr Tyr Gly Arg Glu Val Asp Lys Tyr Ser Asp Leu
            35                  40                  45

Gly Pro Leu Tyr Ile Tyr Gln Glu Phe Thr Val Pro Gly Ser Lys Ser
        50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Thr Pro
                85                  90                  95

Ile Ser Ile Asn Tyr Arg Thr Glu Ile Asp Lys Pro Ser Gln His His
            100                 105                 110

His His His His
        115

<210> SEQ ID NO 91
<211> LENGTH: 93
<212> TYPE: PRT
<213> ORGANISM: Artificial Sequence
<220> FEATURE:
<223> OTHER INFORMATION: Synthetic: ADX_6727_B09 (L38T/K85T) core

<400> SEQUENCE: 91

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Thr Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
65                  70                  75                  80

Pro Ala Ser Ser Thr Pro Ile Ser Ile Asn Tyr Arg Thr
                85                  90

<210> SEQ ID NO 92
<211> LENGTH: 116
<212> TYPE: PRT
<213> ORGANISM: Artificial Sequence
<220> FEATURE:
<223> OTHER INFORMATION: Synthetic: ADX_6727_B09

<400> SEQUENCE: 92

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Thr
            35                  40                  45

Gly Pro Leu Tyr Ile Tyr Gln Glu Phe Thr Val Pro Gly Ser Lys Ser
        50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Thr Pro
                85                  90                  95

Ile Ser Ile Asn Tyr Arg Thr Glu Ile Asp Lys Pro Ser Gln His His
            100                 105                 110

His His His His
        115

<210> SEQ ID NO 93
<211> LENGTH: 93
<212> TYPE: PRT
<213> ORGANISM: Artificial Sequence
<220> FEATURE:
<223> OTHER INFORMATION: Synthetic: ADX_6727_H02 (I43S) core

<400> SEQUENCE: 93

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ser Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 94
<211> LENGTH: 116
<212> TYPE: PRT
<213> ORGANISM: Artificial Sequence
<220> FEATURE:
<223> OTHER INFORMATION: Synthetic: ADX_6727_H02

<400> SEQUENCE: 94

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45

Gly Pro Leu Tyr Ser Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115

<210> SEQ ID NO 95
<211> LENGTH: 93
<212> TYPE: PRT
<213> ORGANISM: Artificial Sequence
<220> FEATURE:
<223> OTHER INFORMATION: Synthetic: ADX_6727_G05 (I43S/K85A) core

<400> SEQUENCE: 95

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val 20                  25                  30

Gln Lys Tyr Ser Asp Leu Gly Pro Leu Tyr Ser Tyr Gln Glu Phe Thr
            35                  40                  45

Val Pro Gly Ser Lys Ser Thr Ala Thr Ile Ser Gly Leu Lys Pro Gly
 50                  55                  60

Val Asp Tyr Thr Ile Thr Val Tyr Ala Val Thr Gly Ser Gly Glu Ser
 65                  70                  75                  80

Pro Ala Ser Ser Ala Pro Ile Ser Ile Asn Tyr Arg Thr
            85                  90

<210> SEQ ID NO 96
<211> LENGTH: 116
<212> TYPE: PRT
<213> ORGANISM: Artificial Sequence
<220> FEATURE:
<223> OTHER INFORMATION: Synthetic: ADX_6727_G05

<400> SEQUENCE: 96

Met Gly Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
            35                  40                  45

Gly Pro Leu Tyr Ser Tyr Gln Glu Phe Thr Val Pro Gly Ser Lys Ser
 50                  55                  60

Thr Ala Thr Ile Ser Gly Leu Lys Pro Gly Val Asp Tyr Thr Ile Thr
 65                  70                  75                  80

Val Tyr Ala Val Thr Gly Ser Gly Glu Ser Pro Ala Ser Ser Ala Pro
            85                  90                  95

Ile Ser Ile Asn Tyr Arg Thr Glu Ile Asp Lys Pro Ser Gln His His
            100                 105                 110

His His His His
        115

<210> SEQ ID NO 97
<211> LENGTH: 93
<212> TYPE: PRT
<213> ORGANISM: Artificial Sequence
<220> FEATURE:
<223> OTHER INFORMATION: Synthetic: ADX_6727_G06 (Y35A/K85S) core

<400> SEQUENCE: 97

Glu Val Val Ala Ala Thr Pro Thr Ser Leu Leu Ile Ser Trp Asp Ala
 1               5                  10                  15

Pro Ala Val Thr Val Arg Tyr Tyr Arg Ile Thr Tyr Gly Arg Glu Val
            20                  25                  30

Gln Lys Ala Ser Asp Leu Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
 50                  55                  60

Val Asp Tyr Thr Ile Thr Val Tyr Ala Val Thr Gly Ser Gly Glu Ser
 65                  70                  75                  80

Pro Ala Ser Ser Ser Pro Ile Ser Ile Asn Tyr Arg Thr
            85                  90

<210> SEQ ID NO 98
<211> LENGTH: 116

<212> TYPE: PRT
<213> ORGANISM: Artificial Sequence
<220> FEATURE:
<223> OTHER INFORMATION: Synthetic: ADX_6727_G06

<400> SEQUENCE: 98

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Ala Ser Asp Leu
        35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Ser Pro
                85                  90                  95

Ile Ser Ile Asn Tyr Arg Thr Glu Ile Asp Lys Pro Ser Gln His His
            100                 105                 110

His His His His
        115

<210> SEQ ID NO 99
<211> LENGTH: 18
<212> TYPE: PRT
<213> ORGANISM: Artificial Sequence
<220> FEATURE:
<223> OTHER INFORMATION: Synthetic: ADX_6727_G06 CD loop, ADX_6727_F10
      CD loop

<400> SEQUENCE: 99

Gly Arg Glu Val Gln Lys Ala Ser Asp Leu Gly Pro Leu Tyr Ile Tyr
1               5                   10                  15

Gln Glu

<210> SEQ ID NO 100
<211> LENGTH: 93
<212> TYPE: PRT
<213> ORGANISM: Artificial Sequence
<220> FEATURE:
<223> OTHER INFORMATION: Synthetic: ADX_6727_F10 (Y35A/K85T) core

<400> SEQUENCE: 100

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Ala Ser Asp Leu Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Thr Pro Ile Ser Ile Asn Tyr Arg Thr
                85                  90

<210> SEQ ID NO 101
<211> LENGTH: 116
<212> TYPE: PRT

<213> ORGANISM: Artificial Sequence
<220> FEATURE:
<223> OTHER INFORMATION: Synthetic: ADX_6727_F10

<400> SEQUENCE: 101

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Ala Ser Asp Leu
        35                  40                  45

Gly Pro Leu Tyr Ile Tyr Gln Glu Phe Thr Val Pro Gly Ser Lys Ser
50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Thr Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 102
<211> LENGTH: 93
<212> TYPE: PRT
<213> ORGANISM: Artificial Sequence
<220> FEATURE:
<223> OTHER INFORMATION: Synthetic: ADX_6727_A07 (Y44S/K85T) core

<400> SEQUENCE: 102

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ile Ser Gln Glu Phe Thr
        35                  40                  45

Val Pro Gly Ser Lys Ser Thr Ala Thr Ile Ser Gly Leu Lys Pro Gly
50                  55                  60

Val Asp Tyr Thr Ile Thr Val Tyr Ala Val Thr Gly Ser Gly Glu Ser
65                  70                  75                  80

Pro Ala Ser Ser Thr Pro Ile Ser Ile Asn Tyr Arg Thr
                85                  90
```

<210> SEQ ID NO 103
<211> LENGTH: 116
<212> TYPE: PRT
<213> ORGANISM: Artificial Sequence
<220> FEATURE:
<223> OTHER INFORMATION: Synthetic: ADX_6727_A07

<400> SEQUENCE: 103

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45

Gly Pro Leu Tyr Ile Ser Gln Glu Phe Thr Val Pro Gly Ser Lys Ser
50                  55                  60
```

```
Thr Ala Thr Ile Ser Gly Leu Lys Pro Gly Val Asp Tyr Thr Ile Thr
 65                  70                  75                  80

Val Tyr Ala Val Thr Gly Ser Gly Glu Ser Pro Ala Ser Ser Thr Pro
                 85                  90                  95

Ile Ser Ile Asn Tyr Arg Thr Glu Ile Asp Lys Pro Ser Gln His His
            100                 105                 110

His His His His
        115

<210> SEQ ID NO 104
<211> LENGTH: 93
<212> TYPE: PRT
<213> ORGANISM: Artificial Sequence
<220> FEATURE:
<223> OTHER INFORMATION: Synthetic: ADX_6727_F07 (Y44S/K85A) core

<400> SEQUENCE: 104

Glu Val Val Ala Ala Thr Pro Thr Ser Leu Leu Ile Ser Trp Asp Ala
 1               5                  10                  15

Pro Ala Val Thr Val Arg Tyr Tyr Arg Ile Thr Tyr Gly Arg Glu Val
                 20                  25                  30

Gln Lys Tyr Ser Asp Leu Gly Pro Leu Tyr Ile Ser Gln Glu Phe Thr
             35                  40                  45

Val Pro Gly Ser Lys Ser Thr Ala Thr Ile Ser Gly Leu Lys Pro Gly
 50                  55                  60

Val Asp Tyr Thr Ile Thr Val Tyr Ala Val Thr Gly Ser Gly Glu Ser
 65                  70                  75                  80

Pro Ala Ser Ser Ala Pro Ile Ser Ile Asn Tyr Arg Thr
                 85                  90

<210> SEQ ID NO 105
<211> LENGTH: 116
<212> TYPE: PRT
<213> ORGANISM: Artificial Sequence
<220> FEATURE:
<223> OTHER INFORMATION: Synthetic: ADX_6727_F07

<400> SEQUENCE: 105

Met Gly Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
                 20                  25                  30

Tyr Tyr Arg Ile Thr Tyr Gly Arg Glu Val Gln Lys Tyr Ser Asp Leu
             35                  40                  45

Gly Pro Leu Tyr Ile Ser Gln Glu Phe Thr Val Pro Gly Ser Lys Ser
 50                  55                  60

Thr Ala Thr Ile Ser Gly Leu Lys Pro Gly Val Asp Tyr Thr Ile Thr
 65                  70                  75                  80

Val Tyr Ala Val Thr Gly Ser Gly Glu Ser Pro Ala Ser Ser Ala Pro
                 85                  90                  95

Ile Ser Ile Asn Tyr Arg Thr Glu Ile Asp Lys Pro Ser Gln His His
            100                 105                 110

His His His His
        115

<210> SEQ ID NO 106
<211> LENGTH: 93
<212> TYPE: PRT
```

<213> ORGANISM: Artificial Sequence
<220> FEATURE:
<223> OTHER INFORMATION: Synthetic: ADX_6727_G04 (Y44S/K85S) core

<400> SEQUENCE: 106

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ile Ser Gln Glu Phe Thr
        35                  40                  45

Val Pro Gly Ser Lys Ser Thr Ala Thr Ile Ser Gly Leu Lys Pro Gly
50                  55                  60

Val Asp Tyr Thr Ile Thr Val Tyr Ala Val Thr Gly Ser Gly Glu Ser
65                  70                  75                  80

Pro Ala Ser Ser Ser Pro Ile Ser Ile Asn Tyr Arg Thr
                85                  90

<210> SEQ ID NO 107
<211> LENGTH: 116
<212> TYPE: PRT
<213> ORGANISM: Artificial Sequence
<220> FEATURE:
<223> OTHER INFORMATION: Synthetic: ADX_6727_G04

<400> SEQUENCE: 107

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45

Gly Pro Leu Tyr Ile Ser Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Ser Pro
                85                  90                  95

Ile Ser Ile Asn Tyr Arg Thr Glu Ile Asp Lys Pro Ser Gln His His
            100                 105                 110

His His His His
        115

<210> SEQ ID NO 108
<211> LENGTH: 93
<212> TYPE: PRT
<213> ORGANISM: Artificial Sequence
<220> FEATURE:
<223> OTHER INFORMATION: Synthetic: ADX_6727_D03 (L41S) core

<400> SEQUENCE: 108

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Ser Tyr Ile Tyr Gln Glu Phe Thr
        35                  40                  45

Val Pro Gly Ser Lys Ser Thr Ala Thr Ile Ser Gly Leu Lys Pro Gly
50                  55                  60

```
Val Asp Tyr Thr Ile Thr Val Tyr Ala Val Gly Ser Gly Glu Ser
 65                  70                  75                  80

Pro Ala Ser Ser Lys Pro Ile Ser Ile Asn Tyr Arg Thr
                 85                  90
```

<210> SEQ ID NO 109
<211> LENGTH: 116
<212> TYPE: PRT
<213> ORGANISM: Artificial Sequence
<220> FEATURE:
<223> OTHER INFORMATION: Synthetic: ADX_6727_D03

<400> SEQUENCE: 109

```
Met Gly Val Ser Asp Val Pro Arg Asp Leu Glu Val Val Ala Ala Thr
  1               5                  10                  15

Pro Thr Ser Leu Leu Ile Ser Trp Asp Ala Pro Ala Val Thr Val Arg
                 20                  25                  30

Tyr Tyr Arg Ile Thr Tyr Gly Arg Glu Val Gln Lys Tyr Ser Asp Leu
                 35                  40                  45

Gly Pro Ser Tyr Ile Tyr Gln Glu Phe Thr Val Pro Gly Ser Lys Ser
 50                  55                  60

Thr Ala Thr Ile Ser Gly Leu Lys Pro Gly Val Asp Tyr Thr Ile Thr
 65                  70                  75                  80

Val Tyr Ala Val Thr Gly Ser Gly Glu Ser Pro Ala Ser Ser Lys Pro
                 85                  90                  95

Ile Ser Ile Asn Tyr Arg Thr Glu Ile Asp Lys Pro Ser Gln His His
                100                 105                 110

His His His His
        115
```

<210> SEQ ID NO 110
<211> LENGTH: 18
<212> TYPE: PRT
<213> ORGANISM: Artificial Sequence
<220> FEATURE:
<223> OTHER INFORMATION: Synthetic: ADX_6727_D03 CD loop, ADX_6727_H10
      CD loop

<400> SEQUENCE: 110

```
Gly Arg Glu Val Gln Lys Tyr Ser Asp Leu Gly Pro Ser Tyr Ile Tyr
  1               5                  10                  15

Gln Glu
```

<210> SEQ ID NO 111
<211> LENGTH: 93
<212> TYPE: PRT
<213> ORGANISM: Artificial Sequence
<220> FEATURE:
<223> OTHER INFORMATION: Synthetic: ADX_6727_H10 (L41S/K85S) core

<400> SEQUENCE: 111

```
Glu Val Val Ala Ala Thr Pro Thr Ser Leu Leu Ile Ser Trp Asp Ala
  1               5                  10                  15

Pro Ala Val Thr Val Arg Tyr Tyr Arg Ile Thr Tyr Gly Arg Glu Val
                 20                  25                  30

Gln Lys Tyr Ser Asp Leu Gly Pro Ser Tyr Ile Tyr Gln Glu Phe Thr
                 35                  40                  45

Val Pro Gly Ser Lys Ser Thr Ala Thr Ile Ser Gly Leu Lys Pro Gly
 50                  55                  60
```

Val Asp Tyr Thr Ile Thr Val Tyr Ala Val Thr Gly Ser Gly Glu Ser
65                  70                  75                  80

Pro Ala Ser Ser Pro Ile Ser Ile Asn Tyr Arg Thr
                85                  90

<210> SEQ ID NO 112
<211> LENGTH: 116
<212> TYPE: PRT
<213> ORGANISM: Artificial Sequence
<220> FEATURE:
<223> OTHER INFORMATION: Synthetic: ADX_6727_H10

<400> SEQUENCE: 112

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
            35                  40                  45

Gly Pro Ser Tyr Ile Tyr Gln Glu Phe Thr Val Pro Gly Ser Lys Ser
        50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Ser Pro
                85                  90                  95

Ile Ser Ile Asn Tyr Arg Thr Glu Ile Asp Lys Pro Ser Gln His His
                100                 105                 110

His His His His
        115

<210> SEQ ID NO 113
<211> LENGTH: 93
<212> TYPE: PRT
<213> ORGANISM: Artificial Sequence
<220> FEATURE:
<223> OTHER INFORMATION: Synthetic: ADX_6727_H08 (L38T/K85T) core

<400> SEQUENCE: 113

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Thr Gly Pro Leu Tyr Ile Tyr Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
65                  70                  75                  80

Pro Ala Ser Ser Thr Pro Ile Ser Ile Asn Tyr Arg Thr
                85                  90

<210> SEQ ID NO 114
<211> LENGTH: 116
<212> TYPE: PRT
<213> ORGANISM: Artificial Sequence
<220> FEATURE:
<223> OTHER INFORMATION: Synthetic: ADX_6727_H08

<400> SEQUENCE: 114

Met Gly Val Ser Asp Val Pro Arg Asp Leu Glu Val Val Ala Ala Thr

```
                1               5                  10                 15
            Pro Thr Ser Leu Leu Ile Ser Trp Asp Ala Pro Ala Val Thr Val Arg
                           20                 25                 30

Tyr Tyr Arg Ile Thr Tyr Gly Arg Glu Val Gln Lys Tyr Ser Asp Thr
                       35                 40                 45

Gly Pro Leu Tyr Ile Tyr Gln Glu Phe Thr Val Pro Gly Ser Lys Ser
                   50                 55                 60

Thr Ala Thr Ile Ser Gly Leu Lys Pro Gly Val Asp Tyr Thr Ile Thr
            65                 70                 75                 80

Val Tyr Ala Val Thr Gly Ser Gly Glu Ser Pro Ala Ser Ser Thr Pro
                           85                 90                 95

Ile Ser Ile Asn Tyr Arg Thr Glu Ile Asp Lys Pro Ser Gln His His
                          100                105                110

His His His His
                    115

<210> SEQ ID NO 115
<211> LENGTH: 93
<212> TYPE: PRT
<213> ORGANISM: Artificial Sequence
<220> FEATURE:
<223> OTHER INFORMATION: Synthetic: ADX_6727_H06 (Y44Q/K95T) core

<400> SEQUENCE: 115

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ile Gln Gln Glu Phe Thr
            35                  40                  45

Val Pro Gly Ser Lys Ser Thr Ala Thr Ile Ser Gly Leu Lys Pro Gly
        50                  55                  60

Val Asp Tyr Thr Ile Thr Val Tyr Ala Val Thr Gly Ser Gly Glu Ser
65                  70                  75                  80

Pro Ala Ser Ser Thr Pro Ile Ser Ile Asn Tyr Arg Thr
                85                  90

<210> SEQ ID NO 116
<211> LENGTH: 116
<212> TYPE: PRT
<213> ORGANISM: Artificial Sequence
<220> FEATURE:
<223> OTHER INFORMATION: Synthetic: ADX_6727_H06

<400> SEQUENCE: 116

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
            35                  40                  45

Gly Pro Leu Tyr Ile Gln Gln Glu Phe Thr Val Pro Gly Ser Lys Ser
        50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Thr Pro
                85                  90                  95
```

Ile Ser Ile Asn Tyr Arg Thr Glu Ile Asp Lys Pro Ser Gln His His
                100                 105                 110

His His His His
        115

<210> SEQ ID NO 117
<211> LENGTH: 93
<212> TYPE: PRT
<213> ORGANISM: Artificial Sequence
<220> FEATURE:
<223> OTHER INFORMATION: Synthetic: ADX_6734_A02 (I43A/Y44E) core

<400> SEQUENCE: 117

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
                20                  25                  30

Gln Lys Tyr Ser Asp Leu Gly Pro Leu Tyr Ala Glu Gln Glu Phe Thr
            35                  40                  45

Val Pro Gly Ser Lys Ser Thr Ala Thr Ile Ser Gly Leu Lys Pro Gly
50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 118
<211> LENGTH: 116
<212> TYPE: PRT
<213> ORGANISM: Artificial Sequence
<220> FEATURE:
<223> OTHER INFORMATION: Synthetic: ADX_6734_A02

<400> SEQUENCE: 118

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Arg Glu Val Gln Lys Tyr Ser Asp Leu
            35                  40                  45

Gly Pro Leu Tyr Ala Glu Gln Glu Phe Thr Val Pro Gly Ser Lys Ser
        50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
                100                 105                 110

His His His His
        115

<210> SEQ ID NO 119
<211> LENGTH: 18
<212> TYPE: PRT
<213> ORGANISM: Artificial Sequence
<220> FEATURE:
<223> OTHER INFORMATION: Synthetic: ADX_6734_A02 CD loop

<400> SEQUENCE: 119

Gly Arg Glu Val Gln Lys Tyr Ser Asp Leu Gly Pro Leu Tyr Ala Glu

```
1               5                  10                 15

Gln Glu

<210> SEQ ID NO 120
<211> LENGTH: 18
<212> TYPE: PRT
<213> ORGANISM: Artificial Sequence
<220> FEATURE:
<223> OTHER INFORMATION: Synthetic: Linker

<400> SEQUENCE: 120

Pro Ser Thr Pro Pro Thr Pro Ser Pro Ser Thr Pro Pro Thr Pro Ser
1               5                  10                 15

Pro Ser

<210> SEQ ID NO 121
<211> LENGTH: 14
<212> TYPE: PRT
<213> ORGANISM: Artificial Sequence
<220> FEATURE:
<223> OTHER INFORMATION: Synthetic: Linker

<400> SEQUENCE: 121

Gly Ser Gly Ser Gly Ser Gly Ser Gly Ser Gly Ser Gly Ser
1               5                  10

<210> SEQ ID NO 122
<211> LENGTH: 13
<212> TYPE: PRT
<213> ORGANISM: Artificial Sequence
<220> FEATURE:
<223> OTHER INFORMATION: Synthetic: Linker

<400> SEQUENCE: 122

Gly Gly Ser Gly Ser Gly Ser Gly Ser Gly Ser Gly Ser
1               5                  10

<210> SEQ ID NO 123
<211> LENGTH: 16
<212> TYPE: PRT
<213> ORGANISM: Artificial Sequence
<220> FEATURE:
<223> OTHER INFORMATION: Synthetic: Linker

<400> SEQUENCE: 123

Gly Gly Ser Gly Ser Gly Ser Gly Ser Gly Ser Gly Ser Gly Ser Gly
1               5                  10                 15

<210> SEQ ID NO 124
<211> LENGTH: 15
<212> TYPE: PRT
<213> ORGANISM: Artificial Sequence
<220> FEATURE:
<223> OTHER INFORMATION: Synthetic: Linker

<400> SEQUENCE: 124

Gly Ser Glu Gly Ser Glu Gly Ser Glu Gly Ser Glu Gly Ser Glu
1               5                  10                 15

<210> SEQ ID NO 125
<211> LENGTH: 8
<212> TYPE: PRT
<213> ORGANISM: Artificial Sequence
<220> FEATURE:
<223> OTHER INFORMATION: Synthetic: Linker
```

```
<400> SEQUENCE: 125

Gly Gly Ser Glu Gly Gly Ser Glu
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic: Linker

<400> SEQUENCE: 126

Gly Ser Gly Ser Gly Ser Gly Ser
1               5

<210> SEQ ID NO 127
<211> LENGTH: 35
<212> TYPE: PRT
<213> ORGANISM: Artificial Sequence
<220> FEATURE:
<223> OTHER INFORMATION: Synthetic: Linker

<400> SEQUENCE: 127

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 128
<211> LENGTH: 25
<212> TYPE: PRT
<213> ORGANISM: Artificial Sequence
<220> FEATURE:
<223> OTHER INFORMATION: Synthetic: Linker

<400> SEQUENCE: 128

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 129
<211> LENGTH: 16
<212> TYPE: PRT
<213> ORGANISM: Artificial Sequence
<220> FEATURE:
<223> OTHER INFORMATION: Synthetic: Linker

<400> SEQUENCE: 129

Gly Gly Gly Gly Ser Gly Gly Gly Gly Ser Gly Gly Gly Gly Ser Gly
1               5                   10                  15

<210> SEQ ID NO 130
<211> LENGTH: 7
<212> TYPE: PRT
<213> ORGANISM: Artificial Sequence
<220> FEATURE:
<223> OTHER INFORMATION: Synthetic: Linker

<400> SEQUENCE: 130

Gly Pro Gly Pro Gly Pro Gly
1               5
```

```
<210> SEQ ID NO 131
<211> LENGTH: 11
<212> TYPE: PRT
<213> ORGANISM: Artificial Sequence
<220> FEATURE:
<223> OTHER INFORMATION: Synthetic: Linker

<400> SEQUENCE: 131

Gly Pro Gly Pro Gly Pro Gly Pro Gly Pro Gly
1               5                   10

<210> SEQ ID NO 132
<211> LENGTH: 6
<212> TYPE: PRT
<213> ORGANISM: Artificial Sequence
<220> FEATURE:
<223> OTHER INFORMATION: Synthetic: Linker

<400> SEQUENCE: 132

Pro Ala Pro Ala Pro Ala
1               5

<210> SEQ ID NO 133
<211> LENGTH: 12
<212> TYPE: PRT
<213> ORGANISM: Artificial Sequence
<220> FEATURE:
<223> OTHER INFORMATION: Synthetic: Linker

<400> SEQUENCE: 133

Pro Ala Pro Ala Pro Ala Pro Ala Pro Ala Pro Ala
1               5                   10

<210> SEQ ID NO 134
<211> LENGTH: 18
<212> TYPE: PRT
<213> ORGANISM: Artificial Sequence
<220> FEATURE:
<223> OTHER INFORMATION: Synthetic: Linker

<400> SEQUENCE: 134

Pro Ala Pro Ala Pro Ala Pro Ala Pro Ala Pro Ala Pro Ala Pro Ala
1               5                   10                  15

Pro Ala

<210> SEQ ID NO 135
<211> LENGTH: 10
<212> TYPE: PRT
<213> ORGANISM: Artificial Sequence
<220> FEATURE:
<223> OTHER INFORMATION: Synthetic: Linker

<400> SEQUENCE: 135

Pro Ser Pro Glu Pro Pro Thr Pro Glu Pro
1               5                   10

<210> SEQ ID NO 136
<211> LENGTH: 20
<212> TYPE: PRT
<213> ORGANISM: Artificial Sequence
<220> FEATURE:
<223> OTHER INFORMATION: Synthetic: Linker

<400> SEQUENCE: 136

Pro Ser Pro Glu Pro Pro Thr Pro Glu Pro Pro Ser Pro Glu Pro Pro
1               5                   10                  15
```

```
Thr Pro Glu Pro
         20

<210> SEQ ID NO 137
<211> LENGTH: 30
<212> TYPE: PRT
<213> ORGANISM: Artificial Sequence
<220> FEATURE:
<223> OTHER INFORMATION: Synthetic: Linker

<400> SEQUENCE: 137

Pro Ser Pro Glu Pro Pro Thr Pro Glu Pro Pro Ser Pro Glu Pro Pro
1               5                   10                  15

Thr Pro Glu Pro Pro Ser Pro Glu Pro Pro Thr Pro Glu Pro
            20                  25                  30

<210> SEQ ID NO 138
<211> LENGTH: 40
<212> TYPE: PRT
<213> ORGANISM: Artificial Sequence
<220> FEATURE:
<223> OTHER INFORMATION: Synthetic: Linker

<400> SEQUENCE: 138

Pro Ser Pro Glu Pro Pro Thr Pro Glu Pro Pro Ser Pro Glu Pro Pro
1               5                   10                  15

Thr Pro Glu Pro Pro Ser Pro Glu Pro Pro Thr Pro Glu Pro Pro Ser
            20                  25                  30

Pro Glu Pro Pro Thr Pro Glu Pro
            35                  40

<210> SEQ ID NO 139
<211> LENGTH: 6
<212> TYPE: PRT
<213> ORGANISM: Artificial Sequence
<220> FEATURE:
<223> OTHER INFORMATION: Synthetic: Linker

<400> SEQUENCE: 139

Glu Glu Glu Glu Asp Glu
1               5

<210> SEQ ID NO 140
<211> LENGTH: 11
<212> TYPE: PRT
<213> ORGANISM: Artificial Sequence
<220> FEATURE:
<223> OTHER INFORMATION: Synthetic: Linker

<400> SEQUENCE: 140

Glu Glu Glu Glu Asp Glu Glu Glu Glu Asp Glu
1               5                   10

<210> SEQ ID NO 141
<211> LENGTH: 21
<212> TYPE: PRT
<213> ORGANISM: Artificial Sequence
<220> FEATURE:
<223> OTHER INFORMATION: Synthetic: Linker

<400> SEQUENCE: 141

Glu Glu Glu Glu Asp Glu Glu Glu Glu Asp Glu Glu Glu Glu Asp Glu
1               5                   10                  15

Glu Glu Glu Asp Glu
```

<210> SEQ ID NO 142
<211> LENGTH: 31
<212> TYPE: PRT
<213> ORGANISM: Artificial Sequence
<220> FEATURE:
<223> OTHER INFORMATION: Synthetic: Linker

<400> SEQUENCE: 142

Glu Glu Glu Glu Asp Glu Glu Glu Glu Asp Glu Glu Glu Glu Asp Glu
1               5                   10                  15

Glu Glu Glu Asp Glu Glu Glu Glu Asp Glu Glu Glu Glu Asp Glu
            20                  25                  30

<210> SEQ ID NO 143
<211> LENGTH: 23
<212> TYPE: PRT
<213> ORGANISM: Artificial Sequence
<220> FEATURE:
<223> OTHER INFORMATION: Synthetic: Linker

<400> SEQUENCE: 143

Arg Gly Gly Glu Glu Lys Lys Lys Glu Lys Glu Lys Glu Glu Gln Glu
1               5                   10                  15

Glu Arg Glu Thr Lys Thr Pro
            20

<210> SEQ ID NO 144
<211> LENGTH: 100
<212> TYPE: PRT
<213> ORGANISM: Artificial Sequence
<220> FEATURE:
<223> OTHER INFORMATION: Synthetic: Linker
<220> FEATURE:
<221> NAME/KEY: misc_feature
<222> LOCATION: (1)..(100)
<223> OTHER INFORMATION: At least one PSPEPPTPEP and up to ten
      PSPEPPTPEP may be present

<400> SEQUENCE: 144

Pro Ser Pro Glu Pro Pro Thr Pro Glu Pro Ser Pro Glu Pro Pro
1               5                   10                  15

Thr Pro Glu Pro Pro Ser Pro Glu Pro Pro Thr Pro Glu Pro Pro Ser
            20                  25                  30

Pro Glu Pro Pro Thr Pro Glu Pro Pro Ser Pro Glu Pro Pro Thr Pro
        35                  40                  45

Glu Pro Pro Ser Pro Glu Pro Pro Thr Pro Glu Pro Pro Ser Pro Glu
    50                  55                  60

Pro Pro Thr Pro Glu Pro Pro Ser Pro Glu Pro Pro Thr Pro Glu Pro
65                  70                  75                  80

Pro Ser Pro Glu Pro Pro Thr Pro Glu Pro Pro Ser Pro Glu Pro Pro
                85                  90                  95

Thr Pro Glu Pro
            100

<210> SEQ ID NO 145
<211> LENGTH: 61
<212> TYPE: PRT
<213> ORGANISM: Artificial Sequence
<220> FEATURE:
<223> OTHER INFORMATION: Synthetic: Linker
<220> FEATURE:
<221> NAME/KEY: misc_feature

```
<222> LOCATION: (1)..(60)
<223> OTHER INFORMATION: At least one EEEEDE and up to ten EEEEDE may be
      present

<400> SEQUENCE: 145

Glu Glu Glu Glu Asp Glu Glu Glu Glu Asp Glu Glu Glu Glu
1               5                   10                  15

Asp Glu Glu Glu Glu Glu Asp Glu Glu Glu Glu Asp Glu Glu
                20                  25                  30

Glu Glu Asp Glu Glu Glu Glu Asp Glu Glu Glu Glu Asp Glu
            35                  40                  45

Glu Glu Glu Glu Asp Glu Glu Glu Glu Asp Glu Glu
    50                  55                  60

<210> SEQ ID NO 146
<211> LENGTH: 16
<212> TYPE: PRT
<213> ORGANISM: Artificial Sequence
<220> FEATURE:
<223> OTHER INFORMATION: Synthetic: Exemplary use of linker

<400> SEQUENCE: 146

Asn Tyr Arg Thr Pro Gly Pro Ser Pro Glu Pro Pro Thr Pro Glu Pro
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic: Exemplary use of linker

<400> SEQUENCE: 147

Pro Ser Pro Glu Pro Pro Thr Pro Glu Pro Gly Val Ser Asp Val
1               5                   10                  15

<210> SEQ ID NO 148
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 148

Glu Ile Glu Pro Lys Ser Ser
1               5

<210> SEQ ID NO 149
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 149

Glu Ile Asp Lys Pro Cys
1               5

<210> SEQ ID NO 150
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 150
```

```
Glu Ile Asp Lys Pro
1               5

<210> SEQ ID NO 151
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 151

Glu Ile Asp Lys Pro Ser
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic: C-terminal tail

<400> SEQUENCE: 152

Glu Ile Asp Lys Pro Ser Gln Leu Glu
1               5

<210> SEQ ID NO 153
<211> LENGTH: 12
<212> TYPE: PRT
<213> ORGANISM: Artificial Sequence
<220> FEATURE:
<223> OTHER INFORMATION: Synthetic: C-terminal tail

<400> SEQUENCE: 153

Glu Ile Glu Asp Glu Asp Glu Asp Glu Asp Glu Asp
1               5                   10

<210> SEQ ID NO 154
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 154

Glu Gly Ser Gly Ser
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic: C-terminal tail

<400> SEQUENCE: 155

Glu Ile Asp Lys Pro Cys Gln Leu Glu
1               5

<210> SEQ ID NO 156
<211> LENGTH: 13
<212> TYPE: PRT
<213> ORGANISM: Artificial Sequence
<220> FEATURE:
<223> OTHER INFORMATION: Synthetic: C-terminal tail

<400> SEQUENCE: 156
```

```
Glu Ile Asp Lys Pro Ser Gln His His His His His
1               5                   10
```

<210> SEQ ID NO 157
<211> LENGTH: 10
<212> TYPE: PRT
<213> ORGANISM: Artificial Sequence
<220> FEATURE:
<223> OTHER INFORMATION: Synthetic: C-terminal tail

<400> SEQUENCE: 157

```
Gly Ser Gly Cys His His His His His His
1               5                   10
```

<210> SEQ ID NO 158
<211> LENGTH: 11
<212> TYPE: PRT
<213> ORGANISM: Artificial Sequence
<220> FEATURE:
<223> OTHER INFORMATION: Synthetic: C-terminal tail

<400> SEQUENCE: 158

```
Glu Gly Ser Gly Cys His His His His His
1               5                   10
```

<210> SEQ ID NO 159
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 159

```
Pro Ile Asp Lys
1
```

<210> SEQ ID NO 160
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 160

```
Pro Ile Glu Lys
1
```

<210> SEQ ID NO 161
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 161

```
Pro Ile Asp Lys Pro
1               5
```

<210> SEQ ID NO 162
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 162

```
Pro Ile Glu Lys Pro
```

```
1               5

<210> SEQ ID NO 163
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 163

Pro Ile Asp Lys Pro Ser
1               5

<210> SEQ ID NO 164
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 164

Pro Ile Glu Lys Pro Ser
1               5

<210> SEQ ID NO 165
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 165

Pro Ile Asp Lys Pro Cys
1               5

<210> SEQ ID NO 166
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 166

Pro Ile Glu Lys Pro Cys
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 167

Pro Ile Asp Lys Pro Ser Gln
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 168

Pro Ile Glu Lys Pro Ser Gln
1               5
```

<210> SEQ ID NO 169
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 169

Pro Ile Asp Lys Pro Cys Gln
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 170

Pro Ile Glu Lys Pro Cys Gln
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 171

Pro His His His His His
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic: C-terminal tail

<400> SEQUENCE: 172

Pro Cys His His His His His
1               5

<210> SEQ ID NO 173
<211> LENGTH: 351
<212> TYPE: DNA
<213> ORGANISM: Artificial Sequence
<220> FEATURE:
<223> OTHER INFORMATION: Synthetic: 7016_A01 (nucleic acid sequence)

<400> SEQUENCE: 173
atgggagttt ctgatgtgcc gcgcgacctg gaagtggttg ctgccacccc caccagcctg      60
ctgatcagct gggatgcacc tgccgtcaca gtgcgatatt accgcatcac ttacggcagg     120
gaggttcaga agtactcgga cttgggtccg ttgtacatct accaagagtt cactgtgcct     180
gggagcaagt ccacagctac catcagcggc cttaaacctg cgttgattta ccatcact      240 gtgtatgctg tcactggctc tggagagagc cccgcaagca gcaagccaat ttccattaat     300
taccgcacag aaattgacaa accatcccag caccatcacc accaccactg a              351

FAST-OFF RATE SERUM ALBUMIN BINDING FIBRONECTIN TYPE III DOMAINS

RELATED APPLICATIONS

This application is a 35 U.S.C. 371 national stage filing of International Application No. PCT/US2016/053183, filed Sep. 22, 2016, which claims priority to U.S. Provisional Application No. 62/222,508, filed Sep. 23, 2015. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Mar. 15, 2018, is named MXI_545US_Sequence_Listing.txt and is 108,190 bytes in size.

BACKGROUND

Inadequate half-lives of therapeutics often necessitate their administration at high frequencies and/or higher doses, or the use of sustained release formulations, in order to maintain serum levels necessary for therapeutic effects. However, this is often associated with negative side effects. One strategy for overcoming inadequate half-lives is to fuse the therapeutic to a half-life-extending polypeptide. Yet, while the extension of half-life may be beneficial, an overly stabilized therapeutic may also lead to negative side effects. Accordingly, the ability to fine tune the half-lives of therapeutics can be beneficial. This application provides compounds that fine tune the serum half-lives of various therapeutics and methods for generating the same.

SUMMARY

The invention is based, at least in part, on the development of novel human serum albumin (HSA) binding fibronectin type III tenth ($^{10}$Fn3) domains which provide versatility in controlling the half-lives of fusion partners (e.g., therapeutic polypeptides).

In one aspect, provided herein is a polypeptide comprising a $^{10}$Fn3 domain, wherein the $^{10}$Fn3 domain binds to HSA with a $K_D$ of 1 µM or less and comprises AB, BC, CD, DE, EF, and FG loops, wherein the CD loop has 1, 2, or 3 amino acid substitutions, and the FG loop optionally has 1, 2, or 3 amino acid substitutions, relative to the CD and FG loops of a $^{10}$Fn3 domain comprising the amino acid sequence set forth in SEQ ID NO: 23, and wherein the serum half-life of a moiety (e.g., polypeptide) that is linked to the $^{10}$Fn3 domain is extended relative to that of the moiety that is not linked to the $^{10}$Fn3 domain.

In certain embodiments, the polypeptide binds to HSA with an off-rate (kd) that is greater than the kd of the $^{10}$Fn3 domain comprising the amino acid sequence set forth in SEQ ID NO: 23. In certain embodiments, the ratio of the off-rate of the polypeptide to the off-rate of the $^{10}$Fn3 domain comprising the amino acid sequence set forth in SEQ ID NO: 23 is at least about 3. In certain embodiments, the ratio is at least about 25. In certain embodiments, the ratio is at least about 25. In certain embodiments, the ratio is at least about 50.

In certain embodiments, the polypeptide binds to HSA with an on-rate (ka) that is within an order of magnitude (i.e., within 10-fold) of the ka of the $^{10}$Fn3 domain comprising the amino acid sequence set forth in SEQ ID NO: 23.

In certain embodiments, the CD loop has 1 or 2 amino acid substitutions relative to the corresponding CD loop of the $^{10}$Fn3 domain comprising the amino acid sequence set forth in SEQ ID NO: 23. In certain embodiments, the FG loop has 1 amino acid substitution relative to the FG loop of the $^{10}$Fn3 domain comprising the amino acid sequence set forth in SEQ ID NO: 23. In certain embodiments, the CD loop has 1 amino acid substitution and the FG loop has 1 substitution relative to the CD loop and FG loop of the $^{10}$Fn3 domain comprising the amino acid sequence set forth in SEQ ID NO: 23.

In certain embodiments, the CD loop of the $^{10}$Fn3 domain has 1 or 2 amino acid substitutions relative to the corresponding CD loop of the $^{10}$Fn3 domain comprising the amino acid sequence set forth in SEQ ID NO: 23, wherein the 1 or 2 substitutions are selected from the group consisting of:
  (i) the arginine (R) at position 2 of the CD loop (SEQ ID NO: 28) is substituted with an amino acid selected from D, E, A, Q, or N;
  (ii) the glutamine (Q) at position 5 of the CD loop (SEQ ID NO: 28) is substituted with D;
  (iii) the tyrosine (Y) at position 7 of the CD loop (SEQ ID NO: 28) is substituted with an amino acid selected from S or A;
  (iv) the leucine (L) at position 10 of the CD loop (SEQ ID NO: 28) is substituted with an amino acid selected from S, T, or A;
  (v) the leucine (L) at position 13 of the CD loop (SEQ ID NO: 28) is substituted with an amino acid selected from D, S, or A;
  (vi) the tyrosine (Y) at position 14 of the CD loop (SEQ ID NO: 28) is substituted with an amino acid selected from A or T;
  (vii) the isoleucine (I) at position 15 of the CD loop (SEQ ID NO: 28) is substituted with an amino acid selected from D, S, or A; and
  (viii) The tyrosine (Y) at position 16 of the CD loop (SEQ ID NO: 28) is substituted with an amino acid selected from Q, E, S, or A.

In certain embodiments, the $^{10}$Fn3 domain has 1 or 2 amino acid substitutions relative to the corresponding CD loop of the $^{10}$Fn3 domain comprising the amino acid sequence set forth in SEQ ID NO: 23, as described above, and/or the $^{10}$Fn3 domain has 1 amino acid substitution relative to the corresponding FG loop of the $^{10}$Fn3 domain comprising the amino acid sequence set forth in SEQ ID NO: 23. In certain embodiments, the lysine (K) at position 12 of the FG loop (SEQ ID NO: 29) is substituted with an amino acid selected from A, T, or S.

In certain embodiments, the polypeptide comprises an amino acid sequence at least 80%, 85%, 90%, 95%, 96%, 97%, 98%, 99%, or 100% identical to the non-CD loop regions of any one of SEQ ID NOs: 23-27, 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118, optionally with the proviso that the sequence is not that of ADX_2629_E06. In certain embodiments, the polypeptide comprises an amino acid sequence that is at least 80%, 85%, 90%, 95%, 96%, 97%, 98%, 99%, or 100% identical to any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118, optionally with the proviso that the sequence is not that of ADX_2629_E06.

In certain embodiments, the $^{10}$Fn3 domain binds to domain I-II of HSA.

In certain embodiments, the polypeptides described herein further comprise a heterologous protein, such as a therapeutic moiety (e.g., a $^{10}$Fn3 domain).

In certain aspects, provided herein is a composition (e.g., a pharmaceutical composition) comprising a polypeptide comprising any of the HSA binding $^{10}$Fn3 domains or fusion polypeptides comprising such, as described herein, and a carrier (e.g., a pharmaceutically acceptable carrier).

In certain aspects, provided herein is an isolated nucleic acid encoding any one of the HSA binding $^{10}$Fn3 domains (e.g., an isolated nucleic acid encoding any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118) or fusion polypeptides comprising such, as described herein, expression vectors comprising the same, and cells comprising the nucleic acid molecules.

In certain aspects, provided herein is a method of producing the HSA binding $^{10}$Fn3 domains or fusion polypeptides comprising such, as described herein, comprising culturing the cell comprising the nucleic acid molecules encoding the same under conditions suitable for expressing the $^{10}$Fn3 domains or fusion polypeptides, and purifying the same.

In certain aspects, provided herein is a method of enhancing the half-life of a moiety, comprising linking to the moiety a HSA binding $^{10}$Fn3 domain described herein.

DETAILED DESCRIPTION

Definitions

Figure 1:
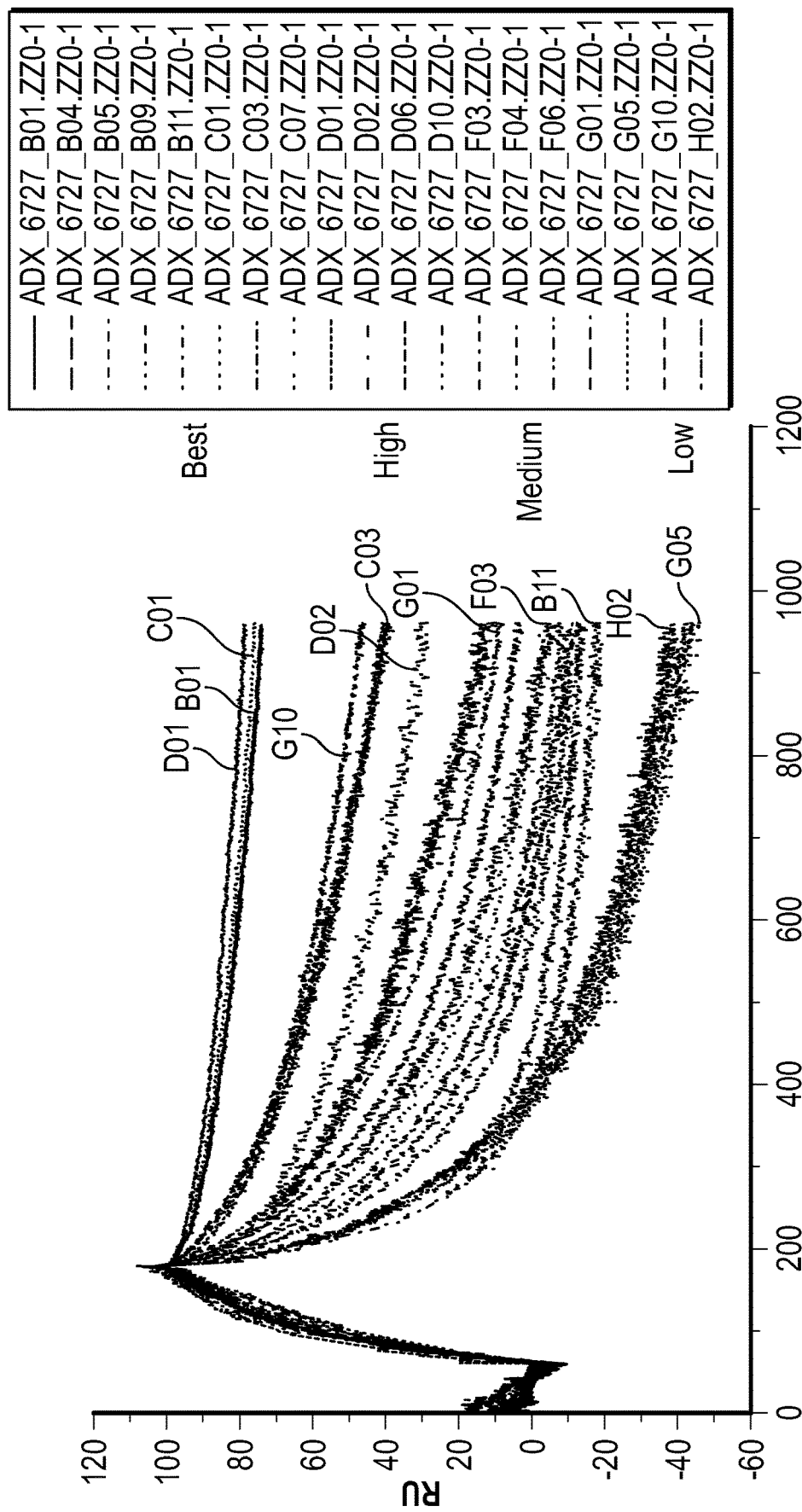
FIGS. 1 and 2 are SPR sensograms of Adnectins binding to HSA, normalized at start of dissociation phase to illustrate differences in off-rates of binding.

Unless defined otherwise, all technical and scientific terms used herein have the same meaning as commonly understood by the skilled artisan. Although any methods and compositions similar or equivalent to those described herein can be used in practice or testing of the present invention, the preferred methods and compositions are described herein.

A "polypeptide," as used herein, refers to any sequence of two or more amino acids, regardless of length, post-translation modification, or function. "Polypeptide" and "peptide," are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

A "polypeptide chain", as used herein, refers to a polypeptide wherein each of the domains thereof is joined to other domain(s) by peptide bond(s), as opposed to non-covalent interactions or disulfide bonds.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or nonreducing condition using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

As used herein, a "$^{10}$Fn3 domain" or "$^{10}$Fn3 moiety" or "$^{10}$Fn3 molecule" refers to wild-type $^{10}$Fn3 and biologically active variants thereof, e.g., biologically active variants that specifically bind to a target, such as a target protein. A wild-type human $^{10}$Fn3 domain may comprise the amino acid sequence set forth in SEQ ID NO: 1. Biologically active variants of a wild-type human $^{10}$Fn3 domain include $^{10}$Fn3 domains that comprise at least, at most or about 1, 2, 3, 4, 5, 6, 7, 8, 9, 10, 11, 12, 13, 14, 15, 16, 17, 18, 19, 20, 21, 22, 23, 24, 25, 30, 35, 40 or 45 amino acid changes, i.e., substitutions, additions or deletions, relative to a $^{10}$Fn3 domain comprising SEQ ID NO: 1.

A "region" of a $^{10}$Fn3 domain as used herein refers to either a loop (AB, BC, CD, DE, EF and FG), a β-strand (A, B, C, D, E, F and G), the N-terminus (corresponding to amino acid residues 1-8 of SEQ ID NO: 1), or the C-terminus (corresponding to amino acid residues 93-94 of SEQ ID NO: 1) of the human $^{10}$Fn3 domain.

A "north pole loop" refers to any one of the BC, DE and FG loops of a fibronectin human fibronectin type 3 tenth ($^{10}$Fn3) domain.

A "south pole loop" refers to any one of the AB, CD and EF loops of a fibronectin human fibronectin type 3 tenth ($^{10}$Fn3) domain.

As used herein, "Adnectin" refers to a $^{10}$Fn3 domain that is modified to specifically bind to a target of interest.

A "scaffold region" refers to any non-loop region of a human $^{10}$Fn3 domain. The scaffold region includes the A, B, C, D, E, F and G β-strands as well as the N-terminal region (amino acids corresponding to residues 1-8 of SEQ ID NO: 1) and the C-terminal region (amino acids corresponding to residues 93-94 of SEQ ID NO: 1 and optionally comprising the 7 amino acids constituting the natural linker between the $10^{th}$ and the $11^{th}$ repeat of the Fn3 domain in human fibronectin).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The terms "specifically binds," "specific binding," "selective binding," and "selectively binds," as used interchangeably herein refers to an Adnectin that exhibits affinity for HSA, but does not significantly bind (e.g., less than about 10% binding) to a different polypeptide as measured by a technique available in the art such as, but not limited to, Scatchard analysis and/or competitive binding assays (e.g., competition ELISA, BIACORE assay). The term is also applicable where e.g., a binding domain of an Adnectin of the invention is specific for HSA.

The "half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques will be clear to the person skilled in the art, and may, for example, generally involve the steps of administering a suitable dose of a polypeptide to a primate; collecting blood samples or other samples from said primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., Chemical Stability of Pharmaceuticals: A Handbook for Pharmacists (1986); Peters et al, Pharmacokinetic analysis: A Practical Approach (1996); and "Pharmacokinetics", M Gibaldi & D Perron, published by Marcel Dekker, 2nd Rev. edition (1982).

Half-life can be expressed using parameters such as the $t_{1/2}$-alpha, $t_{1/2}$-beta and the area under the curve (AUC). In the present specification, an "increase in half-life" refers to an increase in any one of these parameters, any two of these parameters, or in all three these parameters. In certain embodiments, an increase in half-life refers to an increase in the t½-beta, either with or without an increase in the $t_{1/2}$-alpha and/or the AUC or both.

The term "$K_D$," as used herein in the context of an Adnectin binding to a protein, refers to the dissociation equilibrium constant of a particular Adnectin-protein interaction or the affinity of an Adnectin for a protein (e.g., HSA), as measured using a surface plasmon resonance assay or a cell binding assay. A "desired $K_D$," as used herein, refers to a $K_D$ of an Adnectin that is sufficient for the purposes contemplated. For example, a desired $K_D$ may refer to the $K_D$ of an Adnectin required to elicit a functional effect in an in vitro assay, e.g., a cell-based luciferase assay.

The terms "$k_{ass}$", "$k_{on}$", and "ka" are used interchangeably herein, and refer to the association rate constant for the association of an Adnectin into the Adnectin/protein complex.

The terms "$k_{diss}$", "$k_{off}$", and "kd" are used interchangeably herein, and refer to the dissociation rate constant for the dissociation of an Adnectin from the Adnectin/protein complex.

The term "$IC_{50}$", as used herein, refers to the concentration of an Adnectin that inhibits a response, either in an in vitro or an in vivo assay, to a level that is 50% of the maximal inhibitory response, i.e., halfway between the maximal inhibitory response and the untreated response.

The term "therapeutically effective amount" refers to an amount of a drug effective to treat a disease or disorder in a mammal and/or relieve to some extent one or more of the symptoms associated with the disorder.

As used herein, "preventing" a disease or disorder refers to reducing the probability of occurrence of a disease-state in a statistical sample relative to an untreated control sample, or delaying the onset or reducing the severity of one or more symptoms of the disease or disorder relative to the untreated control sample. Patients may be selected for preventative therapy based on factors that are known to increase risk of suffering a clinical disease state compared to the general population.

The term "treating" as used herein includes (a) inhibiting the disease-state, i.e., arresting its development; and/or (b) relieving the disease-state, i.e., causing regression of the disease state once it has been established.

As used herein, the term "about" means ±10% of the recited value.

Overview

The novel fibronectin-based scaffold polypeptides described herein bind to HSA and can be coupled to additional molecule(s), such as other ¹⁰Fn3 domains that bind to different targets, or polypeptides for which increased half-life is beneficial.

A. Human Serum Albumin Binding ¹⁰Fn3 Domains

Fn3 refers to a type III domain from fibronectin. An Fn3 domain is small, monomeric, soluble, and stable. It lacks disulfide bonds and, therefore, is stable under reducing conditions. The overall structure of Fn3 resembles the immunoglobulin fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). Any or all of loops AB, BC, CD, DE, EF and FG may participate in ligand binding. There are at least 15 different Fn3 modules in human Fibronectin, and while the sequence homology between the modules is low, they all share a high similarity in tertiary structure.

In certain embodiments, the Fn3 domain is an Fn3 domain derived from the wild-type tenth module of the human fibronectin type III domain (¹⁰Fn3):

```
                                              (SEQ ID NO: 1)
VSDVPRDLEVVAATPTSLLISWDAPAVTVRYYRITYGETGGNSPVQEFTV

PGSKSTATISGLKPGVDYTITVYAVTGRGDSPASSKPISINYRT
(AB, CD, and EF loops are underlined, and BC, DE,
and FG loops are bolded).
```

In certain embodiments, the non-ligand binding sequences of ¹⁰Fn3 may be altered provided that the ¹⁰Fn3 retains ligand binding function and/or structural stability. A variety of mutant ¹⁰Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant ¹⁰Fn3 at neutral pH as compared to the wild-type form (see, e.g., PCT Publication No. WO 02/04523). A variety of additional alterations in the ¹⁰Fn3 scaffold that are either beneficial or neutral have been disclosed. See, for example, Batori et al., *Protein Eng* 2002; 15:1015-20; Koide et al., *Biochemistry,* 2001; 40:10326-33.

Both variant and wild-type ¹⁰Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO: 1, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 75-87. Much of the variability will generally occur in one or more of the loops. However, it should be understood that not every residue within a loop region needs to be modified in order to achieve a ¹⁰Fn3 binding domain having strong affinity for a desired target. In some embodiments, only residues in a loop, e.g., the CD loop are modified to produce high affinity target binding ¹⁰Fn3 domains.

Each of the beta or beta-like strands of a ¹⁰Fn3 polypeptide may consist essentially of an amino acid sequence that is at least 80%, 85%, 90%, 95% or 100% identical to the sequence of a corresponding beta or beta-like strand of any one of SEQ ID NOs: 1, 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118, provided that such variation does not disrupt the stability of the polypeptide in physiological conditions.

Additionally, insertions and deletions in the loop regions may also be made while still producing HSA binding ¹⁰Fn3 binding domains. Accordingly, in some embodiments, one or more loops selected from AB, BC, CD, DE, EF and FG may be extended or shortened in length relative to the corresponding loop in wild-type human ¹⁰Fn3. In any given polypeptide, one or more loops may be extended in length, one or more loops may be reduced in length, or combinations thereof. In certain embodiments, the length of a given loop may be extended by 2-25, 2-20, 2-15, 2-10, 2-5, 5-25, 5-20, 5-15, 5-10, 10-25, 10-20, or 10-15 amino acids. In certain embodiments, the length of a given loop may be reduced by 1-15, 1-11, 1-10, 1-5, 1-3, 1-2, 2-10, or 2-5 amino acids.

In certain embodiments, provided herein are polypeptides comprising a ¹⁰Fn3 domain that specifically binds to HSA with a $K_D$ or 1 µM or less, wherein the ¹⁰Fn3 domain comprises AB, BC, CD, DE, and FG loops, and has at least one loop selected from CD and FG loops with an altered amino acid sequence relative to the sequence of the corresponding loop of the human ¹⁰Fn3 domain of SEQ ID NO: 1 or HSA binding ¹⁰Fn3 domain of SEQ ID NO: 23. In some embodiments, the CD and FG loops are altered. In certain embodiments, only the CD loop is altered. In certain embodiments, only the FG loop is altered. In certain embodiments, one or more specific scaffold alterations are combined with one or more loop alterations. By "altered" is meant one or more amino acid sequence alterations relative to a template sequence (i.e., the corresponding wild-type human fibronectin domain or ¹⁰Fn3 domain set forth in SEQ ID NO: 23) and includes amino acid additions, deletions, and substitutions.

In certain embodiments, the ¹⁰Fn3 domain has a combination of north and south pole loop alterations. For example, one or more of loops CD and FG, in combination with one or more of loops AB, BC, DE, and EF, can be altered relative to the corresponding loops of the human ¹⁰Fn3 domain of SEQ ID NO: 1 or the HSA binding ¹⁰Fn3 domain of SEQ ID NO: 23.

In certain embodiments, the polypeptide comprises a ¹⁰Fn3 domain that comprises an amino acid sequence at least 80, 85, 90, 95, 98, 99, or 100% identical to the non-loop regions and/or non-modified loop regions of any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118, wherein at least one loop selected from AB, BC, CD, DE, EF, or FG is altered. For example, in certain embodiments, the AB loop may have up to 4 amino acid substitutions, up to 10 amino acid insertions, up to 3 amino acid deletions, or a combination thereof; the BC loop may have up to 9 amino acid substitutions, up to 4 amino acid insertions, up to 3 amino acid deletions, or a combination thereof; the CD loop may have up to 6 amino acid substitutions, up to 10 amino acid insertions, up to 4 amino acid deletions, or a combination thereof; the DE loop may have up to 6 amino acid substitutions, up to 10 amino acid insertions, up to 4 amino acid deletions, or a combination thereof; the EF loop may have up to 5 amino acid substations, up to 10 amino acid insertions, up to 3 amino acid deletions, or a combination thereof; and/or the FG loop may have up to 12 amino acid substitutions, up to 11 amino acid deletions, up to 25 amino acid insertions, or a combination thereof, relative to the corresponding AB, BC, CD, DE, EF, and/or FG loops of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118.

In some embodiments, one or more residues of the integrin-binding motif "arginine-glycine-aspartic acid" (RGD) (amino acids 78-80 of SEQ ID NO: 1) may be substituted so as to disrupt integrin binding. In some embodiments, the FG loop of the polypeptides provided herein does not contain an RGD integrin binding site. In certain embodiments, the RGD sequence is replaced by a polar amino acid-neutral amino acid-acidic amino acid sequence (in the N-terminal to C-terminal direction). In certain embodiments, the RGD sequence is replaced with SGE. In yet certain embodiments, the RGD sequence is replaced with RGE.

In certain embodiments, the fibronectin based scaffold protein comprises a $^{10}$Fn3 domain that is defined generally by following the sequence:
VSDVPRDLEVVAA(X)$_u$LLISW(X)$_v$YRITY(X)$_w$FTV (X)$_x$ATISGL(X)$_y$YTITVYA(X)$_z$ISI NYRT (SEQ ID NO: 2)

In SEQ ID NO: 2, the AB loop is represented by (X)$_u$, the BC loop is represented by (X)$_v$, the CD loop is represented by (X)$_w$, the DE loop is represented by (X)$_x$, the EF loop is represented by (X)$_y$, and the FG loop is represented by X$_z$. X represents any amino acid and the subscript following the X represents an integer of the number of amino acids. In particular, u, v, w, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. The sequences of the beta strands (underlined) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 2. In certain embodiments, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 2. In certain embodiments, the hydrophobic core amino acid residues (bolded residues in SEQ ID NO: 2 above) are fixed, and any substitutions, conservative substitutions, deletions or additions occur at residues other than the hydrophobic core amino acid residues. In some embodiments, the hydrophobic core residues of the polypeptides provided herein have not been modified relative to the wild-type human $^{10}$Fn3 domain (SEQ ID NO: 1).

In certain aspects, the application provides $^{10}$Fn3 domains with south pole and/or north pole modifications that bind specifically to HSA to prolong the $t_{1/2}$ of a moiety that is linked to the $^{10}$Fn3 domain.

HSA has a serum concentration of 600 µM and a $t_{1/2}$ of 19 days in humans. The extended $t_{1/2}$ of HSA has been attributed, in part, to its recycling via the neonatal Fc receptor (FcRn). HSA binds FcRn in a pH-dependent manner after endosomal uptake into endothelial cells; this interaction recycles HSA back into the bloodstream, thereby shunting it away from lysosomal degradation. FcRn is widely expressed and the recycling pathway is thought to be constitutive. In the majority of cell types, most FcRn resides in the intracellular sorting endosome. HSA is readily internalized by a nonspecific mechanism of fluid-phase pinocytosis and rescued from degradation in the lysosome by FcRn. At the acidic pH found in the endosome, HSA's affinity for FcRn increases (5 µM at pH 6.0). Once bound to FcRn, HSA is shunted away from the lysosomal degradation pathway, transcytosed to and released at the cell surface.

North pole-based HSA binding Adnectins are referred to as "first generation" serum albumin binding Adnectins, and are described in, e.g., WO2011140086. In order to improve upon first generation north pole-based serum albumin binding Adnectins (SABAs), of which some did not bind to mouse or rat serum albumin, did not have high affinity for serum albumins across species, and were not always compatible in a multivalent $^{10}$Fn3-based platform, second generation south pole-based HSA binding Adnectins (PKE2 Adnectins) with modified south pole loops were developed (see PCT/US15/21535, which is specifically incorporated by reference herein in its entirety). One such Adnectin is ADX_7016_A01 (a second generation PKE2 Adnectin), which binds to domain I-II of HSA and has the following core sequence:

```
EVVAATPTSLLISWDAPAVTVRYYRITYGREVQKYSDLGPLYIYQEFTVP

GSKSTATISGLKPGVDYTITVYAVTGSGESPASSKPISINYRT
(SEQ ID NO: 23; the CD and FG loops are underlined)
```

ADX_7016_A01 has low immunogenicity and binds to HSA with a $K_D$ of about 3-6 nM. A fusion polypeptide comprising a heterologous $^{10}$Fn3 domain fused to ADX_7016_A01 has a half-life of about 82 hours in mice. While ADX_7016_A01 substantially extends the half-life of fusion partners, certain situations may call for the fusion partner to have a shorter half-life than that conferred by ADX_7016_A01.

Thus, provided herein are polypeptides comprising a $^{10}$Fn3 domain which binds to HSA, wherein the CD and/or FG loop of the $^{10}$Fn3 domain has 1, 2, or 3 amino acid substitutions, and the FG loop optionally 1, 2, or 3 amino acid substitutions relative to the CD and FG loops of a $^{10}$Fn3 domain comprising the amino acid sequence set forth in SEQ ID NO: 23, wherein the serum half-life of a moiety (e.g., polypeptide) that is linked to the $^{10}$Fn3 domain is extended relative to that of the moiety that is not linked to the $^{10}$Fn3 domain.

In certain embodiments, the CD loop has 2 amino acid substitutions relative to the corresponding CD loop of the $^{10}$Fn3 domain comprising the amino acid sequence set forth in SEQ ID NO: 23.

In certain embodiments, the CD loop has 1 amino acid substitution relative to the CD loop of the $^{10}$Fn3 domain comprising the amino acid sequence set forth in SEQ ID NO: 23.

In certain embodiments, the FG loop has 1 amino acid substitution relative to the FG loop of the $^{10}$Fn3 domain comprising the amino acid sequence set forth in SEQ ID NO: 23.

In certain embodiments, the CD loop has 1 amino acid substitution and the FG loop has 1 substitution relative to the CD loop and FG loop of the $^{10}$Fn3 domain comprising the amino acid sequence set forth in SEQ ID NO: 23.

In certain embodiments, the polypeptide binds to HSA with an off-rate (kd) that is greater than the kd of the $^{10}$Fn3 domain comprising the amino acid sequence set forth in SEQ ID NO: 23.

Polypeptides comprising a $^{10}$Fn3 domain with an off-rate (kd) that is greater than the kd of the $^{10}$Fn3 domain comprising the amino acid sequence set forth in SEQ ID NO: 23 are herein referred to as "PKE3" Adnectins.

Accordingly, provided herein are polypeptides comprising a $^{10}$Fn3 domain that binds to HSA with a $K_D$ or 1 μM or less, wherein the CD and/or FG loop of the $^{10}$Fn3 domain has 1, 2, or 3 amino acid substitutions, and the FG loop optionally 1, 2, or 3 amino acid substitutions relative to the CD and FG loops of a $^{10}$Fn3 domain comprising the amino acid sequence set forth in SEQ ID NO: 23, wherein the $^{10}$Fn3 domain binds to HSA with an off-rate (kd) that is greater than the kd of the $^{10}$Fn3 domain comprising the amino acid sequence set forth in SEQ ID NO: 23, and wherein the serum half-life of the polypeptide is extended relative to the polypeptide which lacks the $^{10}$Fn3 domain.

In certain embodiments, the ratio of the off-rate of the $^{10}$Fn3 domain to the off-rate of the $^{10}$Fn3 domain comprising the amino acid sequence set forth in SEQ ID NO: 23 is at least about 2, such as at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 75, at least about 100 or higher. In certain embodiments, the ratio is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60. In certain embodiments, the ratio is 1.0, 1.1, 1.2, 3.3, 3.9, 4.0, 4.1, 4.8, 5.0, 5.6, 6.5, 6.6, 8, 11, 14, 17, 20, 23, 28, 28.9, 30.3, 32.0, 34.0, 34.3, 37.3, 50.0, 52, 52.7, 53.0, 56.0, or 79.4. In certain embodiments, the ratio is in the range of 2-100, 2-75, 2-50, 2-45, 2-40, 2-35, 2-30, 2-25, 2-20, 2-15, 2-10, 2-5, 5-100, 5-75, 5-50, 5-45, 5-40, 5-35, 5-30, 5-25, 5-20, 5-15, 5-10, 10-100, 10-75, 10-50, 10-45, 10-40, 10-35, 10-30, 10-25, 10-20, 10-15, 20-100, 20-75, 20-50, 20-45, 20-40, 20-35, 20-30, 20-25, 30-100, 30-75, 30-50, 30-45, 30-40, 30-35, 40-100, 40-75, 40-50, 40-45, 50-100, 50-75, 60-100, 60-75, 70-100, 70-75, 80-100, 80-90, 90-100, 3-4, 3-5, 3-6, 3-7, 25-40, 30-40, 50-55, 75-85, 1-80, 1-70, 1-60, 1-50, 1-40, 1-30, 1-20, 1-10, or 1-5.

In certain embodiments, the off-rate of a $^{10}$Fn3 domain binding to HSA is at least $2.5\times10^{-4}$ s$^{-1}$; $2.5\times10^{-4}$ s$^{-1}$; $3\times10^{-4}$ s$^{-1}$; $5\times10^{-4}$ s$^{-1}$; $10^{-3}$ s$^{-1}$; $3\times10^{-3}$ s$^{-1}$; $5\times10^{-3}$ s$^{-1}$; $7\times10^{-3}$ s$^{-1}$; $10^{-2}$ s$^{-1}$; $3\times10^{-2}$ s$^{-1}$; or $5\times10^{-2}$ s$^{-1}$. In certain embodiments, the off-rate of a $^{10}$Fn3 domain binding to HSA is in the range of $2.5\times10^{-4}$ s$^{-1}$ to $5\times10^{-4}$ s$^{-1}$; $3\times10^{-4}$ s$^{-1}$ to $10\times10^{-4}$ s$^{-1}$; $5\times10^{-4}$ s$^{-1}$ to $10\times10^{-4}$ s$^{-1}$; $7\times10^{-4}$ s$^{-1}$ to $10\times10^{-4}$ s$^{-1}$; $3\times10^{-4}$ to $3\times10^{-3}$ s$^{-1}$; $10^{-3}$ s$^{-1}$ to $10^{-2}$ s$^{-1}$; or $3\times10^{-4}$ s$^{-1}$ to $10^{-3}$ s$^{-1}$.

In certain embodiments, the polypeptide binds to HSA with an on-rate (ka) that is within about an order of magnitude (i.e., within about 10-fold) of the ka of the $^{10}$Fn3 domain comprising the amino acid sequence set forth in SEQ ID NO: 23.

Accordingly, provided herein are polypeptides comprising a $^{10}$Fn3 domain that binds to HSA with a $K_D$ or 1 μM or less, wherein the CD and/or FG loop of the $^{10}$Fn3 domain has 1, 2, or 3 amino acid substitutions, and the FG loop optionally 1, 2, or 3 amino acid substitutions relative to the CD and FG loops of a $^{10}$Fn3 domain comprising the amino acid sequence set forth in SEQ ID NO: 23, wherein the polypeptide binds to HSA with an off-rate (kd) that is greater than the kd of the $^{10}$Fn3 domain comprising the amino acid sequence set forth in SEQ ID NO: 23, wherein the polypeptide binds to HSA with an on-rate (ka) that is within about an order of magnitude (i.e., within about 10-fold) of the ka of the $^{10}$Fn3 domain comprising the amino acid sequence set forth in SEQ ID NO: 23, and wherein the serum half-life of a moiety (e.g., polypeptide) that is linked to the $^{10}$Fn3 domain is extended relative to that of the moiety that is not linked to the $^{10}$Fn3 domain.

In certain embodiments, the CD loop of the $^{10}$Fn3 domain has 2 amino acid substitutions relative to the corresponding CD loop of the $^{10}$Fn3 domain comprising the amino acid sequence set forth in SEQ ID NO: 23.

In certain embodiments, the CD loop of the $^{10}$Fn3 domain has 2 amino acid substitutions relative to the corresponding CD loop of the $^{10}$Fn3 domain comprising the amino acid sequence set forth in SEQ ID NO: 23, wherein the 2 amino acid substitutions are selected from the group consisting of:

(i) the arginine (R) at position 2 of the CD loop (SEQ ID NO: 28) is substituted with an amino acid selected from D, E, A, Q, or N;

(ii) the glutamine (Q) at position 5 of the CD loop (SEQ ID NO: 28) is substituted with D;

(iii) the tyrosine (Y) at position 7 of the CD loop (SEQ ID NO: 28) is substituted with an amino acid selected from S or A;

(iv) the leucine (L) at position 10 of the CD loop (SEQ ID NO: 28) is substituted with an amino acid selected from S, T, or A;

(v) the leucine (L) at position 13 of the CD loop (SEQ ID NO: 28) is substituted with an amino acid selected from D, S, or A;

(vi) the tyrosine (Y) at position 14 of the CD loop (SEQ ID NO: 28) is substituted with an amino acid selected from A or T;

(vii) the isoleucine (I) at position 15 of the CD loop (SEQ ID NO: 28) is substituted with an amino acid selected from D, S, or A; and (viii) The tyrosine (Y) at position 16 of the CD loop (SEQ ID NO: 28) is substituted with an amino acid selected from Q, E, S, or A.

In certain embodiments, the CD loop of the $^{10}$Fn3 domain has 1 amino acid substitution relative to the corresponding CD loop of the $^{10}$Fn3 domain comprising the amino acid sequence set forth in SEQ ID NO: 23.

In certain embodiments, the CD loop of the $^{10}$Fn3 domain has 1 amino acid substitution relative to the corresponding CD loop of the $^{10}$Fn3 domain comprising the amino acid sequence set forth in SEQ ID NO: 23, wherein the 1 amino acid substitution is selected from the group consisting of:

(i) the arginine (R) at position 2 of the CD loop (SEQ ID NO: 28) is substituted with an amino acid selected from D, E, A, Q, or N;

(ii) the glutamine (Q) at position 5 of the CD loop (SEQ ID NO: 28) is substituted with D;

(iii) the tyrosine (Y) at position 7 of the CD loop (SEQ ID NO: 28) is substituted with an amino acid selected from S or A;

(iv) the leucine (L) at position 10 of the CD loop (SEQ ID NO: 28) is substituted with an amino acid selected from S, T, or A;

(v) the leucine (L) at position 13 of the CD loop (SEQ ID NO: 28) is substituted with an amino acid selected from D, S, or A;
(vi) the tyrosine (Y) at position 14 of the CD loop (SEQ ID NO: 28) is substituted with an amino acid selected from A or T;
(vii) the isoleucine (I) at position 15 of the CD loop (SEQ ID NO: 28) is substituted with an amino acid selected from D, S, or A; and
(viii) The tyrosine (Y) at position 16 of the CD loop (SEQ ID NO: 28) is substituted with an amino acid selected from Q, E, S, or A.

In certain embodiments, the FG loop of the $^{10}$Fn3 domain has 1 amino acid substitution relative to the FG loop of the $^{10}$Fn3 domain comprising the amino acid sequence set forth in SEQ ID NO: 23.

In certain embodiments, the FG loop of the $^{10}$Fn3 domain has 1 amino acid substitution relative to the FG loop of the $^{10}$Fn3 domain comprising the amino acid sequence set forth in SEQ ID NO: 23, wherein the lysine (K) at position 12 of the FG loop (SEQ ID NO: 29) is substituted with an amino acid selected from A, T, or S.

In certain embodiments, the CD loop of the $^{10}$Fn3 domain has 1 amino acid substitution and the FG loop has 1 substitution relative to the CD loop and FG loop of the $^{10}$Fn3 domain comprising the amino acid sequence set forth in SEQ ID NO: 23.

In certain embodiments, the CD loop of the $^{10}$Fn3 domain has 1 amino acid substitution and the FG loop has 1 substitution relative to the CD loop and FG loop of the $^{10}$Fn3 domain comprising the amino acid sequence set forth in SEQ ID NO: 23, wherein
  a) the 1 amino acid substitution in the CD loop selected from the group consisting of (i) the arginine (R) at position 2 of the CD loop (SEQ ID NO: 28) is substituted with an amino acid selected from D, E, A, Q, or N;
    (ii) the glutamine (Q) at position 5 of the CD loop (SEQ ID NO: 28) is substituted with D;
    (iii) the tyrosine (Y) at position 7 of the CD loop (SEQ ID NO: 28) is substituted with an amino acid selected from S or A;
    (iv) the leucine (L) at position 10 of the CD loop (SEQ ID NO: 28) is substituted with an amino acid selected from S, T, or A;
    (v) the leucine (L) at position 13 of the CD loop (SEQ ID NO: 28) is substituted with an amino acid selected from D, S, or A;
    (vi) the tyrosine (Y) at position 14 of the CD loop (SEQ ID NO: 28) is substituted with an amino acid selected from A or T;
    (vii) the isoleucine (I) at position 15 of the CD loop (SEQ ID NO: 28) is substituted with an amino acid selected from D, S, or A; and
    (viii) The tyrosine (Y) at position 16 of the CD loop (SEQ ID NO: 28) is substituted with an amino acid selected from Q, E, S, or A; and
  b) the lysine at position 12 of the FG loop (SEQ ID NO: 29) is substituted with an amino acid selected from A, T, or S.

In certain embodiments, the HSA binding $^{10}$Fn3 domains comprises a sequence having at least 40%, 50%, 60%, 70%, 75%, 80%, 85%, 90%, 95%, 96%, 97%, 98%, or 99% identity to the $^{10}$Fn3 domain comprising the amino acid sequence set forth in any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118, or comprise at most 1, 2, 3, 1-2, or 1-3 amino acid difference (i.e., substitution, e.g., deletion, addition or conservative substitution), such as one or more of the amino acid substitutions described herein. In certain embodiments, the HSA binding molecules comprise an amino acid sequence at least 80%, 85%, 90%, 95%, 98%, 99% or 100% identical to the non-CD loop region of SEQ ID NOs: 23-27, 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118.

In a certain embodiments, the CD loop of the HSA binding $^{10}$Fn3 domains described herein comprises an amino acid sequence selected from the group consisting of:

```
                             (SEQ ID NO: 28)
GREVQKYSDLGPLYIYQE,
                             (SEQ ID NO: 35)
GREVQKYSDLGPLYISQE,
                             (SEQ ID NO: 41)
GREVQKYSDTGPLYIYQE,
                             (SEQ ID NO: 47)
GREVQKYSDLGPLYIQQE,
                             (SEQ ID NO: 59)
GREVQKSSDLGPLYIYQE,
                             (SEQ ID NO: 64)
GAEVQKYSDLGPLYIYQE,
                             (SEQ ID NO: 69)
GNEVQKYSDLGPLYIYQE,
                             (SEQ ID NO: 72)
GREVQKYSDLGPAYIYQE,
                             (SEQ ID NO: 77)
GREVQKYSDLGPLYAYQE,
                             (SEQ ID NO: 80)
GREVQKYSDLGPLYIAQE,
                             (SEQ ID NO: 85)
GREVQKYSDLGPLYSYQE,
                             (SEQ ID NO: 88)
GREVDKYSDLGPLYIYQE,
                             (SEQ ID NO: 99)
GREVQKASDLGPLYIYQE,
                             (SEQ ID NO: 110)
GREVQKYSDLGPSYIYQE,
and
                             (SEQ ID NO: 119)
GREVQKYSDLGPLYAEQE.
```

In a certain embodiments, the FG loop of the HSA binding $^{10}$Fn3 domains described herein comprises an amino acid sequence selected from the group consisting of:

```
                             (SEQ ID NO: 29)
VTGSGESPASSKP,
                             (SEQ ID NO: 50)
VTGSGESPASSAP,
                             (SEQ ID NO: 53)
VTGSGESPASSTP,
                             (SEQ ID NO: 56)
VTGSGESPASSSP.
```

In certain embodiments, additional regions in the $^{10}$Fn3 domain, such as the β-strand, N-terminal and/or C-terminal regions, may also be modified in sequence relative to SEQ ID NO: 23, 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118, and such additional modifications may also contribute to binding to the target.

The non binding regions of the HSA binding $^{10}$Fn3 domains described herein may have anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions, or additions relative to the scaffold amino acids residues of SEQ ID NO: 1, 23, 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118. Such scaffold modifications may be made, so long as the HSA binding $^{10}$Fn3 domain is capable of binding HSA with a desired $K_D$.

In certain embodiments, the amino acid sequences of the N-terminal and/or C-terminal regions of the polypeptides provided herein may be modified by deletion, substitution, or insertion relative to the amino acid sequences of the corresponding regions of the wild-type human $^{10}$Fn3 domain (SEQ ID NO: 1). The $^{10}$Fn3 domains generally begin with amino acid number 1 of SEQ ID NO: 1. However, domains with amino acid deletions are also encompassed.

Additional sequences may also be added to the N- or C-terminus of a $^{10}$Fn3 domain having the amino acid sequence of any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118. For example, in some embodiments, the N-terminal extension consists of an amino acid sequence selected from the group consisting of: M, MG, and G, which may be added to $^{10}$Fn3 domains starting with "VSD" as, e.g., in SEQ ID NO: 1. In exemplary embodiments, an alternative N-terminal region having from 1-20, 1-15, 1-10, 1-8, 1-5, 1-4, 1-3, 1-2, or 1 amino acids in length can be added to the N-terminal region of any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118. Exemplary alternative N-terminal regions include (represented by the single letter amino acid code) M, MG, G, MGVSDVPRDL (SEQ ID NO: 3) and GVSDVPRDL (SEQ ID NO: 4). Other suitable alternative N-terminal regions include, for example, $X_n$SDVPRDL (SEQ ID NO: 5), $X_n$D-VPRDL (SEQ ID NO: 6), $X_n$VPRDL (SEQ ID NO: 7), $X_n$PRDL (SEQ ID NO: 8) $X_n$RDL (SEQ ID NO: 9), $X_n$DL (SEQ ID NO: 10), or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In certain embodiments, the alternative N-terminal region comprises the amino acid sequence MASTSG (SEQ ID NO: 11).

In exemplary embodiments, an alternative C-terminal region having from 1-20, 1-15, 1-10, 1-8, 1-5, 1-4, 1-3, 1-2, or 1 amino acids in length can be added to the C-terminal region of any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118. Specific examples of alternative C-terminal sequences include, for example, polypeptides comprising, consisting essentially of, or consisting of, EIEK (SEQ ID NO: 12), EGSGC (SEQ ID NO: 13), EIEKPCQ (SEQ ID NO: 14), EIEKPSQ (SEQ ID NO: 15), EIEKP (SEQ ID NO: 16), EIEKPS (SEQ ID NO: 17), or EIEKPC (SEQ ID NO: 18). In certain embodiments, the alternative C-terminal region comprises EIDK (SEQ ID NO: 19), and in particular embodiments, the alternative C-terminal region is either EIDKPCQ (SEQ ID NO: 20) or EIDKPSQ (SEQ ID NO: 21). Additional suitable alternative C-terminal regions include those set forth in SEQ ID NOs: 148-172.

In certain embodiments, the C-terminal extension sequences comprise E and D residues, and may be between 8 and 50, 10 and 30, 10 and 20, 5 and 10, and 2 and 4 amino acids in length. In certain embodiments, tail sequences include ED-based linkers in which the sequence comprises tandem repeats of ED. In certain embodiments, the tail sequence comprises 2-10, 2-7, 2-5, 3-10, 3-7, 3-5, 3, 4 or 5 ED repeats. In certain embodiments, the ED-based tail sequences may also include additional amino acid residues, such as, for example: EI, EID, ES, EC, EGS, and EGC. Such sequences are based, in part, on known Adnectin tail sequences, such as EIDKPSQ (SEQ ID NO: 21), in which residues D and K have been removed. In certain embodiments, the ED-based tail comprises an E, I or EI residues before the ED repeats.

In certain embodiments, an alternative C-terminal moiety, which can be linked to the C-terminal amino acids RT (i.e., corresponding to amino acid 93-94 of SEQ ID NO: 1) of any of the $^{10}$Fn3 domains provided herein comprises the amino acids $P_mX_n$, wherein P is proline, X is any amino acid, m is an integer that is at least 1 and n is 0 or an integer that is at least 1. In certain embodiments, the alternative C-terminal moiety comprises the amino acids PC. In certain embodiments, the alternative C-terminal moiety comprises the amino acids PI, PC, PID, PIE, PIDK (SEQ ID NO: 159), PIEK (SEQ ID NO: 160), PIDKP (SEQ ID NO: 161), PIEKP (SEQ ID NO: 162), PIDKPS (SEQ ID NO: 163), PIEKPS (SEQ ID NO: 164), PIDKPC (SEQ ID NO: 165), PIEKPC (SEQ ID NO: 166), PIDKPSQ (SEQ ID NO: 167), PIEKPSQ (SEQ ID NO: 168), PIDKPCQ (SEQ ID NO: 169), PIEKPCQ (SEQ ID NO: 170), PHHHHHH (SEQ ID NO: 171), and PCHHHHHH (SEQ ID NO: 172).

In certain embodiments, the HSA binding $^{10}$Fn3 domains described herein comprise, or alternatively lack a 6× his tail.

In certain embodiments, the HSA binding $^{10}$Fn3 domains correspond to core $^{10}$Fn3 domains which lack the N-terminal leader and C-terminal tail, as set forth in SEQ ID NOs: 30, 36, 42, 48, 51, 54, 57, 60, 62, 65, 67, 70, 73, 75, 78, 81, 83, 86, 89, 91, 93, 95, 97, 100, 102, 104, 106, 108, 111, 113, 115, and 117.

In some embodiments, provided herein are mutant HSA binding $^{10}$Fn3 domains which have a cysteine residue introduced at a specific position to allow or, e.g., chemical conjugation to heterologous moieties (e.g., a heterologous polypeptide such as a $^{10}$Fn3 domain). In preferred embodiments, the cysteine mutations do not substantially alter the binding of the HSA binding $^{10}$Fn3 domain to HSA.

In certain embodiments, a proline residue is introduced at the C-terminus of the $^{10}$Fn3 domain, for example, as shown, e.g., in SEQ ID NOs: 33, 34, 39, 40, 45, and 46. The other HSA binding 10Fn3 domains described herein, e.g., those with a core sequence of SEQ ID NOs: 48, 51, 54, 57, 60, 62, 65, 67, 70, 73, 75, 78, 81, 83, 86, 89, 91, 93, 95, 97, 100, 102, 104, 106, 108, 111, 113, 115, and 117, can be modified in a similar manner. In certain embodiments, the proline residue is introduced at the C-terminus of a tandem HSA binding Adnectin. Addition of the proline residue does not preclude the addition of additional amino acid sequences to the C-terminus of an HSA binding $^{10}$Fn3 domain or tandem HSA binding Adnectin.

In certain embodiments, the HSA binding $^{10}$Fn3 domains described herein bind to HSA with a $K_D$ of less than 3 μM, 2.5 μM, 2 μM, 1.5 μM, 1 μM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 µM, 0.5 nM to 50 nM, 0.5 nM to 100 nM, 0.5 nM to 1 µM, 1 nM to 50 nM, 1 nM to 100 nM, 1 nM to 1 µM, 50 nM to 3 µM, 50 nM to 2 µM, 50 nM to 1 µM, 50 nM to 500 nM, 50 nM to 100 nM, 100 nM to 3 µM, 100 nM to 2 µM, 100 nM to 1 µM, 250 nM to 3 µM, 250 nM to 2 µM, 250 nM to 1 µM, 250 nM to 500 nM, 500 nM to 3 µM, 500 nM to 2 µM, 500 nM to 1 µM, 1 µM to 3 µM, or 1 µM to 2 µM.

In certain embodiments, the HSA binding $^{10}$Fn3 domains described herein may also bind serum albumin from one or more of cynomolgus monkey, rhesus monkey, rat, or mouse.

In certain embodiments, the HSA binding $^{10}$Fn3 domains described herein bind to rhesus serum albumin (RhSA) or cynomolgus monkey serum albumin (CySA) with a $K_D$ of less than 3 µM, 2.5 µM, 2 µM, 1.5 µM, 1 µM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 µM, 0.5 nM to 50 nM, 0.5 nM to 100 nM, 0.5 nM to 1 µM, 1 nM to 50 nM, 1 nM to 100 nM, 1 nM to 1 µM, 50 nM to 3 µM, 50 nM to 2 µM, 50 nM to 1 µM, 50 nM to 500 nM, 50 nM to 100 nM, 100 nM to 3 µM, 100 nM to 2 µM, 100 nM to 1 µM, 250 nM to 3 µM, 250 nM to 2 µM, 250 nM to 1 µM, 250 nM to 500 nM, 500 nM to 3 µM, 500 nM to 2 µM, 500 nM to 1 µM, 1 µM to 3 µM, or 1 µM to 2 µM.

In certain embodiments, the HSA binding $^{10}$Fn3 domains described herein bind to rhesus serum albumin (RhSA), cynomolgus monkey serum albumin (CySA), and mouse serum albumin (MSA) with a $K_D$ of less than 3 µM, 2.5 µM, 2 µM, 1.5 µM, 1 µM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 µM, 0.5 nM to 50 nM, 0.5 nM to 100 nM, 0.5 nM to 1 µM, 1 nM to 50 nM, 1 nM to 100 nM, 1 nM to 1 µM, 50 nM to 3 µM, 50 nM to 2 µM, 50 nM to 1 µM, 50 nM to 500 nM, 50 nM to 100 nM, 100 nM to 3 µM, 100 nM to 2 µM, 100 nM to 1 µM, 250 nM to 3 µM, 250 nM to 2 µM, 250 nM to 1 µM, 250 nM to 500 nM, 500 nM to 3 µM, 500 nM to 2 µM, 500 nM to 1 µM, 1 µM to 3 µM, or 1 µM to 2 µM.

In certain embodiments, the HSA binding $^{10}$Fn3 domains described herein bind to rhesus serum albumin (RhSA), cynomolgus monkey serum albumin (CySA), mouse serum albumin (MSA), and rat serum albumin (RSA) with a $K_D$ of less than 3 µM, 2.5 µM, 2 µM, 1.5 µM, 1 µM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 µM, 0.5 nM to 50 nM, 0.5 nM to 100 nM, 0.5 nM to 1 µM, 1 nM to 50 nM, 1 nM to 100 nM, 1 nM to 1 µM, 50 nM to 3 µM, 50 nM to 2 µM, 50 nM to 1 µM, 50 nM to 500 nM, 50 nM to 100 nM, 100 nM to 3 µM, 100 nM to 2 µM, 100 nM to 1 µM, 250 nM to 3 µM, 250 nM to 2 µM, 250 nM to 1 µM, 250 nM to 500 nM, 500 nM to 3 µM, 500 nM to 2 µM, 500 nM to 1 µM, 1 µM to 3 µM, or 1 µM to 2 µm.

In certain embodiments, the HSA binding $^{10}$Fn3 domains described herein bind to HSA at a pH range of 5.5 to 7.4.

In certain embodiments, the HSA binding $^{10}$Fn3 domains described herein bind to domain I-II of HSA.

In certain embodiments, the serum half-life of the HSA binding $^{10}$Fn3 domains described herein or the serum half-life of the HSA binding $^{10}$Fn3 domain linked to a heterologous moiety (e.g., a second $^{10}$Fn3 domain) is at least 2 hours, 2.5 hours, 3 hours, 4 hours, 5 hours, 6 hours, 7 hours, 8 hours, 9 hours, 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours. In certain embodiments, the serum half-life of the HSA binding $^{10}$Fn3 domains or the serum half-life of the HSA binding $^{10}$Fn3 domain linked to a heterologous moiety (e.g., a second $^{10}$Fn3 domain) is 2-200 hours, 5-200 hours, 10-200 hours, 25-200 hours, 50-200 hours, 100-200 hours, 150-200 hours, 2-150 hours, 2-100 hours, 2-50 hours, 2-25 hours, 2-10 hours, 2-5 hours, 5-150 hours, 10-100 hours, or 25-50 hours.

B. Cross-Competing Adnectins and/or Adnectins that Bind to the Same Adnectin Binding Site Provided herein are proteins, such as Adnectins, antibodies or antigen binding fragments thereof, small molecules, peptides, and the like that compete (e.g., cross-compete) for binding to HSA with the particular HSA binding $^{10}$Fn3 domains described herein, e.g., the HSA binding $^{10}$Fn3 domains (Adnectins) comprising the amino acid sequence set forth in any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118. Such competing proteins can be identified based on their ability to competitively inhibit binding to HSA of the serum albumin binding $^{10}$Fn3 domains described herein in standard serum albumin binding assays. For example, standard ELISA assays can be used in which recombinant HSA is immobilized on the plate, one of the proteins is fluorescently labeled and the ability of non-labeled protein to compete off the binding of the labeled protein is evaluated.

The following exemplary competition assays are provided in the context of HSA binding $^{10}$Fn3 domains competing for binding to HSA with one of the HSA binding $^{10}$Fn3 domains described herein. The same assays can be performed where a non-Adnectin protein is tested for competition. In one embodiment, a competitive ELISA format can be performed to determine whether two HSA binding Adnectins bind overlapping Adnectin binding sites (epitopes) on HSA. In one format, Adnectin #1 is coated on a plate, which is then blocked and washed. To this plate is added either HSA alone, or HSA pre-incubated with a saturating concentration of Adnectin #2. After a suitable incubation period, the plate is washed and probed with a polyclonal anti-HSA antibody, followed by detection with streptavidin-HRP conjugate and standard tetramethylbenzidine development procedures. If the OD signal is the same with or without preincubation with Adnectin #2, then the two Adnectins bind independently of one another, and their Adnectin binding sites do not overlap. If, however, the OD signal for wells that received serum albumin/Adnectin #2 mixtures is lower than for those that received HSA alone, then binding of Adnectin #2 is confirmed to block binding of Adnectin #1 to HSA.

Alternatively, a similar experiment is conducted by surface plasmon resonance (SPR, e.g., BIAcore). Adnectin #1 is immobilized on an SPR chip surface, followed by injections of either HSA alone or HSA pre-incubated with a saturating concentration of Adnectin #2. If the binding signal for HSA/Adnectin #2 mixtures is the same or higher than that of HSA alone, then the two Adnectins bind independently of one another, and their Adnectin binding sites do not overlap. If, however, the binding signal for HSA/Adnectin #2 mixtures is lower than the binding signal for HSA alone, then binding of Adnectin #2 is confirmed to block binding of Adnectin #1 to HSA. A feature of these experiments is the use of saturating concentrations of Adnectin #2. If HSA is not saturated with Adnectin #2, then the conclusions above do not hold. Similar experiments can be used to determine if any two HSA binding proteins bind to overlapping Adnectin binding sites.

Both assays exemplified above may also be performed in the reverse order where Adnectin #2 is immobilized and HSA-Adnectin #1 are added to the plate. Alternatively, Adnectin #1 and/or #2 can be replaced with a monoclonal antibody and/or soluble receptor-Fc fusion protein.

In certain embodiments, competition can be determined using a HTRF sandwich assay.

Candidate competing HSA binding proteins, e.g., Adnectins, can inhibit the binding of the Adnectins described herein to HSA by at least 50%, at least 55%, at least 60%, at least 65%, at least 70%, at least 75%, at least 80%, at least 85%, at least 90%, at least 95%, at least 97%, at least 98%, or at least 99%. The % competition can be determined using the methods described above.

In certain embodiments, provided herein are Adnectins which bind to the same Adnectin binding site as the HSA binding $^{10}$Fn3 domains described herein. The epitope bound by a particular Adnectin can be determined using art-recognized epitope mapping methods, such as x-ray analyses of crystals of antigen:Adnectin complexes (which provides atomic resolution of the epitope), protease mapping, hydrogen/deuterium exchange mass spectrometry (HDX-MS), 2-dimensional nuclear magnetic resonance, alanine scanning, and deep mutational scanning (see, e.g., Epitope Mapping Protocols in Methods in Molecular Biology, Vol. 66, G. E. Morris, Ed. (1996)).

C. Multivalent/Tandem Adnectins

Provided herein are multivalent proteins that comprise two or more $^{10}$Fn3 domains, at least one of which binds specifically to HSA. For example, a multivalent protein may comprise 2, 3 or more $^{10}$Fn3 domains that are covalently associated. In certain embodiments, multivalent protein is a bispecific or dimeric protein comprising two $^{10}$Fn3 domains. In certain embodiments, a multivalent protein comprises a first $^{10}$Fn3 domain that binds to HSA (e.g., a $^{10}$Fn3 domain described supra in Section A) and a second $^{10}$Fn3 domain that binds to a second target molecule. When both the first and second target molecules are HSA, the first and second $^{10}$Fn3 domains may bind to the same or different epitopes. Additionally, when the first and second target molecules are the same, the regions of modification in the $^{10}$Fn3 domain that are associated with target binding may be the same or different.

In certain embodiments, each $^{10}$Fn3 domain of a multivalent fibronectin-based protein scaffold binds to HSA with a $K_D$ of less than 3 µM, 2.5 µM, 2 µM, 1.5 µM, 1 µM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 µM, 0.5 nM to 50 nM, 0.5 nM to 100 nM, 0.5 nM to 1 µM, 1 nM to 50 nM, 1 nM to 100 nM, 1 nM to 1 µM, 50 nM to 3 µM, 50 nM to 2 µM, 50 nM to 1 µM, 50 nM to 500 nM, 50 nM to 100 nM, 100 nM to 3 µM, 100 nM to 2 µM, 100 nM to 1 µM, 250 nM to 3 µM, 250 nM to 2 µM, 250 nM to 1 µM, 250 nM to 500 nM, 500 nM to 3 µM, 500 nM to 2 µM, 500 nM to 1 µM, 1 µM to 3 µM, or 1 µM to 2 µM. In exemplary embodiments, each $^{10}$Fn3 domain of a multivalent fibronectin based protein scaffold binds specifically to HSA, i.e., a target not bound by a wild-type $^{10}$Fn3 domain, particularly the wild-type human $^{10}$Fn3 domain.

The $^{10}$Fn3 domains in a multivalent fibronectin based scaffold protein may be connected by a polypeptide linker. Exemplary polypeptide linkers include polypeptides having from 1-20, 1-15, 1-10, 1-8, 1-5, 1-4, 1-3, or 1-2 amino acids. Suitable linkers for joining the $^{10}$Fn3 domains are those which allow the separate domains to fold independently of each other forming a three dimensional structure that permits high affinity binding to a target molecule. Specific examples of suitable linkers include glycine-serine based linkers, glycine-proline based linkers, proline-alanine based linkers as well as linkers having the amino acid sequence PSTPPTPSPSTPPTPSPS (SEQ ID NO: 120). In certain embodiments, the linker is a glycine-serine based linker. In certain embodiments, the linker is a glycine-serine based linker. These linkers comprise glycine and serine residues and may be between 8 and 50, 10 and 30, and 10 and 20 amino acids in length. Examples include linkers having an amino acid sequence $(GS)_7$ (SEQ ID NO: 121), $G(GS)_6$ (SEQ ID NO: 122), and $G(GS)_7G$ (SEQ ID NO: 123). Other linkers contain glutamic acid, and include, for example, $(GSE)_5$ (SEQ ID NO: 124) and GGSEGGSE (SEQ ID NO: 125). Other exemplary glycine-serine linkers include $(GS)_4$ (SEQ ID NO: 126), $(GGGGS)_7$ (SEQ ID NO: 127), $(GGGGS)_5$ (SEQ ID NO: 128), and $(GGGGS)_3G$ (SEQ ID NO: 129). In some embodiments, the linker is a glycine-proline based linker. These linkers comprise glycine and proline residues and may be between 3 and 30, 10 and 30, and 3 and 20 amino acids in length. Examples include linkers having an amino acid sequence $(GP)_3G$ (SEQ ID NO: 130), $(GP)_5G$ (SEQ ID NO: 131), and GPG. In certain embodiments, the linker may be a proline-alanine based linker having between 3 and 30, 10 and 30, and 3 and 20 amino acids in length. Examples of proline alanine based linkers include, for example, $(PA)_3$ (SEQ ID NO: 132), $(PA)_6$ (SEQ ID NO: 133) and $(PA)_9$ (SEQ ID NO: 134). It is contemplated, that the optimal linker length and amino acid composition may be determined by routine experimentation by methods well known in the art. In exemplary embodiments, the linker does not contain any Asp-Lys (DK) pairs.

In certain embodiments, the linker has the amino acid sequence PSPEPPTPEP (SEQ ID NO: 135), PSPEPPT-PEPPSPEPPTPEP (SEQ ID NO: 136), PSPEPPT-PEPPSPEPPTPEPPSPEPPTPEP (SEQ ID NO: 137), or PSPEPPTPEPPSPEPPTPEPPSPEPPTPEPPSPEPPTPEP (SEQ ID NO: 138). Generally a linker may comprise the amino acid sequence (PSPEPPTPEP). (SEQ ID NO: 144), wherein n is 1, 2, 3, 4, 5, 6, 7, 8, 9, 10, 1-5 or 1-10. In certain embodiments, the linker has the amino acid sequence EEEEDE (SEQ ID NO: 139), EEEEDEEEEDE (SEQ ID NO: 140), EEEEDEEEEDEEEEDEEEEDE (SEQ ID NO: 141), EEEEDEEEEDEEEEDEEEEDEEEEDE (SEQ ID NO: 142). Generally, a linker may comprise the sequence (EEEEDE).E (SEQ ID NO: 145), wherein n is 1, 2, 3, 4, 5, 6, 7, 8, 9, 10, 1-5 or 1-10. In certain embodiments, the linker has the amino acid sequence RGGEEKKKEKE-KEEQEERETKTP (SEQ ID NO: 143). Such linkers may be used to connect the HSA binding Adnectin to another polypeptide (e.g., another Adnectin). Exemplary uses of the PSPEPPTPEP (SEQ ID NO: 135) linker is shown below (the "G" after YRTP in SEQ ID NO: 74 and TPEP in SEQ ID NO: 75 is optional).

N-terminal Adnectin connected to C-terminal polypeptide:

(SEQ ID NO: 146)
. . . NYRTPGPSPEPPTPEP-*polypeptide*

N-terminal polypeptide connected to C-terminal Adnectin:

(SEQ ID NO: 147)
polypeptide-PSPEPPTPEPGVSDV . . .

In certain embodiments, the multivalent Adnectin is a tandem Adnectin comprising a first $^{10}$Fn3 domain which binds to HSA (e.g., a PKE3 Adnectin), and a second $^{10}$Fn3 domain that binds to a specific target. Tandem Adnectins may have the configuration HSA binding Adnectin-X and X-HSA binding Adnectin, wherein X is a target specific $^{10}$Fn3 domain. The skilled artisan would be familiar with methods for testing the functional activity and assessing the biophysical properties of such tandem Adnectin molecules.

In one aspect, the invention provides a fusion polypeptide comprising a first fibronectin type III tenth ($^{10}$Fn3) domain and a second $^{10}$Fn3 domain, wherein the first $^{10}$Fn3 domain binds to HSA and comprises AB, BC, CD, DE, EF, and FG loops, wherein the CD loop has 1, 2, or 3 amino acid substitutions, and the FG loop optionally has 1, 2, or 3 amino acid substitutions, relative to the CD and FG loops of a $^{10}$Fn3 domain comprising the amino acid sequence set forth in SEQ ID NO: 23 (e.g., the amino acid substitutions to the CD and/or FG loops described supra in Section A), and wherein the serum half-life of a moiety (e.g., polypeptide) that is linked to the $^{10}$Fn3 domain is extended relative to that of the moiety that is not linked to the $^{10}$Fn3 domain. A "first" domain and a second "domain" may be in the N- to C-terminal or C- to N-terminal orientation.

In certain embodiments, the ratio of the off-rate of the first $^{10}$Fn3 domain to the off-rate of the $^{10}$Fn3 domain comprising the amino acid sequence set forth in SEQ ID NO: 23 is at least about 2, such as at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 75, at least about 100 or higher. In certain embodiments, the ratio is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60. In certain embodiments, the ratio is 1.0, 1.1, 1.2, 3.3, 3.9, 4.0, 4.1, 4.8, 5.0, 5.6, 6.5, 6.6, 8, 11, 14, 17, 20, 23, 28, 28.9, 30.3, 32.0, 34.0, 34.3, 37.3, 50.0, 52, 52.7, 53.0, 56.0, or 79.4. In certain embodiments, the ratio is in the range of 2-100, 2-75, 2-50, 2-45, 2-40, 2-35, 2-30, 2-25, 2-20, 2-15, 2-10, 2-5, 5-100, 5-75, 5-50, 5-45, 5-40, 5-35, 5-30, 5-25, 5-20, 5-15, 5-10, 10-100, 10-75, 10-50, 10-45, 10-40, 10-35, 10-30, 10-25, 10-20, 10-15, 20-100, 20-75, 20-50, 20-45, 20-40, 20-35, 20-30, 20-25, 30-100, 30-75, 30-50, 30-45, 30-40, 30-35, 40-100, 40-75, 40-50, 40-45, 50-100, 50-75, 60-100, 60-75, 70-100, 70-75, 80-100, 80-90, 90-100, 3-4, 3-5, 3-6, 3-7, 25-40, 30-40, 50-55, 75-85, 1-80, 1-70, 1-60, 1-50, 1-40, 1-30, 1-20, 1-10, or 1-5.

In certain embodiments, the first $^{10}$Fn3 domain binds to HSA with an on-rate (ka) that is within an order of magnitude (i.e., within 10-fold) of the ka of the $^{10}$Fn3 domain comprising the amino acid sequence set forth in SEQ ID NO: 23.

In certain embodiments, e.g., of multivalent Adnectins, the first $^{10}$Fn3 domain comprises an amino acid sequence at least 70%, 75%, 80%, 85%, 90%, 95%, 96%, 97%, 98%, 99% or 100% identical to any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118, or differs therefrom in at most 1, 1-2, 1-5, 1-10 or 1-20 amino acids (e.g., amino acid deletions, additions or substitutions (e.g., conservative amino acid substitutions), such as one or more of the amino acid substitutions described herein).

In certain embodiments, the first $^{10}$Fn3 domain comprises the amino acid sequence of any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118.

In some embodiments, the multivalent Adnectin comprises a second $^{10}$Fn3 domain that is a $^{10}$Fn3 domain that specifically binds to a target protein other than HSA, e.g., a target protein (e.g., therapeutic moiety) described infra in Section D.

In one aspect, the HSA binding tandem Adnectins described herein bind to HSA with a $K_D$ of less than 3 μM, 2.5 μM, 2 μM, 1.5 μM, 1 μM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM, 1 nM to 1 μM, 50 nM to 3 μM, 50 nM to 2 μM, 50 nM to 1 μM, 50 nM to 500 nM, 50 nM to 100 nM, 100 nM to 3 μM, 100 nM to 2 μM, 100 nM to 1 μM, 250 nM to 3 μM, 250 nM to 2 μM, 250 nM to 1 μM, 250 nM to 500 nM, 500 nM to 3 μM, 500 nM to 2 μM, 500 nM to 1 μM, 1 μM to 3 μM, or 1 μM to 2 μM.

In certain embodiments, the HSA binding tandem Adnectins described herein may also bind serum albumin from one or more of cynomolgus monkey, rhesus monkey, rat, or mouse.

In certain embodiments, the HSA binding tandem Adnectins described herein bind to rhesus serum albumin (RhSA) or cynomolgus monkey serum albumin (CySA) with a $K_D$ of less than 3 μM, 2.5 μM, 2 μM, 1.5 μM, 1 μM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM, 1 nM to 1 μM, 50 nM to 3 μM, 50 nM to 2 μM, 50 nM to 1 μM, 50 nM to 500 nM, 50 nM to 100 nM, 100 nM to 3 μM, 100 nM to 2 μM, 100 nM to 1 μM, 250 nM to 3 μM, 250 nM to 2 μM, 250 nM to 1 μM, 250 nM to 500 nM, 500 nM to 3 μM, 500 nM to 2 μM, 500 nM to 1 μM, 1 μM to 3 μM, or 1 μM to 2 μM.

In certain embodiments, the HSA binding tandem Adnectins described herein bind to rhesus serum albumin (RhSA), cynomolgus monkey serum albumin (CySA), and mouse serum albumin (MSA) with a $K_D$ of less than 3 μM, 2.5 μM, 2 μM, 1.5 μM, 1 μM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM, 1 nM to 1 μM, 50 nM to 3 μM, 50 nM to 2 μM, 50 nM to 1 μM, 50 nM to 500 nM, 50 nM to 100 nM, 100 nM to 3 μM, 100 nM to 2 μM, 100 nM to 1 μM, 250 nM to 3 μM, 250 nM to 2 μM, 250 nM to 1 μM, 250 nM to 500 nM, 500 nM to 3 μM, 500 nM to 2 μM, 500 nM to 1 μM, 1 μM to 3 μM, or 1 μM to 2 μM.

In certain embodiments, the HSA binding tandem Adnectins described herein bind to rhesus serum albumin (RhSA), cynomolgus monkey serum albumin (CySA), mouse serum albumin (MSA), and rat serum albumin (RSA) with a $K_D$ of less than 3 µM, 2.5 µM, 2 µM, 1.5 µM, 1 µM, 500 nM, 100 nM, 50 nM, 10 nM, 1 nM, 500 pM, 100 pM, 100 pM, 50 pM, or 10 pM. The $K_D$ may be, e.g., in the range of 0.1 nM to 50 nM, 0.1 nM to 100 nM, 0.1 nM to 1 µM, 0.5 nM to 50 nM, 0.5 nM to 100 nM, 0.5 nM to 1 µM, 1 nM to 50 nM, 1 nM to 100 nM, 1 nM to 1 µM, 50 nM to 3 µM, 50 nM to 2 µM, 50 nM to 1 µM, 50 nM to 500 nM, 50 nM to 100 nM, 100 nM to 3 µM, 100 nM to 2 µM, 100 nM to 1 µM, 250 nM to 3 µM, 250 nM to 2 µM, 250 nM to 1 µM, 250 nM to 500 nM, 500 nM to 3 µM, 500 nM to 2 µM, 500 nM to 1 µM, 1 µM to 3 µM, or 1 µM to 2 µM.

In certain embodiments, the HSA binding tandem Adnectins described herein bind to serum albumin at a pH range of 5.5 to 7.4.

In certain embodiments, the HSA binding tandem Adnectins described herein bind to domain I-II of HSA.

In certain embodiments, the HSA binding tandem Adnectins described herein has a serum half-life in the presence of HSA, cynomolgus monkey serum albumin, rhesus monkey serum albumin, mouse serum albumin, and/or rat serum albumin of at least 1 hour, 2 hours, 5 hours, 10 hours, 20 hours, 30 hours, 40 hours, 50 hours, 60 hours, 70 hours, 80 hours, 90 hours, 100 hours, 150 hours, 200 hours, or at least about 300 hours.

In certain embodiments, the HSA binding tandem Adnectins described herein has a serum half-life in the presence of HSA, cynomolgus monkey serum albumin, rhesus monkey serum albumin, mouse serum albumin, and/or rat serum albumin of 1-300 hours, such as 1-250 hours, 1-200 hours, 1-150 hours, 1-100 hours, 1-90 hours, 1-80 hours, 1-70 hours, 1-60 hours, 1-50 hours, 1-40 hours, 1-30 hours, 1-20 hours, 1-10 hours, 1-5 hours, 5-300 hours, 10-300 hours, 20-300 hours, 30-300 hours, 40-300 hours, 50-300 hours, 60-300 hours, 70-300 hours, 80-300 hours, 90-300 hours, 100-300 hours, 150-300 hours, 200-300 hours, 250-300 hours, 5-250 hours, 10-200 hours, 50-150 hours, or 80-120 hours.

In certain embodiments, the serum half-life of the partner Adnectin in the HSA binding tandem Adnectin is increased relative to the serum half-life of the partner Adnectin when not conjugated to the HSA binding Adnectin.

In certain embodiments, the serum half-life of the HSA binding tandem Adnectin is at least 20, 40, 60, 80, 100, 120, 150, 180, 200, 400, 600, 800, 1000, 1200, 1500, 1800, 1900, 2000, 2500, or 3000% longer relative to the serum half-life of the partner Adnectin when not fused to the HSA binding Adnectin.

In certain embodiments, the serum half-life of the HSA binding tandem Adnectin is 20-3000%, such as 40-3000%, 60-3000%, 80-3000%, 100-3000%, 120-3000%, 150-3000%, 180-3000%, 200-3000%, 400-3000%, 600-3000%, 800-3000%, 1000-3000%, 1200-3000%, 1500-3000%, 1800-3000%, 1900-3000%, 2000-3000%, 2500-3000%, 20-2500%, 20-2000%, 20-1900%, 20-1800%, 20-1500%, 20-1200%, 20-1000%, 20-800%, 20-600%, 20-400%, 20-200%, 20-180%, 20-150%, 20-120%, 20-100%, 20-80%, 20-60%, 20-40%, 50-2500%, 100-2000%, 150-1500%, 200-1000%, 400-800%, or 500-700% longer relative to the serum half-life of the partner Adnectin when not fused to the HSA binding Adnectin.

In certain embodiments, the serum half-life of the HSA binding tandem Adnectin is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the partner Adnectin when not fused to the HSA binding Adnectin.

In certain embodiments, the serum half-life of the HSA binding tandem Adnectin is 1.5-50 fold, such as 1.5-40 fold, 1.5-35 fold, 1.5-30 fold, 1.5-27 fold, 1.5-25 fold, 1.5-22 fold, 1.5-20 fold, 1.5-17 fold, 1.5-15 fold, 1.5-13 fold, 1.5-12 fold, 1.5-10 fold, 1.5-9 fold, 1.5-8 fold, 1.5-7 fold, 1.5-6 fold, 1.5-5 fold, 1.5-4.5 fold, 1.5-4 fold, 1.5-3.5 fold, 1.5-3 fold, 1.5-2.5 fold, 1.5-2 fold, 2-50 fold, 2.5-50 fold, 3-50 fold, 3.5-50 fold, 4-50 fold, 4.5-50 fold, 5-50 fold, 6-50 fold, 7-50 fold, 8-50 fold, 10-50 fold, 12-50 fold, 13-50 fold, 15-50 fold, 17-50 fold, 20-50 fold, 22-50 fold, 25-50 fold, 27-50 fold, 30-50 fold, 40-50 fold, 2-40 fold, 5-35 fold, 10-20 fold, or 10-15 fold greater than the serum half-life of the partner Adnectin when not fused to the HSA binding Adnectin.

In certain embodiments, the serum half-life of the HSA binding tandem Adnectin is at least 2 hours, 2.5 hours, 3 hours, 4 hours, 5 hours, 6 hours, 7 hours, 8 hours, 9 hours, 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

In certain embodiments, the serum half-life of the HSA binding tandem Adnectin is 2-200 hours, 2.5-200 hours, 3-200 hours, 4-200 hours, 5-200 hours, 6-200 hours, 7-200 hours, 8-200 hours, 9-200 hours, 10-200 hours, 15-200 hours, 20-200 hours, 25-200 hours, 30-200 hours, 35-200 hours, 40-200 hours, 50-200 hours, 60-200 hours, 70-200 hours, 80-200 hours, 90-200 hours, 100-200 hours, 125-200 hours, 150-200 hours, 175-200 hours, 190-200 hours, 2-190 hours, 2-175 hours, 2-150 hours, 2-125 hours, 2-100 hours, 2-90 hours, 2-80 hours, 2-70 hours, 2-60 hours, 2-50 hours, 2-40 hours, 2-35 hours, 2-30 hours, 2-25 hours, 2-20 hours, 2-15 hours, 2-10 hours, 2-9 hours, 2-8 hours, 2-7 hours, 2-6 hours, 2-5 hours, 2-4 hours, 2-3 hours, 5-175 hours, 10-150 hours, 15-125 hours, 20-100 hours, 25-75 hours, or 30-60 hours.

D. Conjugates of HSA Binding Adnectins

Certain aspects of the present invention provide for conjugates comprising a HSA binding $^{10}$Fn3 domain (e.g., as described supra in Sections A and B) and at least one additional moiety (e.g., a therapeutic moiety). The additional moiety may be useful for any diagnostic, imaging, or therapeutic purpose.

In some embodiments, the HSA binding $^{10}$Fn3 domain is fused to a second moiety that is a small organic molecule, a nucleic acid, a peptide, or a protein.

In certain embodiments, the HSA binding $^{10}$Fn3 domain is fused to a therapeutic moiety that targets receptors, receptor ligands, viral coat proteins, immune system proteins, hormones, enzymes, antigens, or cell signaling proteins. The fusion may be formed by attaching the second moiety to either end of the HSA binding $^{10}$Fn3 domain, i.e., HSA binding $^{10}$Fn3 domain-therapeutic molecule or therapeutic molecule-HSA binding $^{10}$Fn3 domain arrangements.

In certain embodiments, the serum half-life of a moiety (e.g., polypeptide) that is linked to the $^{10}$Fn3 domain is extended relative to that of the moiety that is not linked to the $^{10}$Fn3 domain. In certain embodiments, the serum half-life of the HSA binding $^{10}$Fn3 domain fusion is at least 5, 10, 15, 20, 30, 40, 50, 60, 70, 80, 90, 100, 120, 150, 180, 200, 400, 600, 800, 1000, 1200, 1500, 1800, 1900, 2000, 2500, or 3000% longer relative to the serum half-life of the moiety when not fused to the $^{10}$Fn3 domain. In certain embodiments, the serum half-life of the HSA binding $^{10}$Fn3 domain fusion is 5-3000%, such as 10-3000%, 15-3000%, 20-3000%, 30-3000%, 40-3000%, 50-3000%, 60-3000%, 70-3000%, 80-3000%, 90-3000%, 100-3000%, 120-3000%, 150-3000%, 180-3000%, 200-3000%, 400-3000%, 600-3000%, 800-3000%, 1000-3000%, 1200-3000%, 1500-3000%, 1800-3000%, 1900-3000%, 2000-3000%, 2500-3000%, 20-2500%, 20-2000%, 20-1900%, 20-1800%, 20-1500%, 20-1200%, 20-1000%, 20-800%, 20-600%, 20-400%, 20-200%, 20-180%, 20-150%, 20-120%, 20-100%, 20-80%, 20-60%, 20-40%, 10-2000%, 10-1900%, 10-1800%, 10-1500%, 10-1200%, 10-1000%, 10-800%, 10-600%, 10-400%, 10-200%, 10-180%, 10-150%, 10-120%, 10-100%, 10-80%, 10-60%, 10-40%, 10-20%, 5-2000%, 5-1900%, 5-1800%, 5-1500%, 5-1200%, 5-1000%, 5-800%, 5-600%, 5-400%, 5-200%, 5-180%, 5-150%, 5-120%, 5-100%, 5-80%, 5-60%, 5-40%, 5-20%, 5-15%, 5-10%, 50-2500%, 100-2000%, 150-1500%, 200-1000%, 400-800%, or 500-700% longer relative to the serum half-life of the moiety when not fused to the $^{10}$Fn3 domain.

In certain embodiments, the serum half-life of the HSA binding $^{10}$Fn3 domain fusion is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the moiety when not fused to the $^{10}$Fn3 domain.

In certain embodiments, the serum half-life of the HSA binding $^{10}$Fn3 domain fusion is 1.5-50 fold, such as 1.5-40 fold, 1.5-35 fold, 1.5-30 fold, 1.5-27 fold, 1.5-25 fold, 1.5-22 fold, 1.5-20 fold, 1.5-17 fold, 1.5-15 fold, 1.5-13 fold, 1.5-12 fold, 1.5-10 fold, 1.5-9 fold, 1.5-8 fold, 1.5-7 fold, 1.5-6 fold, 1.5-5 fold, 1.5-4.5 fold, 1.5-4 fold, 1.5-3.5 fold, 1.5-3 fold, 1.5-2.5 fold, 1.5-2 fold, 2-50 fold, 2.5-50 fold, 3-50 fold, 3.5-50 fold, 4-50 fold, 4.5-50 fold, 5-50 fold, 6-50 fold, 7-50 fold, 8-50 fold, 10-50 fold, 12-50 fold, 13-50 fold, 15-50 fold, 17-50 fold, 20-50 fold, 22-50 fold, 25-50 fold, 27-50 fold, 30-50 fold, 40-50 fold, 2-40 fold, 5-35 fold, 10-20 fold, or 10-15 fold greater than the serum half-life of the moiety when not fused to the $^{10}$Fn3 domain.

In certain embodiments, the serum half-life of the HSA binding $^{10}$Fn3 domain fusion is at least 2 hours, 2.5 hours, 3 hours, 4 hours, 5 hours, 6 hours, 7 hours, 8 hours, 9 hours, 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours. In certain embodiments, the serum half-life of the HSA binding Adnectin fusion is 2-200 hours, 2.5-200 hours, 3-200 hours, 4-200 hours, 5-200 hours, 6-200 hours, 7-200 hours, 8-200 hours, 9-200 hours, 10-200 hours, 15-200 hours, 20-200 hours, 25-200 hours, 30-200 hours, 35-200 hours, 40-200 hours, 50-200 hours, 60-200 hours, 70-200 hours, 80-200 hours, 90-200 hours, 100-200 hours, 125-200 hours, 150-200 hours, 175-200 hours, 190-200 hours, 2-190 hours, 2-175 hours, 2-150 hours, 2-125 hours, 2-100 hours, 2-90 hours, 2-80 hours, 2-70 hours, 2-60 hours, 2-50 hours, 2-40 hours, 2-35 hours, 2-30 hours, 2-25 hours, 2-20 hours, 2-15 hours, 2-10 hours, 2-9 hours, 2-8 hours, 2-7 hours, 2-6 hours, 2-5 hours, 2-4 hours, 2-3 hours, 5-175 hours, 10-150 hours, 15-125 hours, 20-100 hours, 25-75 hours, or 30-60 hours.

In certain embodiments, the HSA binding $^{10}$Fn3 domain fusion proteins bind to HSA with a $K_D$ of less than 3 μM, 2.5 μM, 2 μM, 1.5 μM, 1 μM, 500 nM, 100 nM, 50 nM, 10 nM, 1 nM, 500 pM, 100 pM, 100 pM, 50 pM or 10 pM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, a therapeutic moiety may be directly or indirectly linked to a HSA binding $^{10}$Fn3 domain, e.g., via a polymeric linker, as described herein (e.g., a linker as described supra in Section C). Polymeric linkers can be used to optimally vary the distance between each component of the fusion to create a protein fusion with one or more of the following characteristics: 1) reduced or increased steric hindrance of binding of one or more protein domains when binding to a protein of interest, 2) increased protein stability or solubility, 3) decreased protein aggregation, and 4) increased overall avidity or affinity of the protein.

Any of the linkers for linking two Adnectins, e.g., those described in Section C herein, may be used for linking an Adnectin to a heterologous moiety, such as a polypeptide.

In certain embodiments, a moiety, e.g., a polypeptide, is linked to a HSA binding Adnectin via a polypeptide linker having a protease site that is cleavable by a protease in the blood or target tissue. Such embodiments can be used to release a therapeutic protein for better delivery or therapeutic properties or more efficient production.

Additional linkers or spacers may be introduced at the C-terminus of a $^{10}$Fn3 domain between the $^{10}$Fn3 domain and the polypeptide linker.

In certain embodiments, a therapeutic moiety is linked to a HSA binding $^{10}$Fn3 domain via a biocompatible polymer such as a polymeric sugar. The polymeric sugar can include an enzymatic cleavage site that is cleavable by an enzyme in the blood or target tissue. Such embodiments can be used to release therapeutic proteins for better delivery or therapeutic properties or more efficient production.

The HSA binding $^{10}$Fn3 domain fusion molecules described herein are useful for increasing the half-life of a therapeutic moiety by creating a fusion between the therapeutic moiety and the HSA binding $^{10}$Fn3 domain. Such fusion molecules may be used to treat conditions which respond to the biological activity of the therapeutic moiety contained in the fusion. Thus, provided herein is the use of the HSA binding $^{10}$Fn3 domain fusion molecules in diseases caused by the disregulation of any of the following proteins or molecules.

In certain embodiments, the therapeutic moiety that is linked (either C-terminal or N-terminal) to the HSA binding $^{10}$Fn3 domain is VEGF, VEGF-R1, VEGF-R2, VEGF-R3, Her-1, Her-2, Her-3, EGF-I, EGF-2, EGF-3, Alpha3, cMet, ICOS, CD40L, LFA-I, c-Met, ICOS, LFA-I, IL-6, B7.1, W1.2, OX40, IL-1b, TACI, IgE, BAFF or BLys, TPO-R, CD19, CD20, CD22, CD33, CD28, IL-I-R1, TNF-alpha, TRAIL-R1, Complement Receptor 1, FGFa, Osteopontin, Vitronectin, Ephrin A1-A5, Ephrin B1-B3, alpha-2-macroglobulin, CCL1, CCL2, CCL3, CCL4, CCL5, CCL6, CCL7, CXCL8, CXCL9, CXCL10, CXCL11, CXCL12, CCL13, CCL14, CCL15, CXCL16, CCL16, CCL17, CCL18, CCL19, CCL20, CCL21, CCL22, PDGF, TGFb, GMCSF, SCF, p40 (IL12/IL23), IL1b, IL1a, IL1ra, IL2, IL3, IL4, IL5, IL6, IL8, IL10, IL12, IL15, IL23, Fas, FasL, Flt3 ligand, 41BB, ACE, ACE-2, KGF, FGF-7, SCF, Netrin1,2, IFNa,b,g, Caspase-2,3,7,8,10, ADAM S1,S5,8,9,15,TS1,TS5; Adiponectin, ALCAM, ALK-I, APRIL, Annexin V, Angiogenin, Amphiregulin, Angiopoietin-1,2,4, B7-1/CD80, B7-2/CD86, B7-H1, B7-H2, B7-H3, Bcl-2, BACE-I, BAK, BCAM, BDNF, bNGF, bECGF, BMP2,3,4,5,6,7,8; CRP, Cadherin 6, 8, 11; Cathepsin A,B,C,D,E,L,S,V,X; CD11a/LFA-1, LFA-3, GP2b3a, GH receptor, RSV F protein, IL-23 (p40, p19), IL-12, CD80, CD86, CD28, CTLA-4, alpha4-beta1, alpha4-beta7, TNF/Lymphotoxin, IgE, CD3, CD20, IL-6, IL-6R, BLYS/BAFF, IL-2R, HER2, EGFR, CD33, CD52, Digoxin, Rho (D), Varicella, Hepatitis, CMV, Tetanus, Vaccinia, Antivenom, Botulinum, Trail-R1, Trail-R2, cMet, TNF-R family, such as LA NGF-R, CD27, CD30, CD40, CD95, Lymphotoxin a/b receptor, WsI-I, TL1A/TNFSF15, BAFF, BAFF-R/TNFRSF13C, TRAIL R2/TNFRSF10B, TRAIL R2/TNFRSF10B, Fas/TNFRSF6 CD27/TNFRSF7, DR3/TNFRSF25, HVEM/TNFRSF14, TROY/TNFRSF19, CD40 Ligand/TNFSF5, BCMA/TNFRSF17, CD30/TNFRSF8, LIGHT/TNFSF14, 4-1BB/TNFRSF9, CD40/TNFRSF5, GITR/[Gamma]NFRSF 18, Osteoprotegerin/TNFRSF1 IB, RANK/TNFRSF1 IA, TRAIL R3/TNFRSF10C, TRAIL/TNFSFIO, TRANCE/RANK L/TNFSF11, 4-1BB Ligand/TNFSF9, TWEAK/TNFSF12, CD40 Ligand/TNFSFS, Fas Ligand/TNFSF6, RELT/TNFRSF19L, APRIL/TNFSF13, DcR3/TNFRSF6B, TNF RI/TNFRSFIA, TRAIL R1/TNFRSFIOA, TRAIL R4/TNFRSF10D, CD30 Ligand/TNFSF8, GITR Ligand/TNFSF18, TNFSF18, TACI/TNFRSF13B, NGF R/TNFRSF16, OX40 Ligand/TNFSF4, TRAIL R2/TNFRSF10B, TRAIL R3/TNFRSF10C, TWEAK R/TNFRSF12, BAFF/BLyS/TNFSF13, DR6/TNFRSF21, TNF-alpha/TNFSF1 A, Pro-TNF-alpha/TNFSF1A, Lymphotoxin beta R/TNFRSF3, Lymphotoxin beta R (LTbR)/Fc Chimera, TNF RI/TNFRSFIA, TNF-beta/TNFSF1B, PGRP-S, TNF RI/TNFRSFIA, TNF RII/TNFRSFIB, EDA-A2, TNF-alpha/TNFSFIA, EDAR, XEDAR, TNF RI/TNFRSFIA.

In certain embodiments, the therapeutic moiety that is linked (either C-terminal or N-terminal) to the HSA binding $^{10}$Fn3 domain is any of the following proteins or proteins binding thereto: 4EBP1, 14-3-3 zeta, 53BP1, 2B4/SLAMF4, CCL21/6Ckine, 4-1BB/TNFRSF9, 8D6A, 4-1BB Ligand/TNFSF9, 8-oxo-dG, 4-Amino-1,8-naphthalimide, A2B5, Aminopeptidase LRAP/ERAP2, A33, Aminopeptidase N/ANPEP, Aag, Aminopeptidase P2/XPNPEP2, ABCG2, Aminopeptidase P1/XPNPEP1, ACE, Aminopeptidase PILS/ARTS1, ACE-2, Amnionless, Actin, Amphiregulin, beta-Actin, AMPK alpha 1/2, Activin A, AMPK alpha 1, Activin AB, AMPK alpha 2, Activin B, AMPK beta 1, Activin C, AMPK beta 2, Activin RIA/ALK-2, Androgen R/NR3C4, Activin RIB/ALK-4, Angiogenin, Activin RIIA, Angiopoietin-1, Activin RIM, Angiopoietin-2, ADAMS, Angiopoietin-3, ADAMS, Angiopoietin-4, ADAM10, Angiopoietin-like 1, ADAM12, Angiopoietin-like 2, ADAM15, Angiopoietin-like 3, TACE/ADAM17, Angiopoietin-like 4, ADAM19, Angiopoietin-like 7/CDT6, ADAM33, Angiostatin, ADAMTS4, Annexin A1/Annexin I, ADAMTSS, Annexin A7, ADAMTS1, Annexin A10, ADAMTSL-1/Punctin, Annexin V, Adiponectin/Acrp30, ANP, AEBSF, AP Site, Aggrecan, APAF-I, Agrin, APC, AgRP, APE, AGTR-2, APJ, AIF, APLP-I, Akt, APLP-2, Aktl, Apolipoprotein AI, Akt2, Apolipoprotein B, Akt3, APP, Serum Albumin, APRIL/TNFSF13, ALCAM, ARC, ALK-I, Artemin, ALK-7, Arylsulfatase AJARSA, Alkaline Phosphatase, ASAH2/N-acylsphingosine Amidohydrolase-2, alpha 2u-Globulin, ASC, alpha-1-Acid Glycoprotein, ASGR1, alpha-Fetoprotein, ASK1, ALS, ATM, Ameloblastic ATRIP, AMICA/JAML, Aurora A, AMIGO, Aurora B, AMIG02, Axin-1, AMIG03, AxI, Aminoacylase/ACY1, Azurocidin/CAP37/HBP, Aminopeptidase A/ENPEP, B4GALT1, BIM, B7-1/CD80, 6-Biotin-17-NAD, B7-2/CD86, BLAME/SLAMF8, B7-H1/PD-L1, CXCL13/BLC/BCA-1, B7-H2, BLIMP1, B7-H3, Mk, B7-H4, BMI-I, BACE-I, BMP-1/PCP, BACE-2, BMP-2, Bad, BMP-3, BAFF/TNFSF13B, BMP-3b/GDF-10, BAFF R/TNFRSF 13C, BMP-4, Bag-1, BMP-5, BAK, BMP-6, BAMBI/NMA, BMP-7, BARD 1, BMP-8, Bax, BMP-9, BCAM, BMP-10, Bcl-10, BMP-15/GDF-9B, Bcl-2, BMPR-IA/ALK-3, Bcl-2 related protein A1, BMPR-IB/ALK-6, Bcl-w, BMPR-II, Bcl-x, BNIP3L, Bcl-xL, BOC, BCMA/TNFRSF17, BOK, BDNF, BPDE, Benzamide, Brachyury, Common beta Chain, B-Raf, beta IG-H3, CXCL14/BRAK, Betacellulin, BRCA1, beta-Defensin 2, BRCA2, BID, BTLA, Biglycan, Bub-1, Bik-like Killer Protein, c-jun, CD90/Thyl, c-Rel, CD94, CCL6/C10, CD97, CIq R1/CD93, CD151, CIqTNF1, CD160, ClqTNF4, CD163, ClqTNF5, CD164, Complement Component CIr, CD200, Complement Component CIs, CD200 R1, Complement Component C2, CD229/SLAMF3, Complement Component C3a, CD23/Fc epsilon RII, Complement Component C3d, CD2F-10/SLAMF9, Complement Component C5a, CD5L, Cadherin-4/R-Cadherin, CD69, Cadherin-6, CDC2, Cadherin-8, CDC25A, Cadherin-11, CDC25B, Cadherin-12, CDCP1, Cadherin-13, CDO, Cadherin-17, CDX4, E-Cadherin, CEACAM-1/CD66a, N-Cadherin, CEACAM-6, P-Cadherin, Cerberus 1, VE-Cadherin, CFTR, Calbindin D, cGMP, Calcineurin A, Chem R23, Calcineurin B, Chemerin, Calreticulin-2, Chemokine Sampler Packs, CaM Kinase II, Chitinase 3-like 1, cAMP, Chitotriosidase/CHIT1, Cannabinoid R1, Chkl, Cannabinoid R2/CB2/CNR2, Chk2, CAR/NR1I3, CHL-1/L1CAM-2, Carbonic Anhydrase I, Choline Acetyltransferase/CbAT, Carbonic Anhydrase II, Chondrolectin, Carbonic Anhydrase III, Chordin, Carbonic Anhydrase IV, Chordin-Like 1, Carbonic Anhydrase VA, Chordin-Like 2, Carbonic Anhydrase VB, CINC-I, Carbonic Anhydrase VI, CINC-2, Carbonic Anhydrase VII, CINC-3, Carbonic Anhydrase VIII, Claspin, Carbonic Anhydrase IX, Claudin-6, Carbonic Anhydrase X, CLC, Carbonic Anhydrase XII, CLEC-I, Carbonic Anhydrase XIII, CLEC-2, Carbonic Anhydrase XIV, CLECSF 13/CLEC4F, Carboxymethyl Lysine, CLECSF8, Carboxypeptidase A1/CPA1, CLF-I, Carboxypeptidase A2, CL-P1/COLEC12, Carboxypeptidase A4, Clusterin, Carboxypeptidase B1, Clusterin-like 1, Carboxypeptidase E/CPE, CMG-2, Carboxypeptidase X1, CMV UL146, Cardiotrophin-1, CMV UL147, Carnosine Dipeptidase 1, CNP, Caronte, CNTF, CART, CNTF R alpha, Caspase, Coagulation Factor II/Thrombin, Caspase-1, Coagulation Factor I11/Tissue Factor, Caspase-2, Coagulation Factor VII, Caspase-3, Coagulation Factor X, Caspase-4, Coagulation Factor XI, Caspase-6, Coagulation Factor XIV/Protein C, Caspase-7, COCO, Caspase-8, Cohesin, Caspase-9, Collagen I, Caspase-10, Collagen II, Caspase-12, Collagen IV, Caspase-13, Common gamma Chain/IL-2 R gamma, Caspase Peptide Inhibitors, COMP/Thrombospondin-5, Catalase, Complement Component CIrLP, beta-Catenin, Complement Component CIqA, Cathepsin 1, Complement Component CIqC, Cathepsin 3, Complement Factor D, Cathepsin 6, Complement Factor I, Cathepsin A, Complement MASP3, Cathepsin B, Connexin 43, Cathepsin C/DPPI, Contactin-1, Cathepsin D, Contactin-2/TAG1, Cathepsin E, Contactin-4, Cathepsin F, Contactin-5, Cathepsin H, Corin, Cathepsin L, Cornulin, Cathepsin O, CORS26/ClqTNF,3, Cathepsin S, Rat Cortical Stem Cells, Cathepsin V, Cortisol, Cathepsin XITJ?, COUP-TF I/NR2F1, CBP, COUP-TF II/NR2F2, CCI, COX—I, CCK-A R, COX-2, CCL28, CRACC/SLAMF7, CCR1, C-Reactive Protein, CCR2, Creatine Kinase, Muscle/CKMM, CCR3, Creatinine, CCR4, CREB, CCR5, CREG, CCR6, CRELD1, CCR7, CRELD2, CCR8, CRHBP, CCR9, CRHR-I, CCR1O, CRIM1, CD155/PVR, Cripto, CD2, CRISP-2, CD3, CRISP-3, CD4, Crossveinless-2, CD4+/45RA−, CRTAM, CD4+/45RO, CRTH-2, CD4+/CD62L−/CD44, CRY1, CD4+/CD62L+/CD44, Cryptic, CDS, CSB/ERCC6, CD6, CCL27/CTACK, CD8, CTGF/CCN2, CD8+/45RA−, CTLA-4, CD8+/45RO−, Cubilin, CD9, CX3CR1, CD14, CXADR, CD27/TNFRSF7, CXCL16, CD27 Ligand/TNFSF7, CXCR3, CD28, CXCR4, CD30/TNFRSF8, CXCRS, CD30 Ligand/TNFSF8, CXCR6, CD31/PECAM-1, Cyclophilin A, CD34, Cyr61/CCN1, CD36/SR-B3, Cystatin A, CD38, Cystatin B, CD40/TNFRSF5, Cystatin C, CD40 Ligand/TNFSFS, Cystatin D, CD43, Cystatin E/M, CD44, Cystatin F, CD45, Cystatin H, CD46, Cystatin H2, CD47, Cystatin S, CD48/SLAMF2, Cystatin SA, CD55/DAF, Cystatin SN, CD58/LFA-3, Cytochrome c, CD59, Apocytochrome c, CD68, Holocytochrome c, CD72, Cytokeratin 8, CD74, Cytokeratin 14, CD83, Cytokeratin 19, CD84/SLAMFS, Cytonin, D6, DISP1, DAN, Dkk-1, DANCE, Dkk-2, DARPP-32, Dkk-3, DAX1/NROB1, Dkk-4, DCC, DLEC, DCIR/CLEC4A, DLL1, DCAR, DLL4, DcR3/TNFRSF6B, d-Luciferin, DC-SIGN, DNA Ligase IV, DC-SIGNR/CD299, DNA Polymerase beta, DcTRAIL R1/TNFRSF23, DNAM-I, DcTRAIL R2/TNFRSF22, DNA-PKcs, DDR1, DNER, DDR2, Dopa Decarboxylase/DDC, DEC-205, DPCR-I, Decapentaplegic, DPP6, Decorin, DPP A4, Dectin-1/CLEC7A, DPPAS/ESG1, Dectin-2/CLEC6A, DPPII/QPP/DPP7, DEP-1/CD148, DPPIV/CD26, Desert Hedgehog, DR3/TNFRSF25, Desmin, DR6/TNFRSF21, Desmoglein-1, DSCAM, Desmoglein-2, DSCAM-L1, Desmoglein-3, DSPG3, Dishevelled-1, Dtk, Dishevelled-3, Dynamin, EAR2/NR2F6, EphA5, ECE-I, EphA6, ECE-2, EphA7, ECF-L/CHI3L3, EphA8, ECM-I, EphB1, Ecotin, EphB2, EDA, EphB3, EDA-A2, EphB4, EDAR, EphB6, EDG-I, Ephrin, EDG-5, Ephrin-A1, EDG-8, Ephrin-A2, eEF-2, Ephrin-A3, EGF, Ephrin-A4, EGF R, Ephrin-A5, EGR1, Ephrin-B, EG-VEGF/PK1, Ephrin-B1, eIF2 alpha, Ephrin-B2, eIF4E, Ephrin-B3, Elk-I, Epigen, EMAP-II, Epimorphin/Syntaxin 2, EMMPRIN/CD147, Epiregulin, CXCLS/ENA, EPR-1/Xa Receptor, Endocan, ErbB2, Endoglin/CD105, ErbB3, Endoglycan, ErbB4, Endonuclease III, ERCC1, Endonuclease IV, ERCC3, Endonuclease V, ERK1/ERK2, Endonuclease VIII, ERK1, Endorepellin/Perlecan, ERK2, Endostatin, ERK3, Endothelin-1, ERK5/BMK1, Engrailed-2, ERR alpha/NR3B1, EN-RAGE, ERR beta/NR3B2, Enteropeptidase/Enterokinase, ERR gamma/NR3B3, CCL1 1/Eotaxin, Erythropoietin, CCL24/Eotaxin-2, Erythropoietin R, CCL26/Eotaxin-3, ESAM, EpCAM/TROP-1, ER alpha/NR3A1, EPCR, ER beta/NR3A2, Eph, Exonuclease III, EphAl, Exostosin-like 2/EXTL2, EphA2, Exostosin-like 3/EXTL3, EphA3, FABP1, FGF-BP, FABP2, FGF R1-4, FABP3, FGF R1, FABP4, FGF R2, FABP5, FGF R3, FABP7, FGF R4, FABP9, FGF R5, Complement Factor B, Fgr, FADD, FHR5, FAM3A, Fibronectin, FAM3B, Ficolin-2, FAM3C, Ficolin-3, FAM3D, FITC, Fibroblast Activation Protein alpha/FAP, FKBP38, Fas/TNFRSF6, Flap, Fas Ligand/TNFSF6, FLIP, FATP1, FLRG, FATP4, FLRT1, FATP5, FLRT2, Fc gamma R1/CD64, FLRT3, Fc gamma RIIB/CD32b, Flt-3, Fc gamma RIIC/CD32c, Flt-3 Ligand, Fc gamma RIIA/CD32a, Follistatin, Fc gamma RIII/CD16, Follistatin-like 1, FcRH1/IRTA5, FosB/GOS3, FcRH2/IRTA4, FoxD3, FcRH4/IRTA1, FoxJ1, FcRH5/IRTA2, FoxP3, Fc Receptor-like 3/CD16-2, Fpg, FEN-I, FPR1, Fetuin A, FPRL1, Fetuin B, FPRL2, FGF acidic, CX3CL1/Fractalkine, FGF basic, Frizzled-1, FGF-3, Frizzled-2, FGF-4, Frizzled-3, FGF-5, Frizzled-4, FGF-6, Frizzled-5, FGF-8, Frizzled-6, FGF-9, Frizzled-7, FGF-IO, Frizzled-8, FGF-11, Frizzled-9, FGF-12, Frk, FGF-13, sFRP-1, FGF-16, sFRP-2, FGF-17, sFRP-3, FGF-19, sFRP-4, FGF-20, Furin, FGF-21, FXR/NR1H4, FGF-22, Fyn, FGF-23, G9a/EHMT2, GFR alpha-3/GDNF R alpha-3, GABA-A-R alpha 1, GFR alpha-4/GDNF R alpha-4, GABA-A-R alpha 2, GITR/TNFRSF18, GABA-A-R alpha 4, GITR Ligand/TNFSF18, GABA-A-R alpha 5, GLI-I, GABA-A-R alpha 6, GLI-2, GABA-A-R beta 1, GLP/EHMT1, GABA-A-R beta 2, GLP-I R, GABA-A-R beta 3, Glucagon, GABA-A-R gamma 2, Glucosamine (N-acetyl)-6-Sulfatase/GNS, GABA-B-R2, GIuR1, GAD1/GAD67, GluR2/3, GAD2/GAD65, GluR2, GADD45 alpha, GluR3, GADD45 beta, Glutl, GADD45 gamma, Glut2, Galectin-1, Glut3, Galectin-2, Glut4, Galectin-3, Glut5, Galectin-3 BP, Glutaredoxin 1, Galectin-4, Glycine R, Galectin-7, Glycophorin A, Galectin-8, Glypican 2, Galectin-9, Glypican 3, GalNAc4S-6ST, Glypican 5, GAP-43, Glypican 6, GAPDH, GM-CSF, Gas1, GM-CSF R alpha, Gas6, GMF-beta, GASP-1/WFIKKNRP, gp130, GASP-2/WFIKKN, Glycogen Phosphorylase BB/GPBB, GATA-I, GPR15, GATA-2, GPR39, GATA-3, GPVI, GATA-4, GR/NR3C1, GATA-5, Gr-1/Ly-6G, GATA-6, Granulysin, GBL, Granzyme A, GCNF/NR6A1, Granzyme B, CXCL6/GCP-2, Granzyme D, G-CSF, Granzyme G, G-CSF R, Granzyme H, GDF-I, GRASP, GDF-3 GRB2, GDF-5, Gremlin, GDF-6, GRO, GDF-7, CXCL1/GRO alpha, GDF-8, CXCL2/GRO beta, GDF-9, CXCL3/GRO gamma, GDF-11, Growth Hormone, GDF-15, Growth Hormone R, GDNF, GRP75/HSPA9B, GFAP, GSK-3 alpha/beta, GFI-I, GSK-3 alpha, GFR alpha-1/GDNF R alpha-1, GSK-3 beta, GFR alpha-2/GDNF R alpha-2, EZFIT, H2AX, Histidine, H60, HM74A, HAI-I, HMGA2, HAI-2, HMGB1, HAI-2A, TCF-2/HNF-1 beta, HAI-2B, HNF-3 beta/FoxA2, HAND1, HNF-4 alpha/NR2A1, HAPLN1, HNF-4 gamma/NR2A2, Airway Trypsin-like Protease/HAT, HO-1/HMOX1/HSP32, HB-EGF, HO-2/HMOX2, CCL 14a/HCC-1, HPRG, CCL14b/HCC-3, Hrk, CCL16/HCC-4, HRP-I, alpha HCG, HS6ST2, Hck, HSD-I, HCR/CRAM-A/B, HSD-2, HDGF, HSP 10/EPF, Hemoglobin, HSP27, Hepassocin, HSP60, HES-1, HSP70, HES-4, HSP90, HGF, HTRA/Protease Do, HGF Activator, HTRA1/PRSS11, HGF R, HTRA2/0 ml, HIF-I alpha, HVEM/TNFRSF14, HIF-2 alpha, Hyaluronan, HIN-1/Secretoglobulin 3A1, 4-Hydroxynonenal, Hip, CCL1/I-309/TCA-3, IL-IO, cIAP (pan), IL-IO R alpha, cIAP-1/HIAP-1, IL-10 R beta, cIAP-2/HIAP-1, IL-11, IBSP/Sialoprotein II, EL-11 R alpha, ICAM-1/CD54, IL-12, ICAM-2/CD102, IL-12/IL-23 p40, ICAM-3/CD50, IL-12 R beta 1, ICAM-5, IL-12 R beta 2, ICAT, IL-13, ICOS, IL-13 R alpha 1, Iduronate 2-Sulfatase/EOS, IL-13 R alpha 2, EFN, IL-15, IFN-alpha, IL-15 R alpha, IFN-alpha 1, IL-16, IFN-alpha 2, IL-17, IFN-alpha 4b, IL-17 R, IFN-alpha A, IL-17 RC, IFN-alpha B2, IL-17 RD, IFN-alpha C, IL-17B, IFN-alpha D, IL-17B R, IFN-alpha F, IL-17C, IFN-alpha G, IL-17D, IFN-alpha H2, IL-17E, IFN-alpha I, IL-17F, IFN-alpha J1, IL-18/IL-1F4, IFN-alpha K, IL-18 BPa, IFN-alpha WA, IL-18 BPc, IFN-alpha/beta R1, IL-18 BPd, IFN-alpha/beta R2, IL-18 R alpha/IL-1 R5, IFN-beta, IL-18 R beta/IL-1 R7, IFN-gamma, IL-19, IFN-gamma R1, IL-20, IFN-gamma R2, IL-20 R alpha, IFN-omega, IL-20 R beta, IgE, IL-21, IGFBP-I, IL-21 R, IGFBP-2, IL-22, IGFBP-3, IL-22 R, IGFBP-4, IL-22BP, IGFBP-5, IL-23, IGFBP-6, IL-23 R, IGFBP-L1, IL-24, IGFBP-rp1/IGFBP-7, IL-26/AK155, IGFBP-rPIO, IL-27, IGF-I, EL-28A, IGF-I R, IL-28B, IGF-II, IL-29/EFN-lambda 1, IGF-II R, IL-31, IgG, EL-31 RA, IgM, IL-32 alpha, IGSF2, IL-33, IGSF4A/SynCAM, ILT2/CD85J, IGSF4B, ILT3/CD85k, IGSF8, ILT4/CD85d, IgY, ILT5/CD85a, IkB-beta, ILT6/CD85e, IKK alpha, Indian Hedgehog, IKK epsilon, INSRR, EKK gamma, Insulin, IL-1 alpha/IL-IF1, Insulin R/CD220, IL-1 beta/IL-1F2, Proinsulin, IL-1ra/IL-1F3, Insulysin/EDE, IL-1F5/FIL1 delta, Integrin alpha 2/CD49b, IL-1F6/FIL1 epsilon, Integrin alpha 3/CD49c, IL-1F7/FIL1 zeta, Integrin alpha 3 beta 1/VLA-3, IL-1F8/FIL1 eta, Integrin alpha 4/CD49d, IL-1F9/IL-1 H1, Integrin alpha 5/CD49e, IL-1F10/IL-1HY2, Integrin alpha 5 beta 1, IL-I RI, Integrin alpha 6/CD49f, IL-I RII, Integrin alpha 7, IL-I R3/IL-1 R AcP, Integrin alpha 9, IL-I R4/ST2, Integrin alpha E/CD103, IL-I R6/IL-1 R rp2, Integrin alpha L/CD1 Ia, IL-I R8, Integrin alpha L beta 2, IL-I R9, Integrin alpha M/CD1 Ib, IL-2, Integrin alpha M beta 2, IL-2 R alpha, Integrin alpha V/CD51, IL-2 R beta, Integrin alpha V beta 5, IL-3, Integrin alpha V beta 3, IL-3 R alpha, Integrin alpha V beta 6, IL-3 R beta, Integrin alpha XJCD1 Ic, IL-4, Integrin beta 1/CD29, IL-4 R, Integrin beta 2/CD18, IL-5, Integrin beta 3/CD61, IL-5 R alpha, Integrin beta 5, IL-6, Integrin beta 6, IL-6 R, Integrin beta 7, IL-7, CXCL10/EP-10/CRG-2, IL-7 R alpha/CD127, IRAKI, CXCR1/IL-8 RA, IRAK4, CXCR2/IL-8 RB, ERS-I, CXCL8/IL-8, Islet-1, IL-9, CXCL1 1/I-TAC, IL-9 R, Jagged 1, JAM-4/IGSF5, Jagged 2, JNK, JAM-A, JNK1/JNK2, JAM-B/VE-JAM, JNK1, JAM-C, JNK2, Kininogen, Kallikrein 3/PSA, Kininostatin, Kallikrein 4, KER/CD158, Kallikrein 5, KER2D1, Kallikrein 6/Neurosin, KIR2DL3, Kallikrein 7, KIR2DL4/CD158d, Kallikrein 8/Neuropsin, KIR2DS4, Kallikrein 9, KIR3DL1, Plasma Kallikrein/KLKB1, KER3DL2, Kallikrein 10, Kirrel2, Kallikrein 11, KLF4, Kallikrein 12, KLFS, Kallikrein 13, KLF6, Kallikrein 14, Klotho, Kallikrein 15, Klotho beta, KC, KOR, Keapl, Kremen-1, Kell, Kremen-2, KGF/FGF-7, LAG-3, LINGO-2, LAIR1, Lipin 2, LAIR2, Lipocalin-1, Laminin alpha 4, Lipocalin-2/NGAL, Laminin gamma 1,5-Lipoxygenase, Laminin I, LXR alpha/NR1H3, Laminin S, LXR beta/NR1H2, Laminin-1, Livin, Laminin-5, LEX, LAMP, LMIR1/CD300A, Langerin, LMIR2/CD300c, LAR, LMIR3/CD300LF, Latexin, LMIRS/CD300LB, Layilin, LMIR6/CD300LE, LBP, LMO2, LDL R, LOX-1/SR-E1, LECT2, LRH-1/NR5A2, LEDGF, LRIG1, Lefty, LRIG3, Lefty-1, LRP-I, Lefty-A, LRP-6, Legumain, LSECtin/CLEC4G, Leptin, Lumican, Leptin R, CXCL15/Lungkine, Leukotriene B4, XCL1/Lymphotactin, Leukotriene B4 R1, Lymphotoxin, LEF, Lymphotoxin beta/TNFSF3, LIF R alpha, Lymphotoxin beta R/TNFRSF3, LIGHT/TNFSF14, Lyn, Limitin, Lyp, LIM-PII/SR-B2, Lysyl Oxidase Homolog 2, LIN-28, LYVE-I, LINGO-I, alpha 2-Macroglobulin, CXCL9/MIG, MAD2L1, Mimecan, MAdCAM-1, Mindin, MafB, Mineralocorticoid R/NR3C2, MafF, CCL3L1/MIP-1 alpha Isoform LD78 beta, MafG, CCL3/MIP-1 alpha, MafK, CCL4L1/LAG-1, MAG/Siglec-4-a, CCL4/MIP-1 beta, MANF, CCL15/MEP-1 delta, MAP2, CCL9/10/MIP-1 gamma, MAPK, MIP-2, Marapsin/Pancreasin, CCL19/MIP-3 beta, MARCKS, CCL20/MIP-3 alpha, MARCO, MIP-I, Mashl, MIP-II, Matrilin-2, MIP-III, Matrilin-3, MIS/AMH, Matrilin-4, MIS RII, Matriptase/ST14, MIXL1, MBL, MKK3/MKK6, MBL-2, MKK3, Melanocortin 3R/MC3R, MKK4, MCAM/CD146, MKK6, MCK-2, MKK7, McI-I, MKP-3, MCP-6, MLH-I, CCL2/MCP-1, MLK4 alpha, MCP-11, MMP, CCL8/MCP-2, MMP-1, CCL7/MCP-3/MARC, MMP-2, CCL13/MCP-4, MMP-3, CCL12/MCP-5, MMP-7, M-CSF, MMP-8, M-CSF R, MMP-9, MCV-type II, MMP-IO, MD-I, MMP-I 1, MD-2, MMP-12, CCL22/MDC, MMP-13, MDL-1/CLEC5A, MMP-14, MDM2, MMP-15, MEA-I, MMP-16/MT3-MMP, MEK1/MEK2, MMP-24/MT5-MMP, MEK1, MMP-25/MT6-MMP, MEK2, MMP-26, Melusin, MMR, MEPE, MOG, Meprin alpha, CCL23/MPIF-1, Meprin beta, M-Ras/R-Ras3, Mer, Mrel 1, Mesothelin, MRP1 Meteorin, MSK1/MSK2, Methionine Aminopeptidase 1, MSK1, Methionine Aminopeptidase, MSK2, Methionine Aminopeptidase 2, MSP, MFG-E8, MSP R/Ron, MFRP, Mug, MgcRacGAP, MULT-I, MGL2, Musashi-1, MGMT, Musashi-2, MIA, MuSK, MICA, MutY DNA Glycosylase, MICB, MyD88, MICL/CLEC12A, Myeloperoxidase, beta 2 Microglobulin, Myocardin, Midkine, Myocilin, MIF, Myoglobin, NAIP NGFI-B gamma/NR4A3, Nanog, NgR2/NgRH1, CXCL7/NAP-2, NgR3/NgRH2, Nbsl, Nidogen-1/Entactin, NCAM-1/CD56, Nidogen-2, NCAM-L1, Nitric Oxide, Nectin-1, Nitrotyrosine, Nectin-2/CD1 12, NKG2A, Nectin-3, NKG2C, Nectin-4, NKG2D, Neogenin, NKp30, Neprilysin/CDIO, NKp44, Neprilysin-2/MMEL1/MMEL2, NKp46/NCR1, Nestin, NKp80/KLRF1, NETO2, NKX2.5, Netrin-1, NMDA R, NR1 Subunit, Netrin-2, NMDA R, NR2A Subunit, Netrin-4, NMDA R, NR2B Subunit, Netrin-Gla, NMDA R, NR2C Subunit, Netrin-G2a, N-Me-6,7-diOH-TIQ, Neuregulin-1/NRG1, Nodal, Neuregulin-3/NRG3, Noggin, Neuritin, Nogo Receptor, NeuroD1, Nogo-A, Neurofascin, NOMO, Neurogenin-1, Nope, Neurogenin-2, Norrin, Neurogenin-3, eNOS, Neurolysin, iNOS, Neurophysin II, nNOS, Neuropilin-1, Notch-1, Neuropilin-2, Notch-2, Neuropoietin, Notch-3, Neurotrimin, Notch-4, Neurturin, NOV/CCN3, NFAM1, NRAGE, NF-H, NrCAM, NFkB1, NRL, NFkB2, NT-3, NF-L, NT-4, NF-M, NTB-A/SLAMF6, NG2/MCSP, NTH1, NGF R/TNFRSF16, Nucleostemin, beta-NGF, Nurr-1/NR4A2, NGFI-B alpha/NR4A1, OAS2, Orexin B, OBCAM, OSCAR, OCAM, OSF-2/Periostin, OCIL/CLEC2d, Oncostatin M/OSM, OCILRP2/CLEC21, OSM R beta, Oct-3/4, Osteoactivin/GPNMB, OGG1, Osteoadherin, Olig 1, 2, 3, Osteocalcin, Oligl, Osteocrin, Olig2, Osteopontin, Olig3, Osteoprotegerin/TNFRSF1 IB, Oligodendrocyte Marker 01, Otx2, Oligodendrocyte Marker O4, OV-6, OMgp, OX40/TNFRSF4, Opticin, OX40 Ligand/TNFSF4, Orexin A, OAS2, Orexin B, OBCAM, OSCAR, OCAM, OSF-2/Periostin, OCIL/CLEC2d, Oncostatin M/OSM, OCILRP2/CLEC2i, OSM R beta, Oct-3/4, Osteoactivin/GPNMB, OGG1, Osteoadherin, Olig 1, 2, 3, Osteocalcin, Oligl, Osteocrin, Olig2, Osteopontin, Olig3, Osteoprotegerin/TNFRSF1 IB, Oligodendrocyte Marker 01, Otx2, Oligodendrocyte Marker 04, OV-6, OMgp, OX40/TNFRSF4, Opticin, OX40 Ligand/TNFSF4, Orexin A, RACK1, Ret, Rad1, REV-ERB alpha/NR1D1, Rad17, REV-ERB beta/NR1D2, Rad51, Rex-1, Rae-1, RGM-A, Rae-1 alpha, RGM-B, Rae-1 beta, RGM-C, Rae-1 delta, Rheb, Rae-1 epsilon, Ribosomal Protein S6, Rae-1 gamma, RIP1, Raf-1, ROBO1, RAGE, ROBO2, Ra1A/Ra1B, R0B03, RaIA, ROBO4, RaIB, R0R/NR1F1-3 (pan), RANK/TNFRSF1 1A, ROR alpha/NR1F1, CCL5/RANTES, ROR gamma/NR1F3, Rap1A/B, RTK-like Orphan Receptor 1/ROR1, RAR alpha/NR1B1, RTK-like Orphan Receptor 2/ROR2, RAR beta/NR1B2, RP105, RAR gamma/NR1B3, RP A2, Ras, RSK (pan), RBP4, RSK1/RSK2, RECK, RSK1, Reg 2/PAP, RSK2, Reg I, RSK3, Reg II, RSK4, Reg III, R-Spondin 1, Reg Iia, R-Spondin 2, Reg IV, R-Spondin 3, Relaxin-1, RUNX1/CBFA2, Relaxin-2, RUNX2/CBFA1, Relaxin-3, RUNX3/CBFA3, RELM alpha, RXR alpha/NR2B1, RELM beta, RXR beta/NR2B2, RELT/TNFRSF19L, RXR gamma/NR2B3, Resistin, S1OOAlO, SLITRK5, S100A8, SLPI, S100A9, SMAC/Diablo, S1OOB, Smadl, S1OOP, Smad2, SALL1, Smad3, delta-Sarcoglycan, Smad4, Sca-1/Ly6, Smad5, SCD-I, Smad7, SCF, Smad8, SCF R/c-kit, SMC1, SCGF, alpha-Smooth Muscle Actin, SCL/Tall, SMUG1, SCP3/SYCP3, Snail, CXCL12/SDF-1, Sodium Calcium Exchanger 1, SDNSF/MCFD2, Soggy-1, alpha-Secretase, Sonic Hedgehog, gamma-Secretase, S or CS1, beta-Secretase, S or CS3, E-Selectin, Sortilin, L-Selectin, SOST, P-Selectin, SOX1, Semaphorin 3A, SOX2, Semaphorin 3C, SOX3, Semaphorin 3E, SOX7, Semaphorin 3F, SOX9, Semaphorin 6A, SOX1O, Semaphorin 6B, SOX 17, Semaphorin 6C, SOX2 Semaphorin 6D, SPARC, Semaphorin 7 A, SPARC-like 1, Separase, SP-D, Serine/Threonine Phosphatase Substrate I, Spinesin, Serpin A1, F-Spondin, Serpin A3, SR-AI/MSR, Serpin A4/Kallistatin, Src, Serpin A5/Protein C Inhibitor, SREC-I/SR-F1, Serpin A8/Angiotensinogen, SREC-II, Serpin B5, SSEA-I, Serpin C1/Antithrombin-III, SSEA-3, Serpin D1/Heparin Cofactor II, SSEA-4, Serpin E1/PAI-1, ST7/LRP12, Serpin E2, Stabilin-1, Serpin F1, Stabilin-2, Serpin F2, Stanniocalcin 1, Serpin G1/C1 Inhibitor, Stanniocalcin 2, Serpin 12, STAT1, Serum Amyloid A1, STAT2, SF-1/NR5A1, STATS, SGK, STAT4, SHBG, STAT5a/b, SHIP, STAT5a, SHP/NROB2, STAT5b, SHP-I, STATE, SHP-2, VE-Statin, SIGIRR, Stella/Dppa3, Siglec-2/CD22, STRO-I, Siglec-3/CD33, Substance P, Siglec-5, Sulfamidase/SGSH, Siglec-6, Sulfatase Modifying Factor 1/SUMF1, Siglec-7, Sulfatase Modifying Factor 2/SUMF2, Siglec-9, SUMO1, Siglec-10, SUMO2/3/4, Siglec-11, SUMO3, Siglec-F, Superoxide Dismutase, SIGNR1/CD209, Superoxide Dismutase-1/Cu[0099]-Zn SOD, SIGNR4, Superoxide Dismutase-2/Mn-SOD, SIRP beta 1, Superoxide Dismutase-3/EC-SOD, SKI, Surviving, SLAM/CD150, Synapsin I, Sleeping Beauty Transposase, Syndecan-I/CD 138, Slit3, Syndecan-2, SLITRK1, Syndecan-3, SLITRK2, Syndecan-4, SLITRK4, TACI/TNFRSF13B, TMEFF 1/Tomoregulin-1, TAO2, TMEFF2, TAPP1, TNF-alpha/TNFSF IA, CCL17/TARC, TNF-beta/TNFSF1B, Tau, TNF R1/TNFRSFIA, TC21/R-Ras2, TNF RII/TNFRSF1B, TCAM-I, TOR, TCCR/WSX-1, TP-I, TC-PTP, TP63/TP73L, TDG, TR, CCL25/TECK, TR alpha/NR1A1, Tenascin C, TR beta 1/NR1A2, Tenascin R, TR2/NR2C1, TER-119, TR4/NR2C2, TERT, TRA-1-85, Testican 1/SPOCK1, TRADD, Testican 2/SPOCK2,TRAF-1, Testican 3/SPOCK3, TRAF-2, TFPI, TRAF-3, TFPI-2, TRAF-4, TGF-alpha, TRAF-6, TGF-beta, TRAIL/TNFSF10, TGF-beta 1, TRAIL R1/TNFRSFIOA, LAP (TGF-beta 1), TRAIL R2/TNFRSF10B, Latent TGF-beta 1, TRAIL R3/TNFRSF10C, TGF-beta 1.2, TRAIL R4/TNFRSF10D, TGF-beta 2, TRANCE/TNFSF1 1, TGF-beta 3, TfR (Transferrin R), TGF-beta 5, Apo-Transferrin, Latent TGF-beta by 1, Holo-Transferrin, Latent TGF-beta bp2, Trappin-2/Elafin, Latent TGF-beta bp4, TREM-1, TGF-beta R1/ALK-5, TREM-2, TGF-beta R11, TREM-3, TGF-beta RIIb, TREML1/TLT-1, TGF-beta RIII, TRF-I, Thermolysin, TRF-2, Thioredoxin-1, TRH-degrading Ectoenzyme/TRHDE, Thioredoxin-2, TRIMS, Thioredoxin-80, Tripeptidyl-Peptidase I, Thioredoxin-like 5/TRP14, TrkA, THOP1, TrkB, Thrombomodulin/CD141, TrkC, Thrombopoietin, TROP-2, Thrombopoietin R, Troponin I Peptide 3, Thrombospondin-1, Troponin T, Thrombospondin-2, TROY/TNFRSF 19, Thrombospondin-4, Trypsin 1, Thymopoietin, Trypsin 2/PRSS2, Thymus Chemokine-1, Trypsin 3/PRSS3, Tie-1, Tryptase-5/Prss32, Tie-2, Tryptase alpha/TPS1, TIM-I/KIM-I/HAVCR, Tryptase beta-1/MCPT-7, TIM-2, Tryptase beta-2/TPSB2, TIM-3, Tryptase epsilon/BSSP-4, TIM-4, Tryptase gamma-1/TPSG1, TIM-5, Tryptophan Hydroxylase, TIM-6, TSC22, TIMP-I, TSG, TIMP-2, TSG-6, TIMP-3, TSK, TIMP-4, TSLP, TL1A/TNFSF15, TSLP R, TLR1, TSP50, TLR2, beta-III Tubulin, TLR3, TWEAK/TNFSF12, TLR4, TWEAK R/TNFRSF 12, TLR5, Tyk2, TLR6, Phospho-Tyrosine, TLR9, Tyrosine Hydroxylase, TLX/NR2E1, Tyrosine Phosphatase Substrate I, Ubiquitin, UNC5H3, Ugi, UNC5H4, UGRP1, UNG, ULBP-I, uPA, ULBP-2, uPAR, ULBP-3, URB, UNC5H1, UVDE, UNC5H2, Vanilloid R1, VEGF R, VASA, VEGF R1/Flt-1, Vasohibin, VEGF R2/KDR/Flk-1, Vasorin, VEGF R3/FU-4, Vasostatin, Versican, Vav-1, VG5Q, VCAM-1, VHR, VDR/NR1I1, Vimentin, VEGF, Vitronectin, VEGF-B, VLDLR, VEGF-C, vWF-A2, VEGF-D, Synuclein-alpha, Ku70, WASP, Wnt-7b, WIF-I, Wnt-8a WISP-1/CCN4, Wnt-8b, WNK1, Wnt-9a, Wnt-1, Wnt-9b, Wnt-3a, Wnt-10a, Wnt-4, Wnt-10b, Wnt-5a, Wnt-11, Wnt-5b, wnvNS3, Wnt7a, XCR1, XPE/DDB1, XEDAR, XPE/DDB2, Xg, XPF, XIAP, XPG, XPA, XPV, XPD, XRCC1, Yes, YY1, EphA4.

Numerous human ion channels are targets of particular interest. Non-limiting examples include 5-hydroxytryptamine 3 receptor B subunit, 5-hydroxytryptamine 3 receptor precursor, 5-hydroxytryptamine receptor 3 subunit C, AAD 14 protein, Acetylcholine receptor protein, alpha subunit precursor, Acetylcholine receptor protein, beta subunit precursor, Acetylcholine receptor protein, delta subunit precursor, Acetylcholine receptor protein, epsilon subunit precursor, Acetylcholine receptor protein, gamma subunit precursor, Acid sensing ion channel 3 splice variant b, Acid sensing ion channel 3 splice variant c, Acid sensing ion channel 4, ADP-ribose pyrophosphatase, mitochondrial precursor, Alphal A-voltage-dependent calcium channel, Amiloride-sensitive cation channel 1, neuronal, Amiloride-sensitive cation channel 2, neuronal Amiloride-sensitive cation channel 4, isoform 2, Amiloride-sensitive sodium channel, Amiloride-sensitive sodium channel alpha-subunit, Amiloride-sensitive sodium channel beta-subunit, Amiloride-sensitive sodium channel delta-subunit, Amiloride-sensitive sodium channel gamma-subunit, Annexin A7, Apical-like protein, ATP-sensitive inward rectifier potassium channel 1, ATP-sensitive inward rectifier potassium channel 10, ATP-sensitive inward rectifier potassium channel 11, ATP-sensitive inward rectifier potassium channel 14, ATP-sensitive inward rectifier potassium channel 15, ATP-sensitive inward rectifier potassium channel 8, Calcium channel alpha12.2 subunit, Calcium channel alpha12.2 subunit, Calcium channel alpha1E subunit, delta19 delta40 delta46 splice variant, Calcium-activated potassium channel alpha subunit 1, Calcium-activated potassium channel beta subunit 1, Calcium-activated potassium channel beta subunit 2, Calcium-activated potassium channel beta subunit 3, Calcium-dependent chloride channel-1, Cation channel TRPM4B, CDNA FLJ90453 fis, clone NT2RP3001542, highly similar to Potassium channel tetramerisation domain containing 6, CDNA FLJ90663 fis, clone PLACE 1005031, highly similar to Chloride intracellular channel protein 5, CGMP-gated cation channel beta subunit, Chloride channel protein, Chloride channel protein 2, Chloride channel protein 3, Chloride channel protein 4, Chloride channel protein 5, Chloride channel protein 6, Chloride channel protein C1C-Ka, Chloride channel protein C1C-Kb, Chloride channel protein, skeletal muscle, Chloride intracellular channel 6, Chloride intracellular channel protein 3, Chloride intracellular channel protein 4, Chloride intracellular channel protein 5, CHRNA3 protein, Clcn3e protein, CLCNKB protein, CNGA4 protein, Cullin-5, Cyclic GMP gated potassium channel, Cyclic-nucleotide-gated cation channel 4, Cyclic-nucleotide-gated cation channel alpha 3, Cyclic-nucleotide-gated cation channel beta 3, Cyclic-nucleotide-gated olfactory channel, Cystic fibrosis transmembrane conductance regulator, Cytochrome B-245 heavy chain, Dihydropyridine-sensitive L-type, calcium channel alpha-2/delta subunits precursor, FXYD domain-containing ion transport regulator 3 precursor, FXYD domain-containing ion transport regulator 5 precursor, FXYD domain-containing ion transport regulator 6 precursor, FXYD domain-containing ion transport regulator 7, FXYD domain-containing ion transport regulator 8 precursor, G protein-activated inward rectifier potassium channel 1, G protein-activated inward rectifier potassium channel 2, G protein-activated inward rectifier potassium channel 3, G protein-activated inward rectifier potassium channel 4, Gamma-aminobutyric-acid receptor alpha-1 subunit precursor, Gamma-aminobutyric-acid receptor alpha-2 subunit precursor, Gamma-aminobutyric-acid receptor alpha-3 subunit precursor, Gamma-aminobutyric-acid receptor alpha-4 subunit precursor, Gamma-aminobutyric-acid receptor alpha-5 subunit precursor, Gamma-aminobutyric-acid receptor alpha-6 subunit precursor, Gamma-aminobutyric-acid receptor beta-1 subunit precursor, Gamma-aminobutyric-acid receptor beta-2 subunit precursor, Gamma-aminobutyric-acid receptor beta-3 subunit precursor, Gamma-aminobutyric-acid receptor delta subunit precursor, Gamma-aminobutyric-acid receptor epsilon subunit precursor, Gamma-aminobutyric-acid receptor gamma-1 subunit precursor, Gamma-aminobutyric-acid receptor gamma-3 subunit precursor, Gamma-aminobutyric-acid receptor pi subunit precursor, Gamma-aminobutyric-acid receptor rho-1 subunit precursor, Gamma-aminobutyric-acid receptor rho-2 subunit precursor, Gamma-aminobutyric-acid receptor theta subunit precursor, GluR6 kainate receptor, Glutamate receptor 1 precursor, Glutamate receptor 2 precursor, Glutamate receptor 3 precursor, Glutamate receptor 4 precursor, Glutamate receptor 7, Glutamate receptor B, Glutamate receptor delta-1 subunit precursor, Glutamate receptor, ionotropic kainate 1 precursor, Glutamate receptor, ionotropic kainate 2 precursor, Glutamate receptor, ionotropic kainate 3 precursor, Glutamate receptor, ionotropic kainate 4 precursor, Glutamate receptor, ionotropic kainate 5 precursor, Glutamate [NMDA] receptor subunit 3A precursor, Glutamate [NMDA] receptor subunit 3B precursor, Glutamate [NMDA] receptor subunit epsilon 1 precursor, Glutamate [NMDA] receptor subunit epsilon 2 precursor, Glutamate [NMDA] receptor subunit epsilon 4 precursor, Glutamate [NMDA] receptor subunit zeta 1 precursor, Glycine receptor alpha-1 chain precursor, Glycine receptor alpha-2 chain precursor, Glycine receptor alpha-3 chain precursor, Glycine receptor beta chain precursor, H/ACA ribonucleoprotein complex subunit 1, High affinity immunoglobulin epsilon receptor beta-subunit, Hypothetical protein DKFZp31310334, Hypothetical protein DKFZp761M1724, Hypothetical protein FLJ12242, Hypothetical protein FLJ14389, Hypothetical protein FLJ14798, Hypothetical protein FLJ14995, Hypothetical protein FLJ16180, Hypothetical protein FLJ16802, Hypothetical protein FLJ32069, Hypothetical protein FLJ37401, Hypothetical protein FLJ38750, Hypothetical protein FLJ40162, Hypothetical protein FLJ41415, Hypothetical protein FLJ90576, Hypothetical protein FLJ90590, Hypothetical protein FLJ90622, Hypothetical protein KCTD15, Hypothetical protein MGC15619, Inositol 1,4,5-trisphosphate receptor type 1, Inositol 1,4,5-trisphosphate receptor type 2, Inositol 1,4,5-trisphosphate receptor type 3, Intermediate conductance calcium-activated potassium channel protein 4, Inward rectifier potassium channel 13, Inward rectifier potassium channel 16, Inward rectifier potassium channel 4, Inward rectifying K(+) channel negative regulator Kir2.2v, Kainate receptor subunit KA2a, KCNH5 protein, KCTD 17 protein, KCTD2 protein, Keratinocytes associated transmembrane protein 1, Kv channel-interacting protein 4, Melastatin 1, Membrane protein MLC1, MGC 15619 protein, Mucolipin-1, Mucolipin-2, Mucolipin-3, Multidrug resistance-associated protein 4, N-methyl-D-aspartate receptor 2C subunit precursor, NADPH oxidase homolog 1, Nav1.5, Neuronal acetylcholine receptor protein, alpha-10 subunit precursor, Neuronal acetylcholine receptor protein, alpha-2 subunit precursor, Neuronal acetylcholine receptor protein, alpha-3 subunit precursor, Neuronal acetylcholine receptor protein, alpha-4 subunit precursor, Neuronal acetylcholine receptor protein, alpha-5 subunit precursor, Neuronal acetylcholine receptor protein, alpha-6 subunit precursor, Neuronal acetylcholine receptor protein, alpha-7 subunit precursor, Neuronal acetylcholine receptor protein, alpha-9 subunit precursor, Neuronal acetylcholine receptor protein, beta-2 subunit precursor, Neuronal acetylcholine receptor protein, beta-3 subunit precursor, Neuronal acetylcholine receptor protein, beta-4 subunit precursor, Neuronal voltage-dependent calcium channel alpha 2D subunit, P2X purinoceptor 1, P2X purinoceptor 2, P2X purinoceptor 3, P2X purinoceptor 4, P2X purinoceptor 5, P2X purinoceptor 6, P2X purinoceptor 7, Pancreatic potassium channel TALK-Ib, Pancreatic potassium channel TALK-Ic, Pancreatic potassium channel TALK-Id, Phospholemman precursor, Plasmolipin, Polycystic kidney disease 2 related protein, Polycystic kidney disease 2-like 1 protein, Polycystic kidney disease 2-like 2 protein, Polycystic kidney disease and receptor for egg jelly related protein precursor, Polycystin-2, Potassium channel regulator, Potassium channel subfamily K member 1, Potassium channel subfamily K member 10, Potassium channel subfamily K member 12, Potassium channel subfamily K member 13, Potassium channel subfamily K member 15, Potassium channel subfamily K member 16, Potassium channel subfamily K member 17, Potassium channel subfamily K member 2, Potassium channel subfamily K member 3, Potassium channel subfamily K member 4, Potassium channel subfamily K member 5, Potassium channel subfamily K member 6, Potassium channel subfamily K member 7, Potassium channel subfamily K member 9, Potassium channel tetramerisation domain containing 3, Potassium channel tetramerisation domain containing protein 12, Potassium channel tetramerisation domain containing protein 14, Potassium channel tetramerisation domain containing protein 2, Potassium channel tetramerisation domain containing protein 4, Potassium channel tetramerisation domain containing protein 5, Potassium channel tetramerization domain containing 10, Potassium channel tetramerization domain containing protein 13, Potassium channel tetramerization domain-containing 1, Potassium voltage-gated channel subfamily A member 1, Potassium voltage-gated channel subfamily A member 2, Potassium voltage-gated channel subfamily A member 4, Potassium voltage-gated channel subfamily A member 5, Potassium voltage-gated channel subfamily A member 6, Potassium voltage-gated channel subfamily B member 1, Potassium voltage-gated channel subfamily B member 2, Potassium voltage-gated channel subfamily C member 1, Potassium voltage-gated channel subfamily C member 3, Potassium voltage-gated channel subfamily C member 4, Potassium voltage-gated channel subfamily D member 1, Potassium voltage-gated channel subfamily D member 2, Potassium voltage-gated channel subfamily D member 3, Potassium voltage-gated channel subfamily E member 1, Potassium voltage-gated channel subfamily E member 2, Potassium voltage-gated channel subfamily E member 3, Potassium voltage-gated channel subfamily E member 4, Potassium voltage-gated channel subfamily F member 1, Potassium voltage-gated channel subfamily G member 1, Potassium voltage-gated channel subfamily G member 2, Potassium voltage-gated channel subfamily G member 3, Potassium voltage-gated channel subfamily G member 4, Potassium voltage-gated channel subfamily H member 1, Potassium voltage-gated channel subfamily H member 2, Potassium voltage-gated channel subfamily H member 3, Potassium voltage-gated channel subfamily H member 4, Potassium voltage-gated channel subfamily H member 5, Potassium voltage-gated channel subfamily H member 6, Potassium voltage-gated channel subfamily H member 7, Potassium voltage-gated channel subfamily H member 8, Potassium voltage-gated channel subfamily KQT member 1, Potassium voltage-gated channel subfamily KQT member 2, Potassium voltage-gated channel subfamily KQT member 3, Potassium voltage-gated channel subfamily KQT member 4, Potassium voltage-gated channel subfamily KQT member 5, Potassium voltage-gated channel subfamily S member 1, Potassium voltage-gated channel subfamily S member 2, Potassium voltage-gated channel subfamily S member 3, Potassium voltage-gated channel subfamily V member 2, Potassium voltage-gated channel, subfamily H, member 7, isoform 2, Potassium/sodium hyperpolarization-activated cyclic nucleotide-gated channel 1, Potassium/sodium hyperpolarization-activated cyclic nucleotide-gated channel 2, Potassium/sodium hyperpolarization-activated cyclic nucleotide-gated channel 3, Potassium/sodium hyperpolarization-activated cyclic nucleotide-gated channel 4, Probable mitochondrial import receptor subunit TOM40 homolog, Purinergic receptor P2X5, isoform A, Putative 4 repeat voltage-gated ion channel, Putative chloride channel protein 7, Putative GluR6 kainate receptor, Putative ion channel protein CATSPER2 variant 1, Putative ion channel protein CATSPER2 variant 2, Putative ion channel protein CATSPER2 variant 3, Putative regulator of potassium channels protein variant 1, Putative tyrosine-protein phosphatase TPTE, Ryanodine receptor 1, Ryanodine receptor 2, Ryanodine receptor 3, SH3 KBP1 binding protein 1, Short transient receptor potential channel 1, Short transient receptor potential channel 4, Short transient receptor potential channel 5, Short transient receptor potential channel 6, Short transient receptor potential channel 7, Small conductance calcium-activated potassium channel protein 1, Small conductance calcium-activated potassium channel protein 2, isoform b, Small conductance calcium-activated potassium channel protein 3, isoform b, Small-conductance calcium-activated potassium channel SK2, Small-conductance calcium-activated potassium channel SK3, Sodium channel, Sodium channel beta-1 subunit precursor, Sodium channel protein type II alpha subunit, Sodium channel protein type III alpha subunit, Sodium channel protein type IV alpha subunit, Sodium channel protein type IX alpha subunit, Sodium channel protein type V alpha subunit, Sodium channel protein type VII alpha subunit, Sodium channel protein type VIII alpha subunit, Sodium channel protein type X alpha subunit, Sodium channel protein type XI alpha subunit, Sodium- and chloride-activated ATP-sensitive potassium channel, Sodium/potassium-transporting ATPase gamma chain, Sperm-associated cation channel 1, Sperm-associated cation channel 2, isoform 4, Syntaxin-1B1, Transient receptor potential cation channel subfamily A member 1, Transient receptor potential cation channel subfamily M member 2, Transient receptor potential cation channel subfamily M member 3, Transient receptor potential cation channel subfamily M member 6, Transient receptor potential cation channel subfamily M member 7, Transient receptor potential cation channel subfamily V member 1, Transient receptor potential cation channel subfamily V member 2, Transient receptor potential cation channel subfamily V member 3, Transient receptor potential cation channel subfamily V member 4, Transient receptor potential cation channel subfamily V member 5, Transient receptor potential cation channel subfamily V member 6, Transient receptor potential channel 4 epsilon splice variant, Transient receptor potential channel 4 zeta splice variant, Transient receptor potential channel 7 gamma splice variant, Tumor necrosis factor, alpha-induced protein 1, endothelial, Two-pore calcium channel protein 2, VDAC4 protein, Voltage gated potassium channel Kv3.2b, Voltage gated sodium channel beta1B subunit, Voltage-dependent anion channel, Voltage-dependent anion channel 2, Voltage-dependent anion-selective channel protein 1, Voltage-dependent anion-selective channel protein 2, Voltage-dependent anion-selective channel protein 3, Voltage-dependent calcium channel gamma-1 subunit, Voltage-dependent calcium channel gamma-2 subunit, Voltage-dependent calcium channel gamma-3 subunit, Voltage-dependent calcium channel gamma-4 subunit, Voltage-dependent calcium channel gamma-5 subunit, Voltage-dependent calcium channel gamma-6 subunit, Voltage-dependent calcium channel gamma-7 subunit, Voltage-dependent calcium channel gamma-8 subunit, Voltage-dependent L-type calcium channel alpha-1C subunit, Voltage-dependent L-type calcium channel alpha-1D subunit, Voltage-dependent L-type calcium channel alpha-IS subunit, Voltage-dependent L-type calcium channel beta-1 subunit, Voltage-dependent L-type calcium channel beta-2 subunit, Voltage-dependent L-type calcium channel beta-3 subunit, Voltage-dependent L-type calcium channel beta-4 subunit, Voltage-dependent N-type calcium channel alpha-1B subunit, Voltage-dependent P/Q-type calcium channel alpha-1A subunit, Voltage-dependent R-type calcium channel alpha-1E subunit, Voltage-dependent T-type calcium channel alpha-1G subunit, Voltage-dependent T-type calcium channel alpha-1H subunit, Voltage-dependent T-type calcium channel alpha-1I subunit, Voltage-gated L-type calcium channel alpha-1 subunit, Voltage-gated potassium channel beta-1 subunit, Voltage-gated potassium channel beta-2 subunit, Voltage-gated potassium channel beta-3 subunit, Voltage-gated potassium channel KCNA7. The Nav1.x family of human voltage-gated sodium channels is also a particularly promising target. This family includes, for example, channels Nav1.6 and Nav1.8.

In certain embodiments, the therapeutic protein may be a G-Protein Coupled Receptor (GPCR). Exemplary GPCRs include, but are not limited to, Class A Rhodopsin like receptors such as Muscatinic (Muse.) acetylcholine Vertebrate type 1, Muse, acetylcholine Vertebrate type 2, Muse, acetylcholine Vertebrate type 3, Muse, acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykinin, C5a anaphylatoxin, Fmet-leu-phe, APJ like, Interleukin-8 type A, Interleukin-8 type B, Interleukin-8 type others, C-C Chemokine type 1 through type 11 and other types, C—X—C Chemokine (types 2 through 6 and others), C-X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPR10), Neuropeptide Y (type 1 through 7), Neuropeptide Y, Neuropeptide Y other, Neurotensin, Opioid (type D, K, M, X), Somatostatin (type 1 through 5), Tachykinin (Substance P (NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF.QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory II fam 1 through 13), Prostaglandin (prostaglandin E2 subtype EP1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY1-4,6,1 1 GPR91, Purinoceptor P2RY5,8,9,10 GPR35,92,174, Purinoceptor P2RY12-14 GPR87 (UDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg-4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas protooncogene & Mas-related (MRGs), GPR45 like, Cysteinyl leukotriene, G-protein coupled bile acid receptor, Free fatty acid receptor (GP40, GP41, GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAI), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GABA-B subtype 1, GABA-B subtype 2, GABA-B like, Orphan GPRC5, Orphan GPCR6, Bride of sevenless proteins (BOSS), Taste receptors (T1R), Class D Fungal pheromone, Fungal pheromone A-Factor like (STE2.STE3), Fungal pheromone B like (BAR,BBR,RCB, PRA), Class E cAMP receptors, Ocular albinism proteins, Frizzled/Smoothened family, frizzled Group A (Fz 1&2&4&5&7-9), frizzled Group B (Fz 3 & 6), frizzled Group C (other), Vomeronasal receptors, Nematode chemoreceptors, Insect odorant receptors, and Class Z Archaeal/bacterial/fungal opsins.

In certain embodiments, the HSA binding $^{10}$Fn3 domain fusions described herein may comprise any of the following active polypeptides: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleukin, denileukin diftitox, interferon alfa-n3 (injection), interferon alfa-nl, DL-8234, interferon, Suntory (gamma-Ia), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP-401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphanate, octocog alfa, Factor VIII, palifermin, Indikinase, tenecteplase, alteplase, pamiteplase, reteplase, nateplase.monteplase, follitropin alfa, rFSH, hpFSH, micafungin, pegfilgrastim, lenograstim, nartograstim, sermorelin, glucagon, exenatide, pramlintide, imiglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enfuvirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasermin, Roferon-A, interferon-alpha 2, Alfaferone, interferon alfacon-1, interferon alpha, Avonex recombinant human luteinizing hormone, dornase alfa, trafermin, ziconotide, taltirelin, diboterminalfa, atosiban, becaplermin, eptifibatide, Zemaira, CTC-111, Shanvac-B, HPV vaccine (quadrivalent), NOV-002, octreotide, lanreotide, ancestim, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-2 IS, vapreotide, idursulfase, omapatrilat, recombinant serum albumin, certolizumab pegol, glucarpidase, human recombinant Cl esterase inhibitor (angioedema), lanoteplase, recombinant human growth hormone, enfuvirtide (needle-free injection, Biojector 2000), VGV-I, interferon (alpha), lucinactant, aviptadil (inhaled, pulmonary disease), icatibant, ecallantide, omiganan, Aurograb, pexiganan acetate, ADI-PEG-20, LDI-200, degarelix, cintredekin besudotox, FavId, MDX-1379, ISAtx-247, liraglutide, teriparatide (osteoporosis), tifacogin, AA-4500, T4N5 liposome lotion, catumaxomab, DWP-413, ART-123, Chrysalin, desmoteplase, amediplase, corifollitropin alpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-50-4798, interleukin-4, PRX-321, Pepscan, iboctadekin, rh lactoferrin, TRU-015, IL-21, ATN-161, cilengitide, Albuferon, Biphasix, IRX-2, omega interferon, PCK-3145, CAP-232, pasireotide, huN901-DM1, ovarian cancer immunotherapeutic vaccine, SB-249553, Oncovax-CL, OncoVax-P, BLP-25, CerVax-16, multi-epitope peptide melanoma vaccine (MART-I, gp100, tyrosinase), nemifitide, rAAT (inhaled), rAAT (dermatological), CGRP (inhaled, asthma), pegsunercept, thymosin beta-4, plitidepsin, GTP-200, ramoplanin, GRASPA, OBI-I, AC-100, salmon calcitonin (oral, eligen), calcitonin (oral, osteoporosis), examorelin, capromorelin, Cardeva, velafermin, 131I-TM-601, KK-220, TP-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotide acetate, CETi-I, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn1O (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alkaline phosphatase, EP-2104R, Melanotan-II, bremelanotide, ATL-104, recombinant human microplasmin, AX-200, SEMAX, ACV-I, Xen-2174, CJC-1008, dynorphin A, SI-6603, LAB GHRH, AER-002, BGC-728, malaria vaccine (virosomes, PeviPRO), ALTU-135, parvovirus B 19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85 A vaccine (tuberculosis), FAR-404, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, P1A, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT388IL-3, TST-10088, PRO-1762, Combotox, cholecystokinin-B/gastrin-receptor binding peptides, 1 1 11n-hEGF, AE-37, trastuzumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/I540/KLH vaccine (cancer), VX-001, AVE-9633, AC-9301, NY-ESO-I vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A2 (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1001 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV-4710, ALG-889, Org-41259, rhCCIO, F-991, thymopentin (pulmonary diseases), r(m)CRP, hepatoselective insulin, subalin, L 19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S. pneumoniae* pediatric vaccine, malaria vaccine, *Neisseria meningitidis* Group B vaccine, neonatal group B streptococcal vaccine, anthrax vaccine, HCV vaccine (gpEl+gpE2+MF-59), otitis media therapy, HCV vaccine (core antigen+ISCOMATRIX), hPTH(1-34) (transdermal, ViaDerm), 768974, SYN-101, PGN-0052, aviscumine, BIM-23190, tuberculosis vaccine, multi-epitope tyrosinase peptide, cancer vaccine, enkastim, APC-8024, G1-5005, ACC-001, TTS-CD3, vascular-targeted TNF (solid tumors), desmopressin (buccal controlled-release), onercept, TP-9201.

Additional Modifications

In certain embodiments, the HSA binding $^{10}$Fn3 domains and their fusions may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the HSA binding $^{10}$Fn3 domains and their fusions may contain non-amino acid elements, such as lipids, poly- or monosaccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See, e.g., Raju et al. Biochemistry 2001; 40:8868-76. Effects of such non-amino acid elements on the functionality of the HSA binding $^{10}$Fn3 domains and their fusions may be tested for their ability to bind a particular HSA binding $^{10}$Fn3 domains and/or the functional role conferred by a specific non-$^{10}$Fn3 moiety in the context of a fusion.

E. Vectors & Polynucleotides Embodiments

Also provided herein are nucleic acids encoding any of the polypeptides (e.g., polypeptides comprising HSA binding $^{10}$Fn3 domains and fusions thereof) described herein. Accordingly, in certain embodiments, provided herein are nucleic acids encoding any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118, the nucleic acid sequences of which can be readily determined by one skilled in the art from the parent 7016_A01 nucleic acid sequence (SEQ ID NO: 173).

As appreciated by those skilled in the art, because of third base degeneracy, almost every amino acid can be represented by more than one triplet codon in a coding nucleotide sequence. In addition, minor base pair changes may result in a conservative substitution in the amino acid sequence encoded but are not expected to substantially alter the biological activity of the gene product. Therefore, a nucleic acid sequence encoding a polypeptide described herein may be modified slightly in sequence and yet still encode its respective gene product. In some embodiments, nucleotide substitutions are introduced so as not to alter the resulting translated amino acid sequence. In certain embodiments, the nucleic acids encoding the HSA binding $^{10}$Fn3 domains and fusions thereof have nucleic acid sequences that encode the amino acid substitutions (relative to SEQ ID NO: 23) described herein.

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *PNAS* 2003; 100:438-42; Sinclair et al. *Protein Expr Purif* 2002; 26:96-105; Connell., *Curr Opin Biotechnol* 2001; 12:446-9; Makrides et al. Microbiol Rev 1996; 60:512-38; and Sharp et al. Yeast 1991; 7:657-78.

General techniques for nucleic acid manipulation are within the purview of one skilled in the art and are also described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding a protein is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated. Suitable regulatory elements are well-known in the art.

The polypeptides and fusions thereof described herein may be produced as a fusion protein with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders. For yeast secretion, the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO 90/13646. In mammalian cell expression, mammalian signal sequences as well as viral secretory leaders, for example, the herpes simplex gD signal, are available. The DNA for such precursor regions may be ligated in reading frame to DNA encoding the protein.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See PCT Publication No. WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). In some instance it will be desired to produce proteins in vertebrate cells, such as for glycosylation, and the propagation of vertebrate cells in culture (tissue culture) has become a routine procedure. Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. For many applications, the small size of the protein multimers described herein would make *E. coli* the preferred method for expression.

F. Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the HSA binding $^{10}$Fn3 domains and fusion molecules comprising such, as described herein, may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., *Meth*

Enz 58:44 (1979), Barnes et al., *Anal Biochem* 102:255 (1980), U.S. Pat. Nos. 4,767,704; 4,657,866; 4,927,762; 4,560,655; or 5,122,469; WO90/03430; WO87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

HSA binding $^{10}$Fn3 domains and fusion molecules comprising such, as described herein, can also be produced using cell-free translation systems. For such purposes the nucleic acids encoding the fibronectin based scaffold protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

The HSA binding $^{10}$Fn3 domains and fusion molecules comprising such, as described herein, can also be produced by chemical synthesis (e.g., by the methods described in Solid Phase Peptide Synthesis, 2nd ed., 1984, The Pierce Chemical Co., Rockford, Ill.). Modifications to the fibronectin based scaffold protein can also be produced by chemical synthesis.

The HSA binding $^{10}$Fn3 domains and fusion molecules comprising such, as described herein, can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, serum albumin binders and fusion molecules described herein may be exchanged into different buffers and/or concentrated by any of a variety of methods known to the art, including, but not limited to, filtration and dialysis.

The purified HSA binding $^{10}$Fn3 domains and fusion molecules comprising such, as described herein, are preferably at least 85% pure, more preferably at least 95% pure, and most preferably at least 98% pure. Regardless of the exact numerical value of the purity, the HSA binding $^{10}$Fn3 domains and fusion molecules comprising such, as described herein, are sufficiently pure for use as a pharmaceutical product.

The HSA binding $^{10}$Fn3 domains and fusion molecules comprising such, as described herein, may also be produced using the following protocols.

An Adnectin may be cloned into the PET9d vector upstream of a HIS$_6$tag and transformed into *E. coli* BL21 DE3 plysS cells are inoculated in 5 ml LB medium containing 50 µg/mL kanamycin in a 24-well format and grown at 37° C. overnight. Fresh 5 ml LB medium (50 µg/mL kanamycin) cultures are prepared for inducible expression by aspiration of 200 µl from the overnight culture and dispensing it into the appropriate well. The cultures are grown at 37° C. until A600 0.6-0.9. After induction with 1 mM isopropyl-β-thiogalactoside (IPTG), the culture is expressed for 6 hours at 30° C. and harvested by centrifugation for 10 minutes at 2750 g at 4° C.

Cell pellets (in 24-well format) are lysed by resuspension in 450 µl of Lysis buffer (50 mM NaH$_2$PO$_4$, 0.5 M NaCl, 1× Complete™ Protease Inhibitor Cocktail-EDTA free (Roche), 1 mM PMSF, 10 mM CHAPS, 40 mM imidazole, 1 mg/ml lysozyme, 30 µg/ml DNAse, 2 µg/ml aprotinin, pH 8.0) and shaken at room temperature for 1-3 hours. Lysates are cleared and re-racked into a 96-well format by transfer into a 96-well Whatman GF/D Unifilter fitted with a 96-well, 1.2 ml catch plate and filtered by positive pressure. The cleared lysates are transferred to a 96-well Nickel or Cobalt-Chelating Plate that had been equilibrated with equilibration buffer (50 mM NaH$_2$PO$_4$, 0.5 M NaCl, 40 mM imidazole, pH 8.0) and are incubated for 5 min. Unbound material is removed by positive pressure. The resin is washed twice with 0.3 ml/well with Wash buffer #1 (50 mM NaH$_2$PO$_4$, 0.5 M NaCl, 5 mM CHAPS, 40 mM imidazole, pH 8.0). Each wash is removed by positive pressure. Prior to elution, each well is washed with 50 µl Elution buffer (PBS+20 mM EDTA), incubated for 5 min, and this wash is discarded by positive pressure. Protein is eluted by applying an additional 100 µl of Elution buffer to each well. After a 30 minute incubation at room temperature, the plate(s) are centrifuged for 5 minutes at 200 g and eluted protein collected in 96-well catch plates containing 5 µl of 0.5 M MgCl$_2$ added to the bottom of elution catch plate prior to elution. Eluted protein is quantified using a total protein assay with wild-type $^{10}$Fn3 domain as the protein standard.

For expression of insoluble Adnectins, the nucleic acid encoding the Adnectin(s), followed by the HIS$_6$tag, are cloned into a pET9d (EMD Bioscience, San Diego, Calif.) vector and are expressed in *E. coli* HMS174 cells. Twenty ml of an inoculum culture (generated from a single plated colony) is used to inoculate 1 liter of LB medium containing 50m/ml carbenicillin and 34m/ml chloramphenicol. The culture is grown at 37° C. until A600 0.6-1.0. After induction with 1 mM isopropyl-β-thiogalactoside (IPTG) the culture is grown for 4 hours at 30° C. and is harvested by centrifugation for 30 minutes at >10,000 g at 4° C. Cell pellets are frozen at −80° C. The cell pellet is resuspended in 25 ml of lysis buffer (20 mM aH2PO$_4$, 0.5 M NaCl, 1× Complete Protease Inhibitor Cocktail-EDTA free (Roche), 1 mM PMSF, pH 7.4) using an ULTRA-TURRAX® homogenizer (IKA works) on ice. Cell lysis is achieved by high pressure homogenization (>18,000 psi) using a Model M-1 10S MICROFLUIDIZER® (Microfluidics). The insoluble fraction is separated by centrifugation for 30 minutes at 23,300 g at 4° C. The insoluble pellet recovered from centrifugation of the lysate is washed with 20 mM sodium phosphate/500 mM NaCl, pH7.4. The pellet is resolubilized in 6.0 M guanidine hydrochloride in 20 mM sodium phosphate/500 M NaCl pH 7.4 with sonication followed by incubation at 37° C. for 1-2 hours. The resolubilized pellet is filtered to 0.45 µm and loaded onto a Histrap column equilibrated with the 20 mM sodium phosphate/500 M NaCl/6.0 M guanidine pH 7.4 buffer. After loading, the column is washed for an additional 25 CV with the same buffer. Bound protein is eluted with 50 mM Imidazole in 20 mM sodium phosphate/ 500 mM NaCl/6.0 M guan-HCl pH7.4. The purified protein is refolded by dialysis against 50 mM sodium acetate/150 mM NaCl pH 4.5.

For expression of soluble Adnectins, the nucleic acid encoding the Adnectin(s), followed by the $HIS_6$tag, are cloned into a pET9d (EMD Bioscience, San Diego, Calif.) vector and are expressed in *E. coli* HMS174 cells. Twenty ml of an inoculum culture (generated from a single plated colony) is used to inoculate 1 liter of LB medium containing 50 µg/ml carbenicillin and 34 µg/ml chloramphenicol. The culture is grown at 37° C. until $A_{600}$ 0.6-1.0. After induction with 1 mM isopropyl-β-thiogalactoside (IPTG), the culture is grown for 4 hours at 30° C. and harvested by centrifugation for 30 minutes at >10,000 g at 4° C. Cell pellets are frozen at −80° C. The cell pellet is resuspended in 25 ml of lysis buffer (20 mM $NaH_2PO_4$, 0.5 M NaCl, 1x Complete Protease Inhibitor Cocktail-EDTA free (Roche), 1 mM PMSF, pH 7.4) using an ULTRA-TURRAX® homogenizer (IKA works) on ice. Cell lysis is achieved by high pressure homogenization (>18,000 psi) using a Model M-1 10S MICROFLUIDIZER® (Microfluidics). The soluble fraction is separated by centrifugation for 30 minutes at 23,300 g at 4° C. The supernatant is clarified via 0.45 µm filter. The clarified lysate is loaded onto a Histrap column (GE) pre-equilibrated with 20 mM sodium phosphate/500 M NaCl pH 7.4. The column is then washed with 25 column volumes of the same buffer, followed by 20 column volumes of 20 mM sodium phosphate/500 M NaCl/25 mM Imidazole, pH 7.4 and then 35 column volumes of 20 mM sodium phosphate/500 M NaCl/40 mM Imidazole, pH 7.4. Protein is eluted with 15 column volumes of 20 mM sodium phosphate/500 M NaCl/500 mM Imidazole, pH 7.4, fractions are pooled based on absorbance at $A_2$so and dialyzed against 1×PBS, 50 mM Tris, 150 mM NaCl; pH 8.5 or 50 mM NaOAc; 150 mM NaCl; pH4.5. Any precipitate is removed by filtering at 0.22 µm.

G. Imaging, Diagnostic, and Other Applications

The HSA binding $^{10}$Fn3 fusions provided herein may be used to treat a variety of diseases and disorders, based on the identity of the heterologous molecule fused to the HSA binding $^{10}$Fn3 domain. The applications for the HSA binding $^{10}$Fn3 fusions may be determined by the skilled artisan based on the knowledge in the art and the information provided herein. Uses for various HSA binding $^{10}$Fn3 fusion proteins are described in detail herein. HSA binding $^{10}$Fn3fusions may be administered to any mammalian subject or patient, including both human and non-human organisms.

The HSA binding $^{10}$Fn3 domains and fusion molecules described herein can be detectably labeled and used to contact cells expressing, e.g., a protein bound by the fusion molecule for imaging or diagnostic applications. Any method known in the art for conjugating a protein to the detectable moiety may be employed, including those methods described by Hunter et al., *Nature* 1962; 144:945; David et al., *Biochemistry* 1974; 13:1014; Pain et al., *J Immunol Meth* 1981; 40:219; and Nygren, *Histochem and Cytochem* 1982; 30:407.

In certain embodiments, the HSA binding $^{10}$Fn3 domains and fusion molecules comprising such, as described herein, are further attached to a label that is able to be detected (e.g., the label can be a radioisotope, fluorescent compound, enzyme or enzyme co-factor). The label may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. In certain embodiments, the label can be a fluorescent or chemiluminescent compound, such as fluorescein isothiocyanate, rhodamine, or luciferin; or an enzyme, such as alkaline phosphatase, beta-galactosidase or horseradish peroxidase. The HSA binding $^{10}$Fn3 domain or fusion molecule affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety.

The HSA binding $^{10}$Fn3 domains and fusion molecules comprising such, as described herein, also are useful as affinity purification agents. In this process, the proteins are immobilized on a suitable support, such a Sephadex resin or filter paper, using methods well known in the art. The proteins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

H. Biophysical and Biochemical Characterization

In Vitro Assays for Binding Affinity

Adnectins that bind to HSA can be identified using various in vitro assays. In certain embodiments, the assays are high-throughput assays that allow for screening multiple candidate Adnectins simultaneously.

Exemplary assays for determining the binding affinity of an Adnectin to its target includes, but is not limited to, solution phase methods such as the kinetic exclusion assay (KinExA) (Blake et al., *JBC* 1996; 271:27677-85; Drake et al., *Anal Biochem* 2004; 328:35-43), surface plasmon resonance (SPR) with the Biacore® system (Uppsala, Sweden) (Welford et al., *Opt. Quant. Elect* 1991; 23:1; Morton and Myszka, Methods in Enzymology 1998; 295:268) and homogeneous time resolved fluorescence (HTRF) assays (Newton et al., *J Biomol Screen* 2008; 13:674-82; Patel et al., *Assay Drug Dev Technol* 2008; 6:55-68).

In certain embodiments, biomolecular interactions can be monitored in real time with the Biacore® system, which uses SPR to detect changes in the resonance angle of light at the surface of a thin gold film on a glass support due to changes in the refractive index of the surface up to 300 nm away. Biacore analysis generates association rate constants, dissociation rate constants, equilibrium dissociation constants, and affinity constants. Binding affinity is obtained by assessing the association and dissociation rate constants using a Biacore surface plasmon resonance system (Biacore, Inc.). A biosensor chip is activated for covalent coupling of the target. The target is then diluted and injected over the chip to obtain a signal in response units of immobilized material. Since the signal in resonance units (RU) is proportional to the mass of immobilized material, this represents a range of immobilized target densities on the matrix. Association and dissociation data are fit simultaneously in a global analysis to solve the net rate expression for a 1:1 bimolecular interaction, yielding best fit values for $k_{on}$, $k_{off}$, and $R_{max}$ (maximal response at saturation). Equilibrium dissociation constants for binding, $K_D$, are calculated from SPR measurements as $k_{off}/k_{on}$.

The off-rates (kd), on-rates (ka), and dissociation equilibrium constants ($K_D$) of the HSA binding $^{10}$Fn3 domains described herein for binding to serum albumin from human, cynomolgus monkey, rat, mouse can be determined using SPR Biacore analysis. In certain embodiments, the respective serum albumins are mobilized on a Biacore CM5 chip to a surface density of ~1200RU using standard NHS/EDC coupling. A concentration range (0.25 nM-5 uM) of the HSA binding $^{10}$Fn3 domain to be tested is applied in HBS-P+ (0.01M HEPES pH 7.4, 0.15M NaCl, 0.05% v/v surfactant P-20) or Acetate (0.02 mM sodium acetate pH 5.5, 0.15M NaCl, 0.05% v/v surfactant P-20) running buffers to the immobilized albumins. Kinetic measurements are carried out using a 3 min association and 6-10 min dissociation phase. Kinetic traces of reference-subtracted sensograms are fit to a 1:1 binding model using Biaevaluation software.

It should be understood that the assays described herein above are exemplary, and that any method known in the art for determining the binding affinity between proteins (e.g., fluorescence based-transfer (FRET), enzyme-linked immunosorbent assay, and competitive binding assays (e.g., radioimmunoassays)) can be used to assess the binding affinities of the rum albumin binding $^{10}$Fn3 domains described herein.

In certain embodiments, the melting temperature ($T_m$) of HSA binding $^{10}$Fn3 domains described herein, of fusion proteins comprising such, is at least 50° C., such as at least 51° C., at least 52° C., at least 53° C., at least 54° C., at least 55° C., at least 56° C., at least 57° C., at least 58° C., at least 59° C., at least 60° C., at least 61° C., at least 62° C., at least 63° C., at least 64° C., at least 65° C., at least 66° C., at least 67° C., at least 68° C., at least 69° C., at least 70° C., at least 71° C., at least 72° C., at least 73° C., at least 74° C., or at least 75° C., when measured using differential scanning calorimetry (DSC) or thermal scanning fluorescence (TSF).

In certain embodiments, the melting temperature ($T_m$) of HSA binding $^{10}$Fn3 domains described herein, or fusion proteins comprising such, is 50-75° C., such as 51-75° C., 52-75° C., 53-75° C., 54-75° C., 55-75° C., 56-75° C., 57-75° C., 58-75° C., 59-75° C., 60-75° C., 61-75° C., 62-75° C., 63-75° C., 64-75° C., 65-75° C., 66-75° C., 67-75° C., 68-75° C., 69-75° C., 70-75° C., 50-74° C., 50-73° C., 50-72° C., 50-71° C., 50-70° C., 50-69° C., 50-68° C., 50-67° C., 50-66° C., 50-65° C., 50-64° C., 50-63° C., 50-62° C., 50-61° C., 50-60° C., 50-59° C., 50-58° C., 50-57° C., 50-56° C., 50-55° C., 51-74° C., 52-73° C., 53-71° C., 54-70° C., or 55-65° C., when measured using differential scanning calorimetry (DSC) or thermal scanning fluorescence (TSF).

I. Therapeutic In Vivo Uses

Provided herein are HSA binding $^{10}$Fn3 domains and fusion molecules comprising such that are useful in the treatment of disorders. In the case of fusion proteins comprising a HSA binding $^{10}$Fn3 domain, the diseases or disorders that may be treated will be dictated by the binding specificity of the moiety, e.g., a second $^{10}$Fn3 domain that is linked to the Adnectin. As described herein, fibronectin based scaffold proteins may be designed to bind to any target of interest. In one embodiment, the target is PCSK9. Fibronectin based scaffold proteins that bind to PSCK9 and the fusion proteins comprising such can be used to treat atherosclerosis, hypercholesterolemia and other cholesterol related diseases.

The application also provides methods for administering fibronectin based scaffold proteins to a subject. In certain embodiments, the subject is a human. In certain embodiments, the fibronectin based scaffold proteins are pharmaceutically acceptable to a mammal, in particular a human. A "pharmaceutically acceptable" composition refers to a composition that is administered to an animal without significant adverse medical consequences. Examples of pharmaceutically acceptable compositions include compositions comprising polypeptides comprising $^{10}$Fn3 domains that lack the integrin-binding domain (RGD) and compositions that are essentially endotoxin or pyrogen free or have very low endotoxin or pyrogen levels.

J. Formulations and Administration

Provided herein are methods for administering a moiety (e.g., a therapeutic moiety) fused to a HSA binding $^{10}$Fn3 domain, wherein the half-life of the moiety is extended when fused to the HSA binding $^{10}$Fn3 domain. Techniques and dosages for administration of the fusion constructs will vary depending on the type of therapeutic moiety fused to the HSA binding $^{10}$Fn3 domain and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

In certain embodiments, pharmaceutical formulations of HSA binding $^{10}$Fn3 domains and fusion molecules comprising such, as described herein, comprise, e.g., 1-20 mM succinic acid, 2-10% sorbitol, and 1-10% glycine at pH 4.0-7.0. In an exemplary embodiment, pharmaceutical formulations of HSA binding $^{10}$Fn3 domains and their fusion molecules comprise, e.g., 10 mM succinic acid, 8% sorbitol, and 5% glycine at pH 6.0.

In certain embodiments, the HSA binding $^{10}$Fn3 domains and fusions comprising such, as described herein, are pharmaceutically acceptable to a mammal, in particular a human. A "pharmaceutically acceptable" polypeptide refers to a polypeptide that is administered to an animal without significant adverse medical consequences. Examples of pharmaceutically acceptable HSA binding $^{10}$Fn3 domain and fusions comprising such, as described herein, include $^{10}$Fn3 domains that lack the integrin-binding domain (RGD) and compositions of HSA binding $^{10}$Fn3 domains or HSA binding $^{10}$Fn3 domain fusions that are essentially endotoxin free or have very low endotoxin levels.

Compositions (e.g., therapeutic compositions) may be administered with a carrier (e.g., a pharmaceutically acceptable diluent, carrier, or excipient), in unit dosage form. Administration may be parenteral (e.g., intravenous, subcutaneous), oral, or topical, as non-limiting examples. The composition can be in the form of a pill, tablet, capsule, liquid, or sustained release tablet for oral administration; a liquid for intravenous, subcutaneous or parenteral administration; or a gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the HSA binding $^{10}$Fn3 domain or HSA binding $^{10}$Fn3 domain fusion is administered at about 0.01 mg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or less frequently (e.g., once every other day, once or twice weekly, once every two weeks, or monthly). In addition, as is known in the art, adjustments for age as well as the body weight, general health, sex, diet, time of administration, drug interaction, and the severity of the disease may be necessary, and will be ascertainable with routine experimentation by those skilled in the art.

K. Exemplary Embodiments

Embodiment 1

A polypeptide comprising a fibronectin type III tenth ($^{10}$Fn3) domain, wherein the $^{10}$Fn3 domain binds to human serum albumin (HSA) with a $K_D$ or 1 µM or less and comprises AB, BC, CD, DE, EF, and FG loops, wherein the CD loop has 1, 2, or 3 amino acid substitutions, and the FG loop optionally has 1, 2, or 3 amino acid substitutions, relative to the CD and FG loops of a $^{10}$Fn3 domain comprising the amino acid sequence set forth in SEQ ID NO: 23, and wherein the serum half-life of a moiety (e.g., polypeptide) that is linked to the $^{10}$Fn3 domain is extended relative to that of the moiety that is not linked to the $^{10}$Fn3 domain.

Embodiment 2

The polypeptide of embodiment 1, wherein the polypeptide binds to HSA with an off-rate (kd) that is greater than the kd of the $^{10}$Fn3 domain comprising the amino acid sequence set forth in SEQ ID NO: 23.

Embodiment 3

The polypeptide of embodiment 1 or 2, wherein the polypeptide binds to HSA with an on-rate (ka) that is within an order of magnitude (i.e., within 10-fold) of the ka of the $^{10}$Fn3 domain comprising the amino acid sequence set forth in SEQ ID NO: 23.

Embodiment 4

The polypeptide of any one of embodiments 1-3, wherein the CD loop has 2 amino acid substitutions relative to the corresponding CD loop of the $^{10}$Fn3 domain comprising the amino acid sequence set forth in SEQ ID NO: 23.

Embodiment 5

The polypeptide of any one of embodiments 1-3, wherein the CD loop has 1 amino acid substitution relative to the CD loop of the $^{10}$Fn3 domain comprising the amino acid sequence set forth in SEQ ID NO: 23.

Embodiment 6

The polypeptide of any one of embodiments 1-3, wherein the FG loop has 1 amino acid substitution relative to the FG loop of the $^{10}$Fn3 domain comprising the amino acid sequence set forth in SEQ ID NO: 23.

Embodiment 7

The polypeptide of any one of embodiments 1-3, wherein the CD loop has 1 amino acid substitution and the FG loop has 1 substitution relative to the CD loop and FG loop of the $^{10}$Fn3 domain comprising the amino acid sequence set forth in SEQ ID NO: 23.

Embodiment 8

The polypeptide of embodiment 4, wherein the 2 amino acid substitutions are selected from the group consisting of:
  (i) the arginine (R) at position 2 of the CD loop (SEQ ID NO: 28) is substituted with an amino acid selected from D, E, A, Q, or N;
  (ii) the glutamine (Q) at position 5 of the CD loop (SEQ ID NO: 28) is substituted with D;
  (iii) the tyrosine (Y) at position 7 of the CD loop (SEQ ID NO: 28) is substituted with an amino acid selected from S or A;
  (iv) the leucine (L) at position 10 of the CD loop (SEQ ID NO: 28) is substituted with an amino acid selected from S, T, or A;

(v) the leucine (L) at position 13 of the CD loop (SEQ ID NO: 28) is substituted with an amino acid selected from D, S, or A;
(vi) the tyrosine (Y) at position 14 of the CD loop (SEQ ID NO: 28) is substituted with an amino acid selected from A or T;
(vii) the isoleucine (I) at position 15 of the CD loop (SEQ ID NO: 28) is substituted with an amino acid selected from D, S, or A; and
(viii) The tyrosine (Y) at position 16 of the CD loop (SEQ ID NO: 28) is substituted with an amino acid selected from Q, E, S, or A.

Embodiment 9

The polypeptide of embodiment 5, wherein the 1 amino acid substitution is selected from the group consisting of:
(i) the arginine (R) at position 2 of the CD loop (SEQ ID NO: 28) is substituted with an amino acid selected from D, E, A, Q, or N;
(ii) the glutamine (Q) at position 5 of the CD loop (SEQ ID NO: 28) is substituted with D;
(iii) the tyrosine (Y) at position 7 of the CD loop (SEQ ID NO: 28) is substituted with an amino acid selected from S or A;
(iv) the leucine (L) at position 10 of the CD loop (SEQ ID NO: 28) is substituted with an amino acid selected from S, T, or A;
(v) the leucine (L) at position 13 of the CD loop (SEQ ID NO: 28) is substituted with an amino acid selected from D, S, or A;
(vi) the tyrosine (Y) at position 14 of the CD loop (SEQ ID NO: 28) is substituted with an amino acid selected from A or T;
(vii) the isoleucine (I) at position 15 of the CD loop (SEQ ID NO: 28) is substituted with an amino acid selected from D, S, or A; and
(viii) The tyrosine (Y) at position 16 of the CD loop (SEQ ID NO: 28) is substituted with an amino acid selected from Q, E, S, or A.

Embodiment 10

The polypeptide of embodiment 9, wherein the tyrosine (Y) at position 16 of the CD loop (SEQ ID NO: 28) is substituted with serine (S).

Embodiment 11

The polypeptide of embodiment 9, wherein the leucine (L) at position 10 of the CD loop (SEQ ID NO: 28) is substituted with threonine (T).

Embodiment 12

The polypeptide of embodiment 9, wherein the tyrosine (Y) at position 16 of the CD loop (SEQ ID NO: 28) is substituted with glutamine (Q).

Embodiment 13

The polypeptide of embodiment 6, wherein the lysine (K) at position 12 of the FG loop (SEQ ID NO: 29) is substituted with an amino acid selected from A, T, or S.

Embodiment 14

The polypeptide of embodiment 7, wherein
a) the 1 amino acid substitution in the CD loop selected from the group consisting of
(i) the arginine (R) at position 2 of the CD loop (SEQ ID NO: 28) is substituted with an amino acid selected from D, E, A, Q, or N;
(ii) the glutamine (Q) at position 5 of the CD loop (SEQ ID NO: 28) is substituted with D;
(iii) the tyrosine (Y) at position 7 of the CD loop (SEQ ID NO: 28) is substituted with an amino acid selected from S or A;
(iv) the leucine (L) at position 10 of the CD loop (SEQ ID NO: 28) is substituted with an amino acid selected from S, T, or A;
(v) the leucine (L) at position 13 of the CD loop (SEQ ID NO: 28) is substituted with an amino acid selected from D, S, or A;
(vi) the tyrosine (Y) at position 14 of the CD loop (SEQ ID NO: 28) is substituted with an amino acid selected from A or T;
(vii) the isoleucine (I) at position 15 of the CD loop (SEQ ID NO: 28) is substituted with an amino acid selected from D, S, or A; and
(viii) The tyrosine (Y) at position 16 of the CD loop (SEQ ID NO: 28) is substituted with an amino acid selected from Q, E, S, or A; and
b) the lysine at position 12 of the FG loop (SEQ ID NO: 29) is substituted with an amino acid selected from A, T, or S.

Embodiment 15

The polypeptide of any one of the preceding embodiments, wherein the polypeptide comprises an amino acid sequence at least 80%, 85%, 90%, 95%, 96%, 97%, 98%, 99%, or 100% identical to the non-CD loop regions of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118.

Embodiment 16

The polypeptide of any one of the preceding embodiments, wherein the polypeptide comprises an amino acid sequence that is at least 80%, 85%, 90%, 95%, 96%, 97%, 98%, 99%, or 100% identical to any one of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118.

Embodiment 17

The polypeptide of any one of the preceding embodiments, wherein the $^{10}$Fn3 domain binds to domain I-II of HSA.

Embodiment 18

The polypeptide of any one of the preceding embodiments, wherein the off-rate of the polypeptide to the off-rate of the $^{10}$Fn3 domain comprising the amino acid sequence set forth in SEQ ID NO: 23 has a ratio of at least about 3.

Embodiment 19

The polypeptide of embodiment 17, wherein the ratio is at least about 25.

Embodiment 20

The polypeptide of embodiment 17, wherein the ratio is at least about 50.

Embodiment 21

The polypeptide of any one of the preceding embodiments, wherein the polypeptide comprises a heterologous protein.

Embodiment 22

The polypeptide of embodiment 20, wherein the heterologous protein is a therapeutic moiety.

Embodiment 23

The polypeptide of embodiment 21 or 22, wherein the heterologous protein is a polypeptide comprising a $^{10}$Fn3 domain.

Embodiment 24

A composition comprising the polypeptide or fusion polypeptide of any one of the preceding embodiments, and a carrier.

Embodiment 25

An isolated nucleic acid molecule encoding the polypeptide of any one of embodiments 1-23.

Embodiment 26

An expression vector comprising the nucleotide sequence encoding the polypeptide of any one of embodiments 1-23.

Embodiment 27

A cell comprising the nucleic acid molecule of embodiment 25 or expression vector of embodiment 26.

Embodiment 28

A method of producing the polypeptide of any one of embodiments 1-23 comprising culturing the cell of embodiment 27 under conditions suitable for expressing the polypeptide, and purifying the polypeptide.

Embodiment 29

A method of enhancing the half-life of a moiety, comprising linking to the moiety a human serum albumin binding polypeptide of any one of embodiments 1-23.

The contents of all figures and all references, Genbank sequences, patents and published patent applications cited throughout this application are expressly incorporated herein by reference. In particular, the disclosure of PCT Application No. PCT/US2015/021535 and WO2011/140086 are expressly incorporated herein by reference.

The above disclosure generally describes the present disclosure, which is further exemplified by the following examples. These specific examples are described solely for purposes of illustration, and are not intended to limit the scope of this disclosure. Although specific targets, terms, and values have been employed herein, such targets, terms, and values will likewise be understood as exemplary and non-limiting to the scope of this disclosure.

EXAMPLES

Example 1: Generation of Human Serum Albumin Binding ADX_2629_E06-Based Variant $^{10}$Fn3 Domains The Adnectin ADX_7016_A01 (also referred to as a PKE2 Adnectin herein) was isolated as a polypeptide that binds to domain I-II of HSA with the following core sequence:

```
the CD and FG loops are
underlined;                            (SEQ ID NO: 23)
EVVAATPTSLLISWDAPAVTVRYYRITYGREVQKYSDLGPLYIYQEFTVP

GSKSTATISGLKPGVDYTITVYAVTGSGESPASSKPISINYRT
```

ADX_7016_A01 has low immunogenicity and binds to HSA with a $K_D$ of about 3-6 nM. A polypeptide comprising a PCSK9-binding Adnectin fused to ADX_7016_A01 has a half-life of about 82 hours in mice. In order to increase the versatility of half-live ranges of fusion partners (e.g., in certain situations, a shorter half life than that conferred by ADX_7016_A01 may be preferred), the CD and/or FG loop of ADX_7016_A01 was subjected to mutagenesis (single or double substitutions) and Adnectins that exhibited a lower off-rate (kd) than ADX_7016_A01 were identified. These Adnectins are herein referred to as "PKE3" Adnectins.

Single amino acid substitutions in the CD or FG loop (relative to the CD or FG loop of ADX_7016_A01) that retain the low immunogenicity of the polypeptide were generated in order to identify a series of molecules with a range of different affinities for HSA ($K_D$ expected in the low nM to 1 µM range).

A homology model was produced for ADX_7016_A01 (based on its parent Adnectin) using standard homology modeling tools within Molecular Operating Environment (MOE), Chemical Computing Group Inc., Montreal, QC, Canada). The modeled binding site of ADX_7016_A01 in complex with HSA showed that there were two regions of the Adnectin in contact. Select residues from the FG loop form weak interactions with HSA, while the major contact residues are found in the CD loop (located on the "south pole"). Using the CalculateInteractionEnergy protocol from DISCOVERY STUDIO (Dassault Systémes BIOVIA, Discovery Studio Modeling Environment, San Diego), the interaction energies were calculated for Adnectin bound to HSA. All of the residues that are predicted to contribute the most to binding HSA are located in the CD loop. A table showing the explicit residues interactions was generated using the Protein Interaction Analysis protocol from BIOLUMINATE. By combining the interaction energies with the type and quantity of interaction, the residues in the CD and FG loops of the Adnectin were ranked for mutational studies.

Based upon the results of the binding site analysis, positions were selected for mutagenesis. These amino acids were selected to be small and polar and would be predicted to decrease surface contact with amino acids in HSA when used in the mutational study. Computational mutation studies were performed in which each of the positions was substituted and interaction energies calculated for Adnectin bound to HSA. Specific positions were identified where the calculated interactions would predict a decrease in Adnectin-HSA affinity. Mutants were also designed so as not to increase the predicted risk for T-cell epitopes. Mutants were selected on the basis that they did not increase the predicted risk of T-cell epitopes and had the lowest possible immunogenicity scores (iDAB scores).

The iDAB immunogenicity score is based upon IEDB (as described in Vita et al., Nucleic Acids Res 2015; 43(Database issue):D405-12), and is proportional to the fraction of 15-mers in the protein sequence that are predicted to show high binding affinity to at least 4 of the 8 commonly found alleles in the world population. The score is obtained through a linear regression fit of the fraction of strong-binding 15-mers to experimental binding affinities. For the positions identified in the binding site analysis, single mutants that were predicted to have low immunogenicity scores were identified and combined into double mutants.

The resulting single and double mutants are summarized in Tables 1-3 (the substitutions listed are in relation to positions in the core 7016_A01 sequence set forth in SEQ ID NO: 23).

TABLE 1

| Adnectin ID | Position in core 7016_A01 sequence (SEQ ID NO: 23) | Residue in 7016_A01 | Residue in variant | Loop with substitution | iDAB immunogenicity score |
|---|---|---|---|---|---|
| Wt $^{10}$Fn3 | | | | | −37.8 |
| SGE | | | | | −37.8 |
| ADX_7016_A01 | | | | | −0.3 |
| 1 | 44 | Y | Q | CD | −23.2 |
| 2 | 44 | Y | E | CD | −30.8 |
| 3 | 44 | Y | S | CD | −23.2 |
| 4 | 44 | Y | A | CD | −27.0 |
| 5 | 41 | L | D | CD | −11.7 |
| 6 | 41 | L | S | CD | −11.7 |
| 7 | 41 | L | A | CD | −11.7 |
| 8 | 38 | L | S | CD | −0.3 |
| 9 | 38 | L | T | CD | −0.3 |
| 10 | 38 | L | A | CD | −0.3 |
| 11 | 33 | Q | D | CD | −0.3 |
| 12 | 30 | R | D | CD | −23.2 |
| 13 | 30 | R | E | CD | −11.7 |
| 14 | 30 | R | A | CD | −0.3 |
| 15 | 30 | R | Q | CD | −11.7 |
| 16 | 30 | R | N | CD | −4.1 |
| 17 | 42 | Y | A | CD | −0.3 |
| 18 | 42 | Y | T | CD | −0.3 |
| 19 | 43 | I | D | CD | −15.5 |
| 20 | 43 | I | S | CD | −7.9 |
| 21 | 43 | I | A | CD | −7.9 |
| 22 | 35 | Y | S | CD | −0.3 |
| 23 | 35 | Y | A | CD | −0.3 |
| 24 | 85 | K | A | FG | −0.3 |
| 25 | 85 | K | T | FG | −0.3 |
| 26 | 85 | K | S | FG | −0.3 |

Double amino acid substitutions in the CD loop (i.e., CD/CD mutations), relative to the CD loop of ADX_7016_A01, were made as shown in Table 2.

TABLE 2

| Substitution Position | Y44E | Y44A | Y44S | Y44Q | L41A | L41S | L41D |
|---|---|---|---|---|---|---|---|
| L41A | L41A/Y44E | L41A/Y44A | L41A/Y44S | L41A/Y44Q | | | |
| L41S | L41S/Y44E | L41S/Y44A | L41S/Y44S | L41S/Y44Q | | | |
| L41D | L41D/Y44E | L41D/Y44A | L41D/Y44S | L41D/Y44Q | | | |
| I43A | I43A/Y44E | I43A/Y44A | I43A/Y44S | I43A/Y44Q | I43A/L41A | I43A/L41S | I43A/L41D |
| I43S | I43S/Y44E | I43S/Y44A | I43S/Y44S | I43S/Y44Q | I43S/L41A | I43S/L41S | I43S/L41D |
| L38A | L38A/Y44E | L38A/Y44A | L38A/Y44S | L38A/Y44Q | L38A/L41A | L38A/L41S | L38A/L41D |
| L38S | L38S/Y44E | L38S/Y44A | L38S/Y44S | L38S/Y44Q | L38S/L41A | L38S/L41S | L38S/L41D |
| L38T | L38T/Y44E | L38T/Y44A | L38T/Y44S | L38T/Y44Q | L38T/L41A | L38T/L41S | L38T/L41D |
| Q33D | Q33D/Y44E | Q33D/Y44A | Q33D/Y44S | Q33D/Y44Q | | | |
| R30E | R30E/Y44E | R30E/Y44A | R30E/Y44S | R30E/Y44Q | R30E/L41A | R30E/L41S | R30E/L41D |
| R30D | R30D/Y44E | R30D/Y44A | R30D/Y44S | R30D/Y44Q | R30D/L41A | R30D/L41S | R30D/L41D |
| R30A | | | | | | | |
| R30Q | | | | | R30Q/L41A | R30Q/L41S | R300/L41D |
| R30N | | | | | R30N/L41A | R30N/L41S | R30N/L41D |
| Y35A | Y35A/Y44E | Y35A/Y44A | Y35A/Y44S | Y35A/Y44Q | Y35A/L41A | Y35A/L41S | Y35A/L41D |
| Y35S | Y35S/Y44E | Y35S/Y44A | Y35S/Y44S | Y35S/Y44Q | Y35S/L41A | Y35S/L41S | Y35S/L41D |

Double amino acid substitutions in the CD and FG loops (CD/FG mutations), relative to the CD and FG loops of ADX_7016_A01, were made as shown in Table 3.

TABLE 3

| Substitution Position | K85A | K85T | K85S |
|---|---|---|---|
| Y44Q | Y44Q/K85A | Y44Q/K85T | Y44Q/K85S |
| Y44E | Y44E/K85A | Y44E/K85T | Y44E/K85S |
| Y44S | Y44S/K85A | Y44S/K85T | Y44S/K85S |
| Y44A | Y44A/K85A | Y44A/K85T | Y44A/K85S |
| L41D | L41D/K85A | L41D/K85T | L41D/K85S |
| L41S | L41S/K85A | L41S/K85T | L41S/K85S |
| L41A | L41A/K85A | L41A/K85T | L41A/K85S |
| L38S | L38S/K85A | L38S/K85T | L38S/K85S |
| L38T | L38T/K85A | L38T/K85T | L38T/K85S |
| L38A | L38A/K85A | L38A/K85T | L38A/K85S |
| Q33D | Q33D/K85A | Q33D/K85T | Q33D/K85S |
| R30D | R30D/K85A | R30D/K85T | R30D/K85S |
| R30E | R30E/K85A | R30E/K85T | R30E/K85S |
| R30A | R30A/K85A | R30A/K85T | R30A/K85S |
| R30Q | R30Q/K85A | R30Q/K85T | R30Q/K85S |
| R30N | R30N/K85A | R30N/K85T | R30N/K85S |
| Y42A | Y42A/K85A | Y42A/K85T | Y42A/K85S |
| Y42T | Y42T/K85A | Y42T/K85T | Y42T/K85S |
| I43D | I43D/K85A | I43D/K85T | I43D/K85S |
| I43A | I43A/K85A | I43A/K85T | I43A/K85S |
| Y35S | Y35S/K85A | Y35S/K85T | Y35S/K85S |
| Y35A | Y35A/K85A | Y35A/K85T | Y35A/K85S |

The mutants exhibited favorable biophysical properties, with only two mutants having an SEC of 2. The remaining mutants had an SEC of 1. All mutants were also highly expressed, at ≥1 mg/mL.

Example 2: Screening for Fast Off-Rate Human Serum Albumin Binding Adnectins

The mutant HSA binding Adnectins were screened for binding affinity to HSA in order to identify Adnectins that had a higher off-rate than the wild type parent Adnectin (i.e., ADX_7016_A01).

Screening of the mutant Adnectins generated in Example 1 identified four classes of Adnectins: those that bound with similar affinity as the parent Adnectin, those that had high binding affinity (reaches 100% binding), those with medium binding affinity (<100% binding relative to parent Adnectin), and those with low binding affinity (<50% binding relative to parent Adnectin).

Measurements were conducted by SPR and ELISA. SPR was conducted as follows. Full length HSA or mouse albumin was immobilized on a Biacore T series CM5 chip at 15 ug/mL in 10 mM acetate buffer (pH 5.0) buffer using standard NHS/EDC coupling, to a surface density of approximately 1000-1100 RU. For off-rate measurements at 25° C., PKE Adnectins were applied as analytes at 500 nM in HBS-P+(0.01 M HEPES pH 7.4, 0.15 M NaCl, 0.005% v/v Surfactant P20) running buffer at a flow rate of 20ul/min for 120s over the immobilized albumins, followed by 800s for dissociation. For kinetic affinity measurements carried out at 37° C., a concentration series of the PKE Adnectins (0.05-333 nM) was applied in HBS-P+running buffer at a flow rate of 40ul/min for 180s followed by dissociation for 240s or 600s. Regeneration of the chip surface between cycles was accomplished with two 30 second pulses of 10 mM Glycine, pH 2.0. Kinetic traces of reference-subtracted sensorgrams were fit to a 1:1 binding model for affinity using the Biaevaluation software. Only the dissociation phase was fit for determination of off-rates.

Direct binding ELISA assays were conducted as follows. Full length human and murine serum albumin at 10ug/ml in PBS were coated on Nunc Maxisorp plates overnight at 4° C. Plates were blocked in casein/PBS buffer. PKE Adnectins were allowed to bind over a 4-point concentration range of 0.032-4 uM for HSA and 0.008-1 uM for MSA. Bound Adnectin was detected by anti-His antibody conjugated with HRP (horseradish peroxidase) diluted 1:1500 in casein/PBS. Plates were developed with TMB substrate and absorbance read at 450 nm. Adnectins were binned as high, medium and low affinity binders based on the observed Ymax of the concentration response curves.

The results for a subset of the variant Adnectins, including SPR analysis and ELISA data for both binding to HSA and mouse serum albumin (MSA) are provided in Table 4.

TABLE 4

| DB ELISA Bins | HSA DB ELISA (OD450) | | HSA | | MSA DB ELISA (OD450) | | MSA | |
|---|---|---|---|---|---|---|---|---|
| | Ymin obs | Ymax obs | HSA kd (s-1) | kd/Parent kd | Ymin obs | Ymax obs | MSA kd (s-1) | kd/Parent kd |
| BEST (Close to Parent) | | | | | | | | |
| ADX_6727_C01 (K85A) | 88 | 98 | 2.97E−04 | 1.1 | 90 | 93 | 5.09E−04 | 1.2 |
| ADX_6727_D01 (K85T) | 88 | 97 | 2.59E−04 | 1.0 | 88 | 91 | 4.33E−04 | 1.0 |
| ADX_6727_B01 (K85S) | 94 | 97 | 3.21E−04 | 1.2 | 88 | 91 | 5.01E−04 | 1.2 |
| ADX_6727_B04 (Y35S/K85S) | 62 | 99 | 1.10E−03 | 4.1 | 74 | 95 | 1.42E−03 | 3.3 |
| ADX_6727_G10 (Y35S/K85A) | 54 | 96 | 8.92E−04 | 3.3 | 54 | 100 | 1.38E−03 | 3.2 |
| HIGH (Reaches 100% binding) | | | | | | | | |
| ADX_6727_C07 (R30A/K85S) | 44 | 100 | 2.18E−03 | 8 | 6 | 94 | 3.34E−03 | 7.8 |
| ADX_6727_C03 (Y35S) | 31 | 99 | 1.07E−03 | 4 | 23 | 95 | 1.21E−03 | 2.8 |
| ADX_6727_D02 (R30N) | 20 | 99 | 1.35E−03 | 5 | 17 | 93 | 1.18E−03 | 2.8 |
| ADX_6727_F06 (L41A/K85T) | 19 | 90 | 2.98E−03 | 11 | 4 | 91 | 5.50E−03 | 12.8 |
| ADX_6734_A02 (I43A/Y44E) | 4 | 100 | NB | NB | 3 | 100 | NB | NB |
| MEDIUM (<100% binding) | | | | | | | | |
| ADX_6727_G01 (L41A) | 12 | 79 | 3.70E−03 | 14 | 3 | 87 | 6.39E−03 | 14.9 |
| ADX_6727_F03 (I43Y) | 9 | 89 | 4.68E−03 | 17 | 2 | 67 | 3.80E−03 | 8.9 |
| ADX_6727_D06 (Y44A/K85S) | 8 | 67 | 5.46E−03 | 20 | 1 | 85 | 6.22E−03 | 14.5 |
| ADX_6727_F04 (Y44A/K85A) | 6 | 56 | 6.24E−03 | 23 | 2 | 77 | 6.94E−03 | 16.2 |
| ADX_6727_B05 (I43S/K85T) | 4 | 60 | 7.49E−03 | 28 | 2 | 63 | 7.81E−03 | 18.2 |
| LOW (<50% binding) | | | | | | | | |
| ADX_6727_B11 (Q33D/K85S) | 1 | 12 | 1.51E−02 | 56 | 1 | 11 | NB | NB |
| ADX_6727_D10 (Q33D/K85T) | 2 | 19 | 1.34E−02 | 50 | 1 | 42 | 6.08E−02 | 142.1 |
| ADX_6727_B09 (L38T/K85T) | 2 | 16 | 9.21E−03 | 34 | 1 | 27 | 2.62E−02 | 61.2 |
| ADX_6727_H02 (I43S) | 2 | 37 | 1.39E−02 | 52 | 1 | 39 | 9.77E−03 | 22.8 |
| ADX_6727_G05 (I43S/K85A) | 2 | 38 | 1.43E−02 | 53 | 1 | 32 | 1.16E−02 | 27.0 |

*Note:
Off-rates for HTTP proteins measured at 25° C. The numbering of the amino acid substitutions listed in parentheses under the name of the Adnectins is based on the core amino acid sequence of ADX_7016_A01 (SEQ ID NO: 23).

Figure 2:
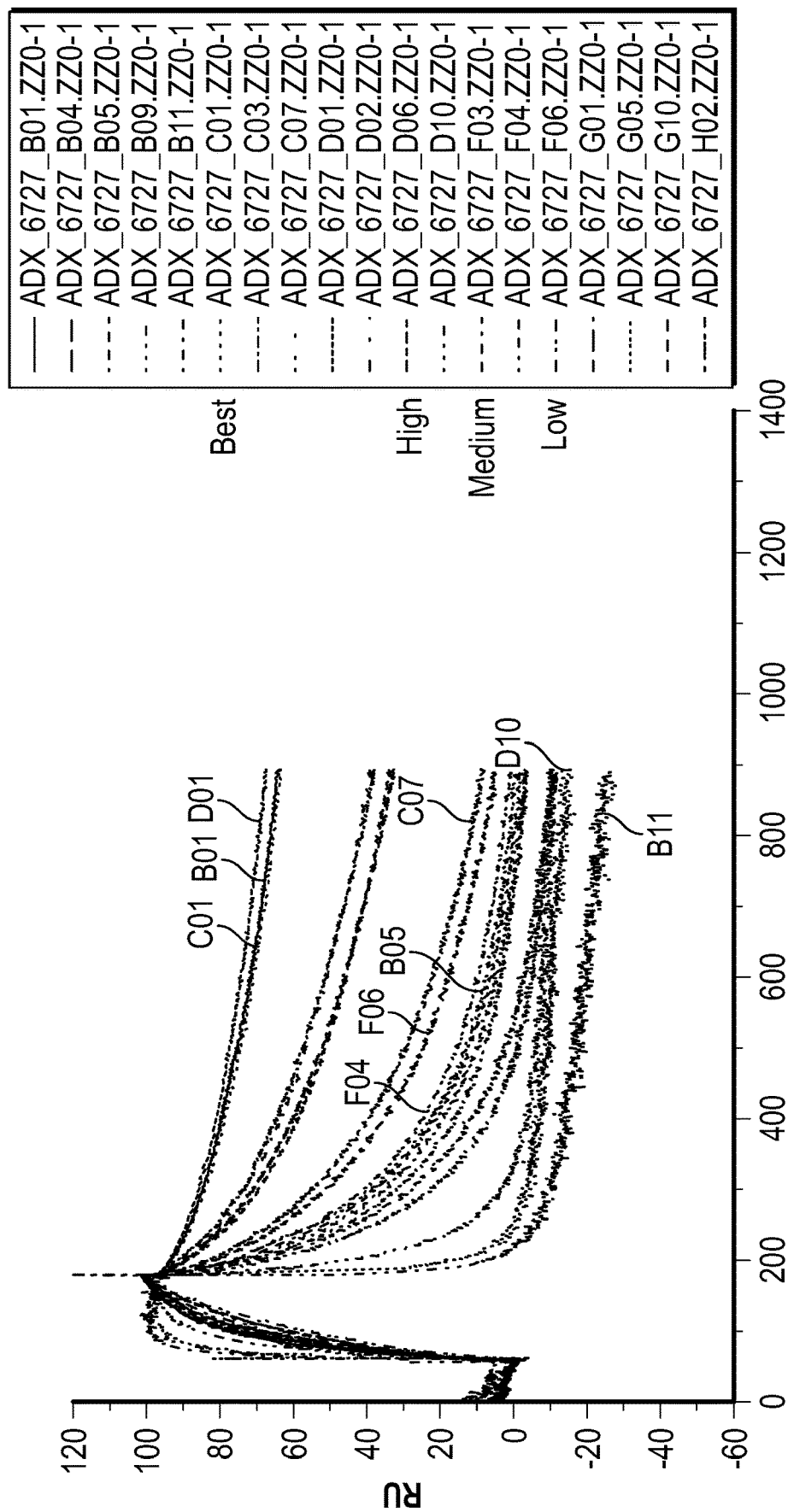
Figure 3A:
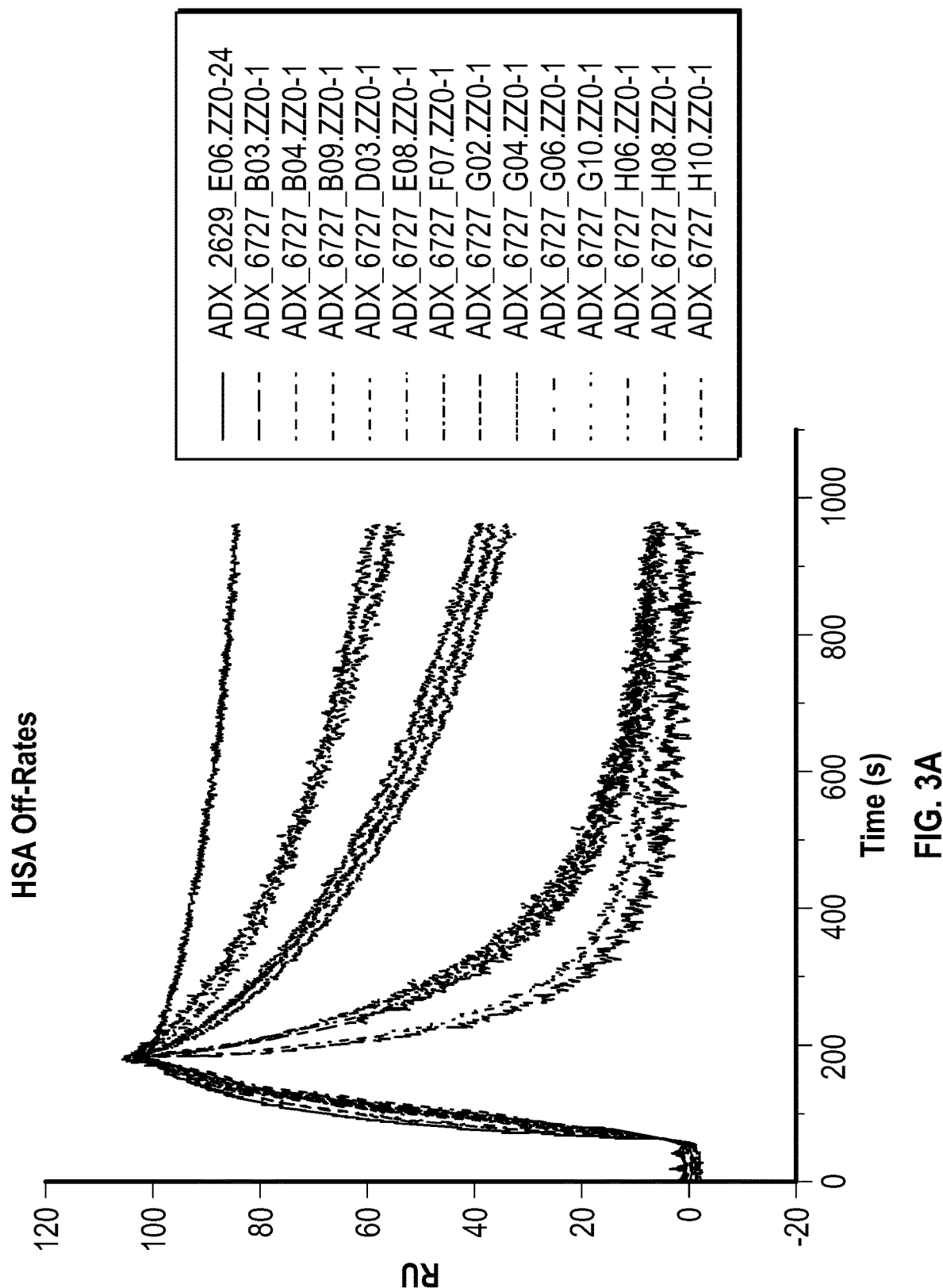
FIGS. 3A-3D show SPR sensograms of additional Adnectins binding to HSA and mouse serum albumin (MSA), normalized at start of dissociation phase to illustrate differences in off-rates of binding.
Figure 3B:
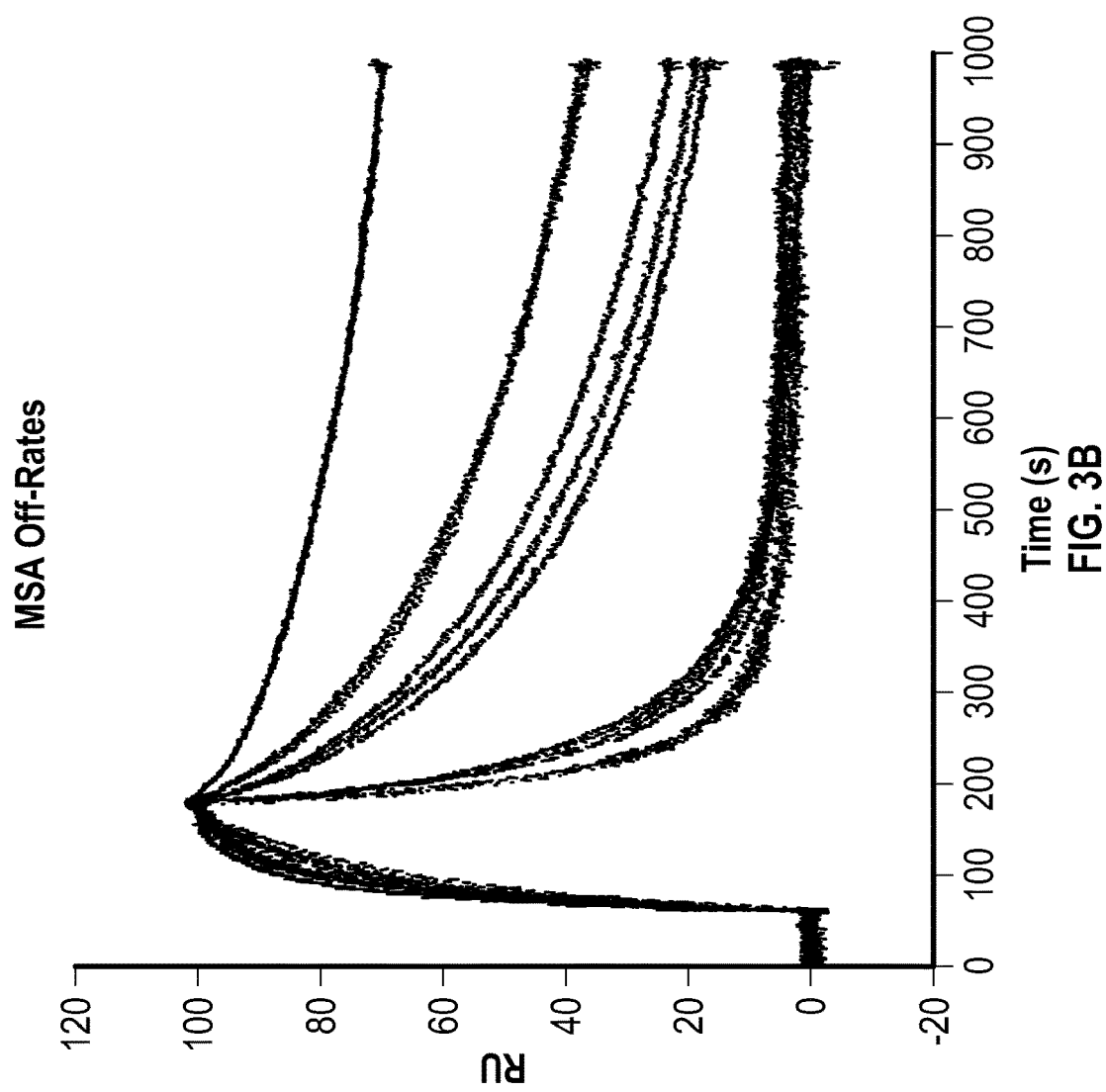
Figure 3C:
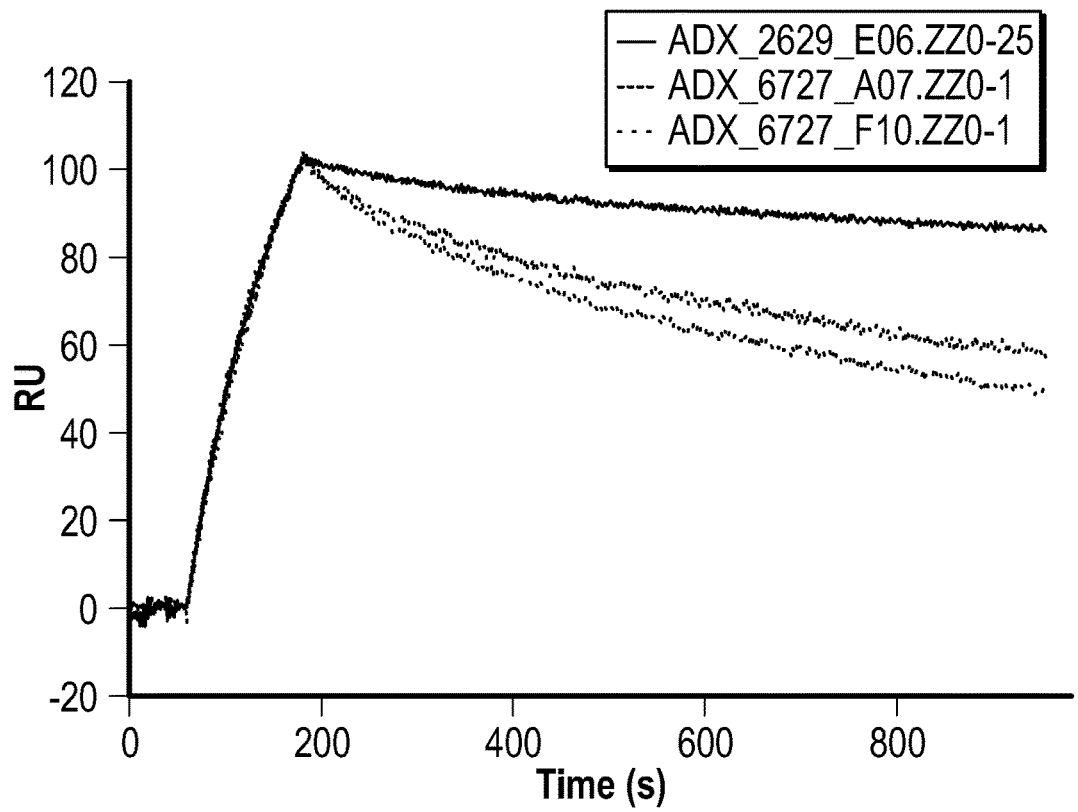
Figure 3D:
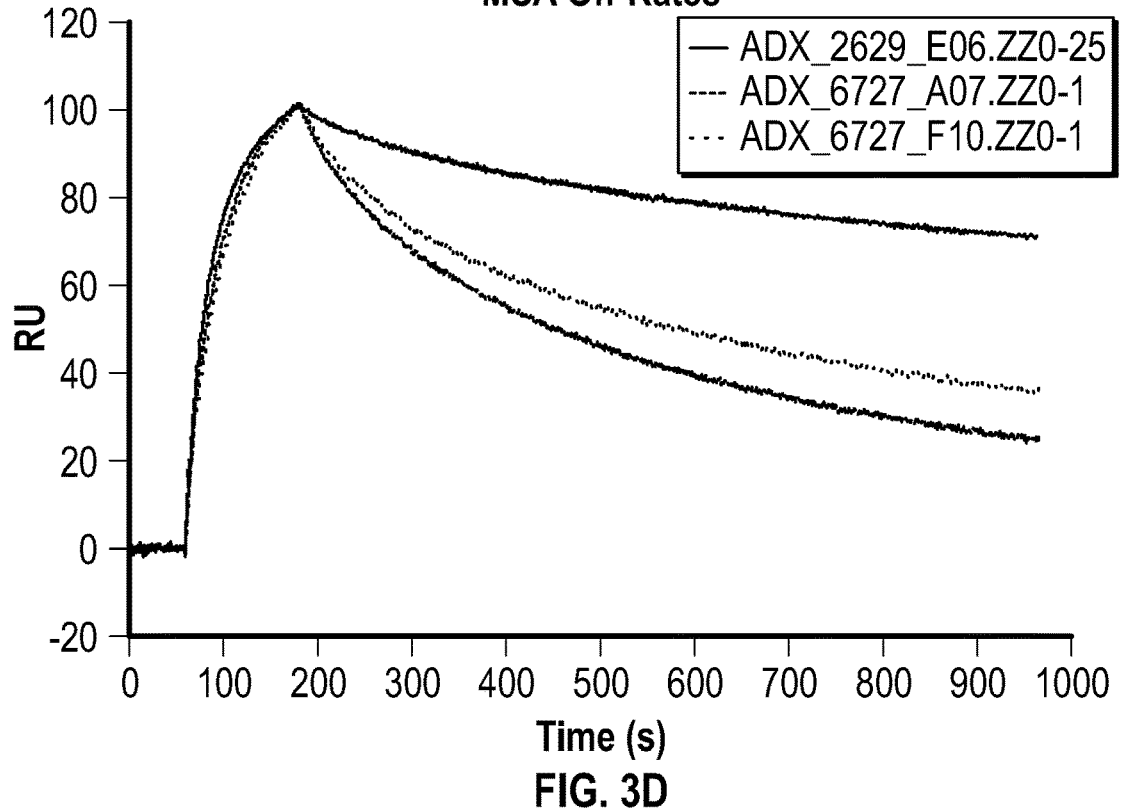
Figure 4A:
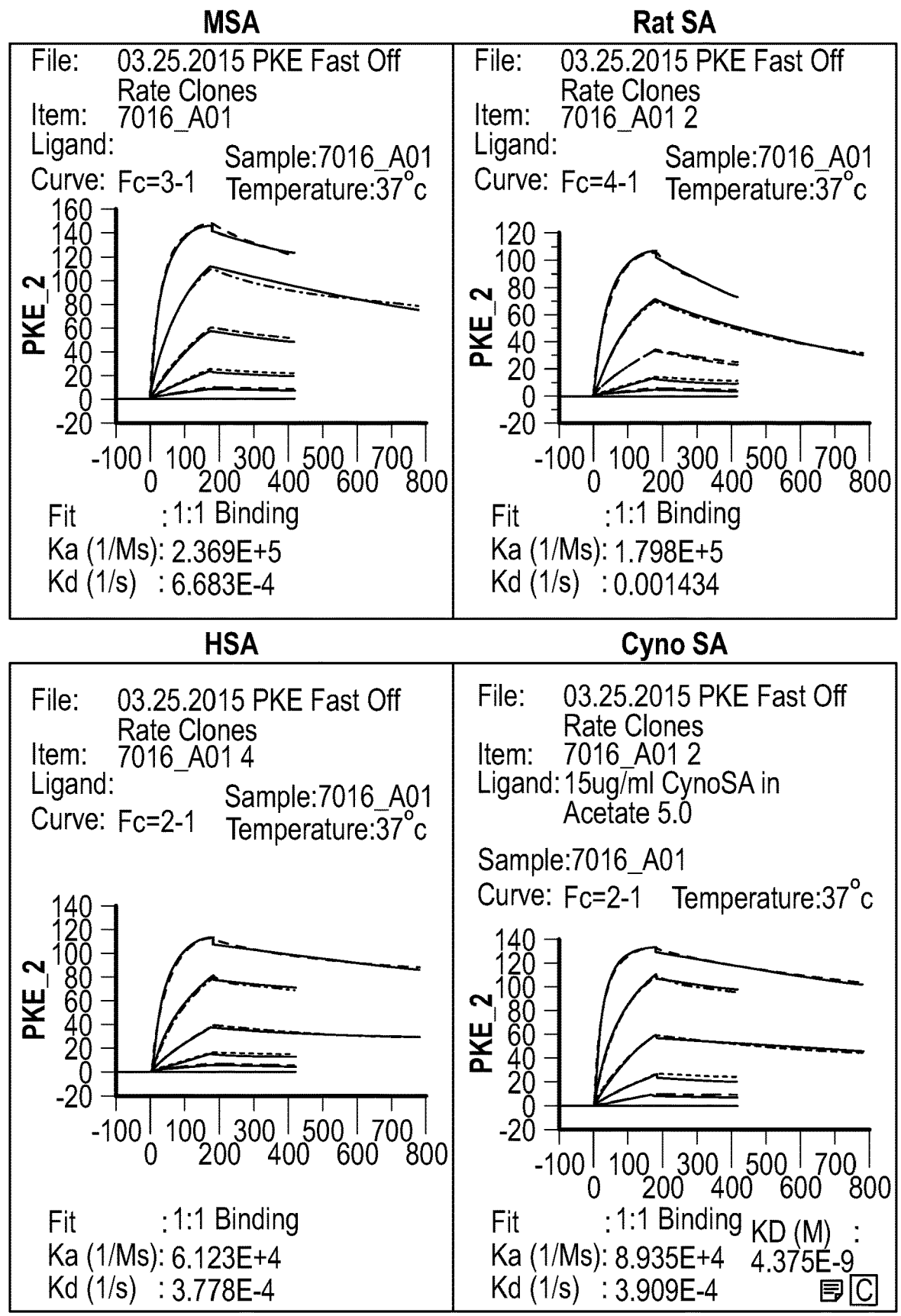
FIGS. 4A-4D are SPR kinetics data of the parent Adnectin (ADX_7016_A01; PKE2), and 7016_C03, 7016_E02, and 7016_G01 Adnectins for determining affinities to HSA, MSA, rat serum albumin (rat SA), and cynomolgus serum albumin (cyno SA).
Figure 4B:
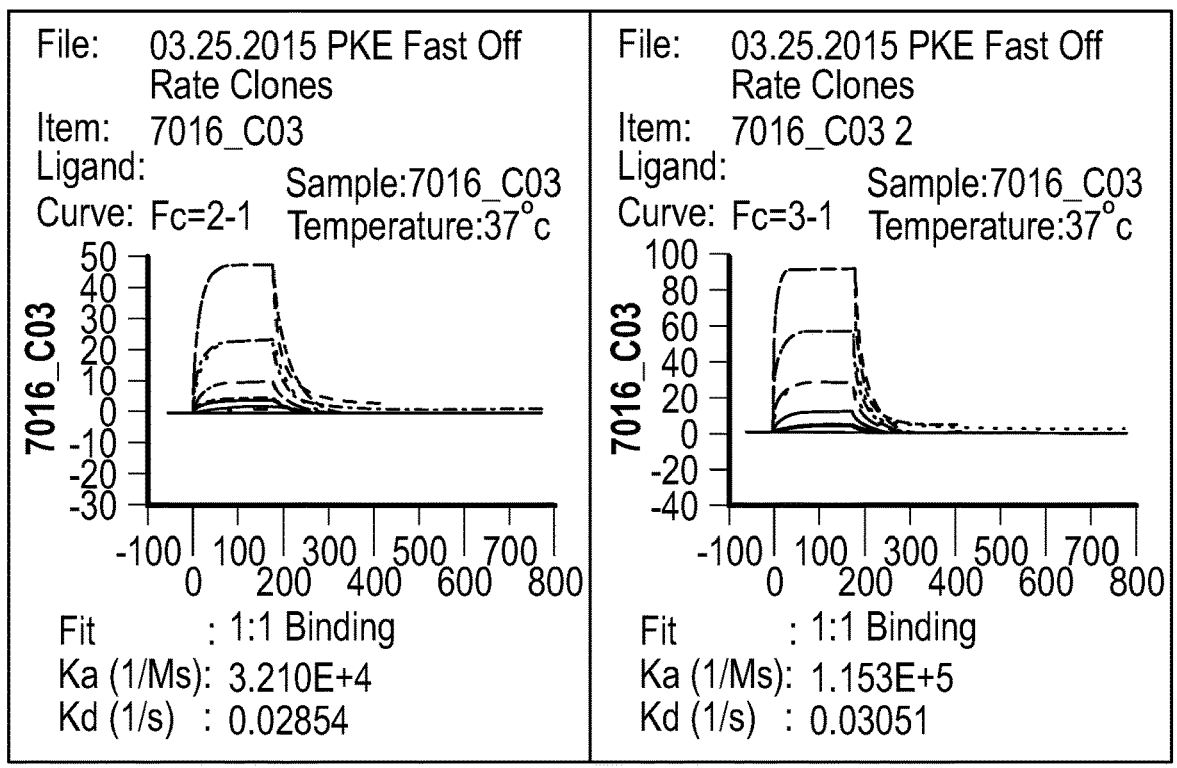
Figure 4B:
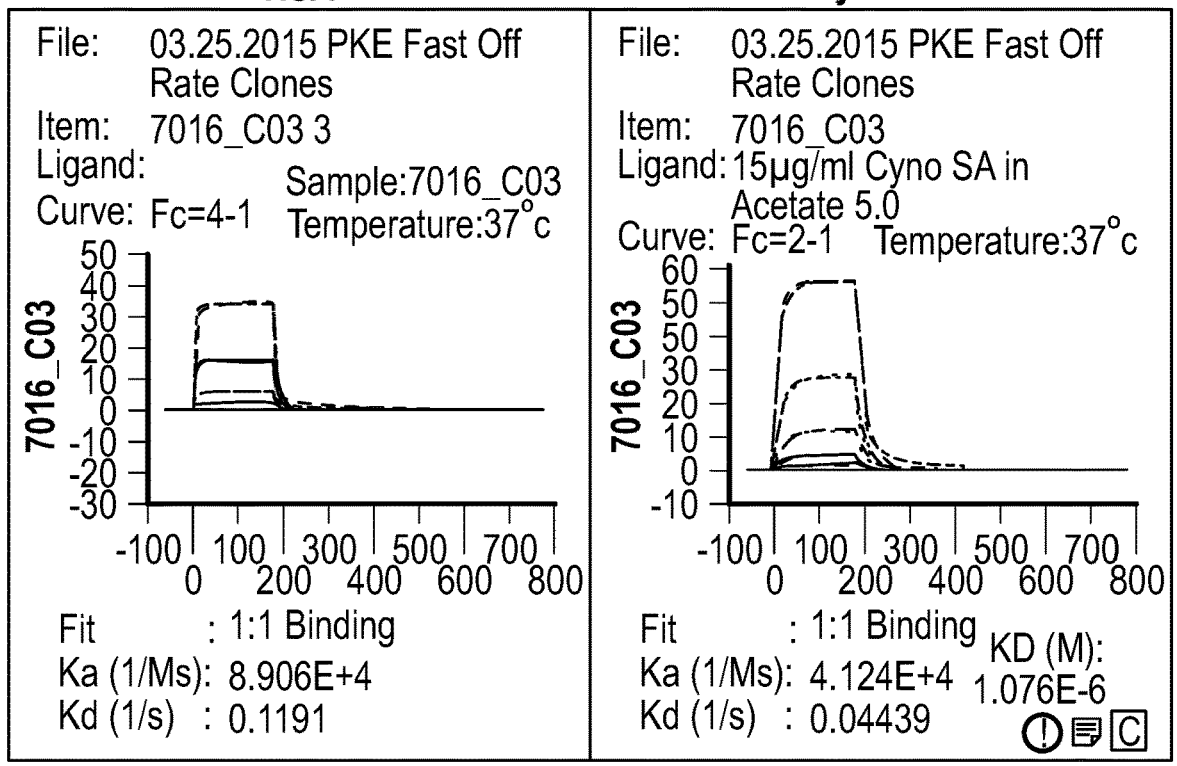
Figure 4C:
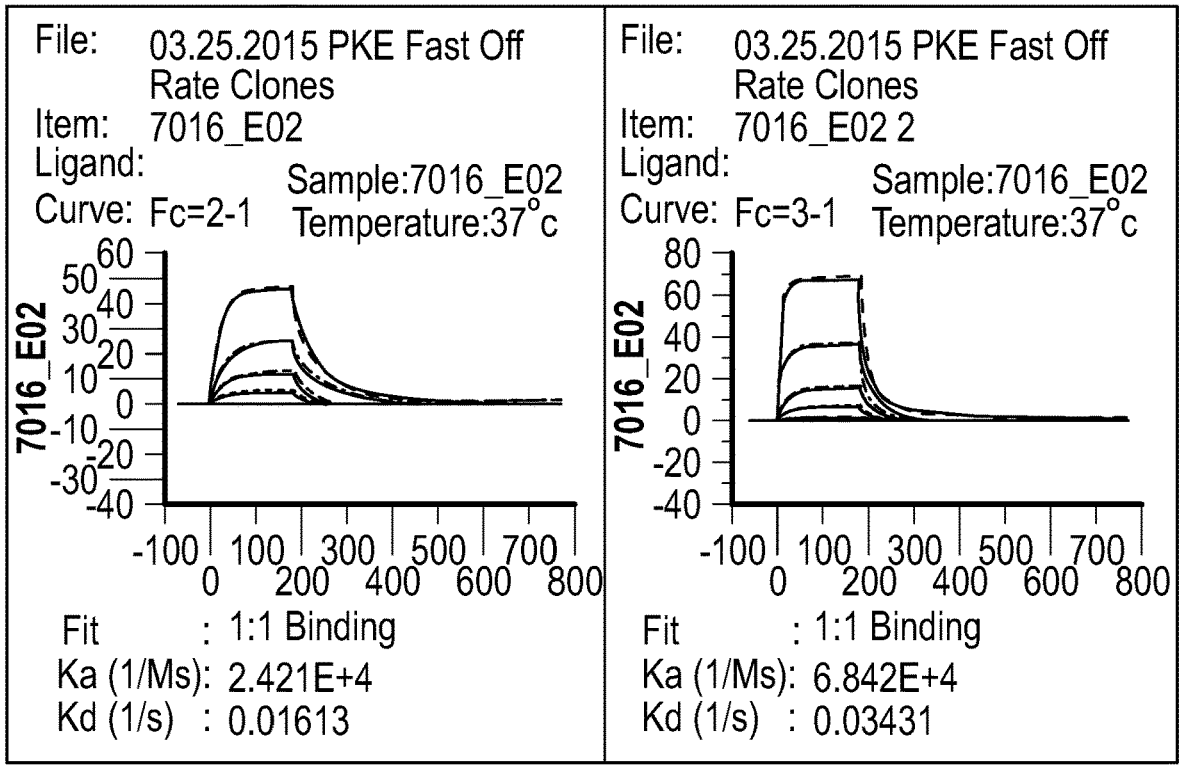
Figure 4C:
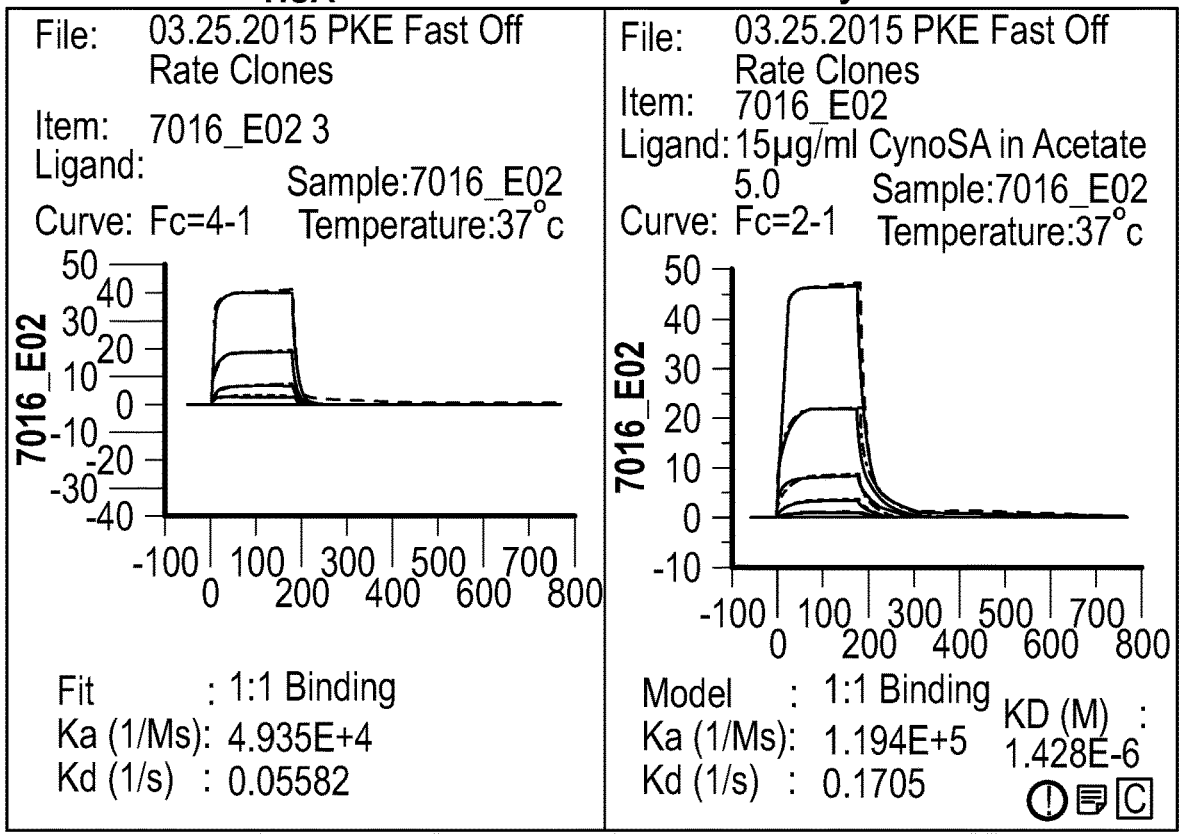
Figure 4D:
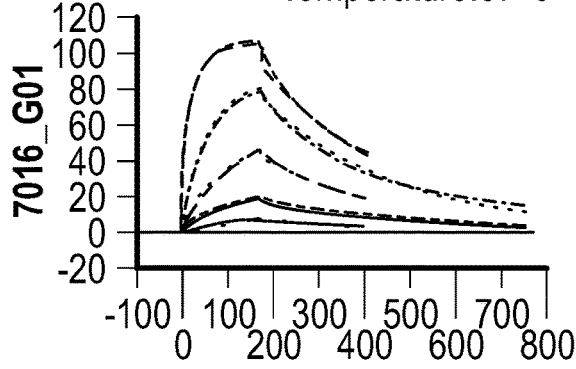
Figure 4D:
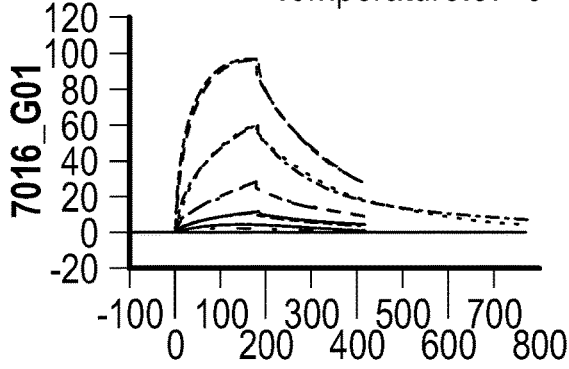
Figure 4D:
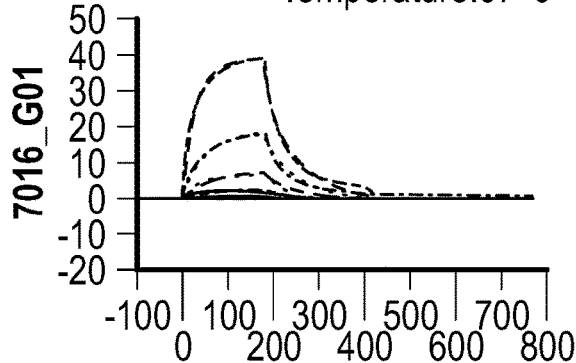
Figure 4D:
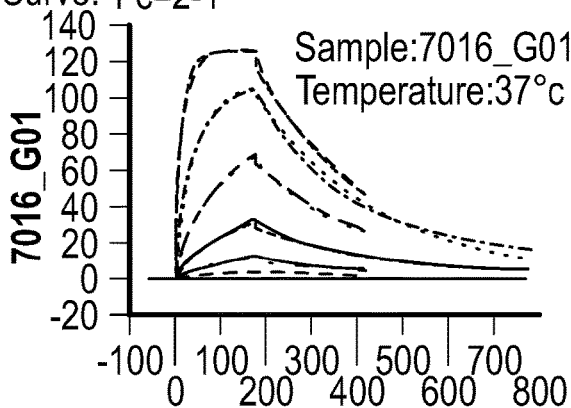

As shown in FIGS. 1 and 2, HSA off-rate sensograms (obtained by SPR analysis) correlated with DB ELISA binning.

An additional 15 variant HSA binding Adnectins were selected for further analysis. A summary of SPR and ELISA data for these variants, including both HSA and MSA binding data, are provided in Table 5, and off-rate sensograms for these variants are provided in FIG. 3.

TABLE 5

| ADX ID | HSA kd (s-1) | HSA kd/Parent kd | HSA Binding (RU) | HSA DB ELISA YMIN OBS (OD450) | HSA DB ELISA YMAX OBS (OU450) | MSA kd (s-1) | MSA kd/Parent kd | MSA Binding (RU) | MSA DB ELISA YMIN OBS (OD450) | MSA DB ELISA YMAX OBS (OD450) |
|---|---|---|---|---|---|---|---|---|---|---|
| 7016_A01 (parent) | 2.69E-04 | | 54 | 90 | 94 | 4.28E-04 | | 95 | 95 | 98 |
| 6727_G10 (Y35S/K85A) | 8.92E-04 | 3.3 | 27 | 54 | 96 | 1.38E-03 | 3.2 | 63 | 54 | 100 |
| 6727_G06 (Y35A/K85S) | 1.05E-03 | 3.9 | 26 | 69 | 98 | 1.43E-03 | 3.3 | 66 | 40 | 95 |
| 6727_F10 (Y35A/K85T) | 1.09E-03 | 4.0 | 22 | 61 | 98 | 1.56E-03 | 3.6 | 55 | 39 | 98 |
| 6727_B04 (Y35S/K85S) | 1.10E-03 | 4.1 | 23 | 62 | 99 | 1.42E-03 | 3.3 | 62 | 74 | 95 |
| 6727_A07 (Y44S/K85T) | 1.29E-03 | 4.8 | 28 | 60 | 98 | 2.22E-03 | 5.2 | 56 | 31 | 94 |
| 6727_G02 (Y44S) | 1.50E-03 | 5.6 | 33 | 38 | 95 | 2.13E-03 | 5.0 | 64 | 15 | 91 |
| 6727_F07 (Y44S/K85A) | 1.76E-03 | 6.5 | 35 | 44 | 96 | 2.77E-03 | 6.5 | 62 | 20 | 96 |
| 6727_G04 (Y44S/K85S) | 1.77E-03 | 6.6 | 28 | 75 | 99 | 2.59E-03 | 6.0 | 56 | 46 | 94 |
| 6727_D03 (L41S) | 7.77E-03 | 28.9 | 24 | 3 | 33 | 1.34E-02 | 31.3 | 43 | 1 | 54 |
| 6727_E08 (L38T) | 8.15E-03 | 30.3 | 25 | 2 | 12 | 2.48E-02 | 57.8 | 30 | 1 | 12 |
| 6727_H10 (L41S/K85S) | 8.60E-03 | 32.0 | 19 | 5 | 39 | 1.46E-02 | 34.0 | 35 | 1 | 59 |
| 6727_B09 (L38T/K85T) | 9.21E-03 | 34.3 | 19 | 2 | 16 | 2.62E-02 | 61.2 | 26 | 1 | 27 |
| 6727_H08 (L38T/K85T) | 1.00E-02 | 37.3 | 18 | 2 | 17 | 2.84E-02 | 66.3 | 23 | 1 | 21 |
| 6727_H06 (Y44Q/K85T) | 1.42E-02 | 52.7 | 24 | 1 | 12 | 1.43E-02 | 33.5 | 43 | 1 | 33 |
| 6727_B03 (Y44Q) | 2.14E-02 | 79.4 | 14 | 2 | 18 | 1.79E-02 | 41.9 | 33 | 1 | 23 |

*Note:
Off-rates for HTTP proteins measured at 25° C. The numbering of the amino acid substitutions listed in parentheses under the name of the Adnectins is based on the core amino acid sequence of ADX_7016_A01 (SEQ ID NO: 23).

Collectively, the data show that the 4pt DB HSA/MSA ELISA data correlated well with the off-rate screen, i.e., HSA binding Adnectins with slower off-rates were better binders in ELISA (with a few exceptions).

Example 3: Binding Affinity of Fast Off-Rate PKE3 Variants for Serum Albumins Three variant HSA binding Adnectins were tested for binding affinity to HSA, MSA, rat serum albumin (rat SA), and cynomolgus monkey serum albumin (cynoSA) using SPR analysis.

The SPR was conducted as follows. Full length human, mouse, rat and cynomolgus monkey serum albumin were immobilized on a Biacore T series CM5 chip at 15 ug/mL in 10 mM acetate buffer (pH 5.0) buffer using standard NHS/EDC coupling, to a surface density of approximately 1000-1100 RU. For off-rate measurements at 25° C., PKE Adnectins were applied as analytes at 500 nM in HBS-P+(0.01 M HEPES pH 7.4, 0.15 M NaCl, 0.005% v/v Surfactant P20) running buffer at a flow rate of 20ul/min for 120s over the immobilized albumins, followed by 800s for dissociation. For kinetic affinity measurements carried out at 37° C., a concentration series of the PKE Adnectins (0.05-333 nM) was applied in HBS-P+running buffer at a flow rate of 40ul/min for 180s followed by dissociation for 240s or 600s. Regeneration of the chip surface between cycles was accomplished with two 30 second pulses of 10 mM Glycine, pH 2.0. Kinetic traces of reference-subtracted sensorgrams were fit to a 1:1 binding model for affinity using the Biaevaluation software. Only the dissociation phase was fit for determination of off-rates.

The results are summarized in Table 6, and the sensograms are provided in FIGS. 4A-4D.

TABLE 6

| Adnectin ID | Ligand | ka (1/Ms) | kd (1/s) | KD (nM) | Rmax (RU) |
|---|---|---|---|---|---|
| ADX_7016_A01 (PKE2) | HSA | 6.12E+04 | 3.78E-04 | 6.2 | 140 |
| | cynoSA | 8.94E+04 | 3.91E-04 | 4.4 | 140 |
| | MSA | 2.37E+05 | 6.68E-04 | 2.8 | 115 |
| | Rat SA | 1.80E+05 | 1.43E-03 | 8.0 | 120 |
| ADX_7016_G01 (Y44S) | HSA | 3.82E+04 | 3.20E-03 | 83.7 | 110 |
| | cynoSA | 6.25E+04 | 4.26E-03 | 68.1 | 125 |
| | MSA | 2.35E+05 | 6.29E-03 | 26.8 | 100 |
| | Rat SA | 3.31E+05 | 3.46E-02 | 104 | 40 |
| ADX_7016_E02 (L38T) | HSA | 2.42E+04 | 1.61E-02 | 666 | 50 |
| | cynoSA | 1.19E+05 | 1.71E-01 | 1430 | 45 |
| | MSA | 6.84E+04 | 3.43E-02 | 502 | 75 |
| | Rat SA | 4.94E+04 | 5.58E-02 | 1130 | 45 |
| ADX_7016_C03 (Y44Q) | HSA | 3.21E+04 | 2.85E-02 | 889 | 50 |
| | cynoSA | 4.12E+04 | 4.44E-02 | 1080 | 60 |
| | MSA | 1.15E+05 | 3.05E-02 | 265 | 90 |
| | Rat SA | 8.91E+04 | 1.19E-01 | 1340 | 35 |

Note:
The cynoSA experiment was performed using a different Biacore chip

Example 4: Fast Off-Rate PKE3 Adnectins Exhibit Faster Clearance than Wild-Type Parent PKE2 Adnectin The clearance of the three PKE3 Adnectins from Example 3 were tested in vivo in Sprague Dawley rats (n=2/group). Rats were administered a single IV dose of each PKE3 Adnectin (2 mg/kg), and plasma was collected at the following time points: 5 min, 1 hr, 2 hrs, 4 hrs, 8 hrs, 1 day, 2 days, 3 days, 5 days, and 7 days.

Figure 5:
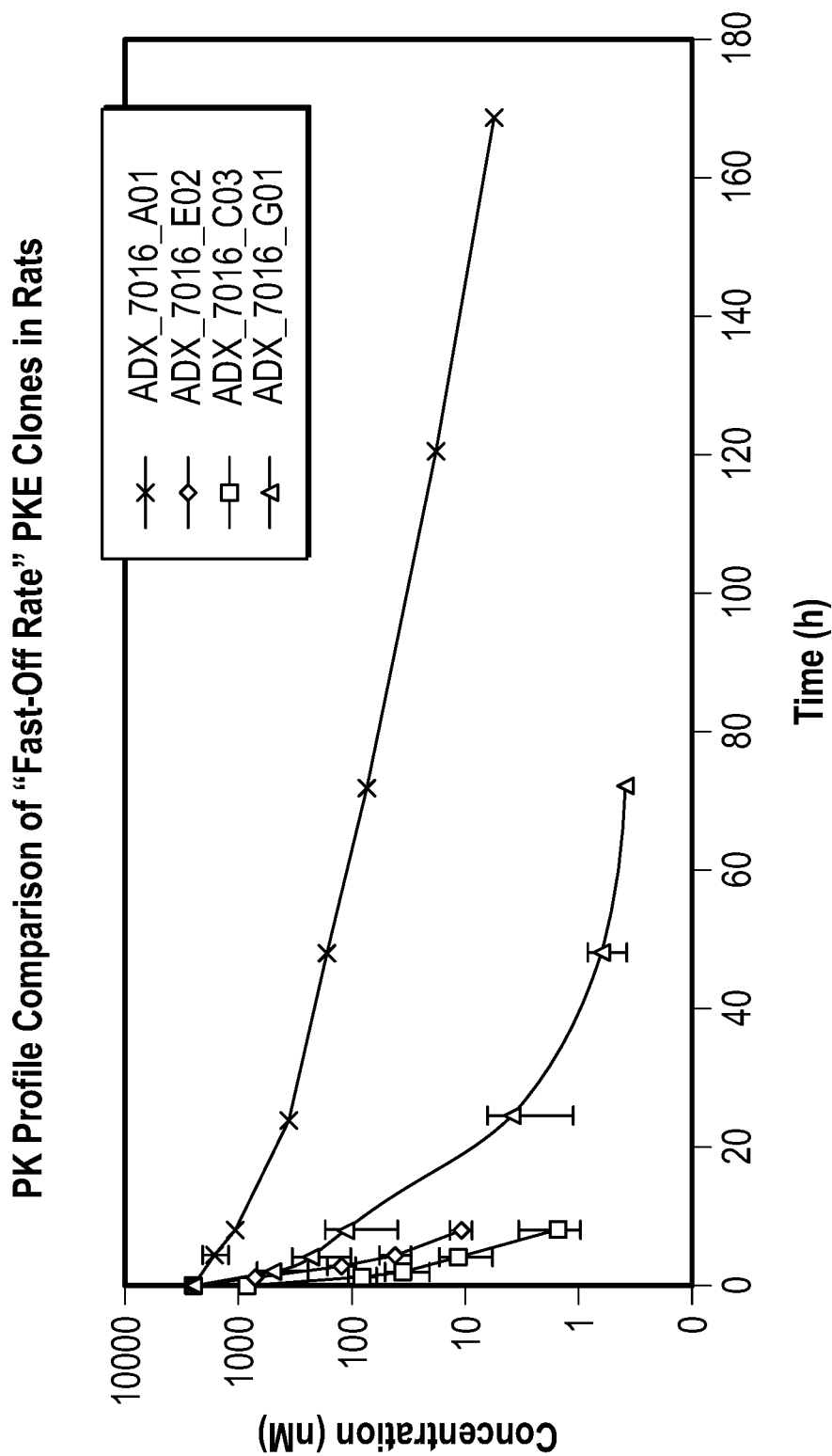
FIG. 5 is a graph depicting the plasma half-lives in rats of the parent Adnectin (ADX_7016_A01; PKE2), and 7016_C03, 7016_E02, and 7016_G01 Adnectins.
Figure 6:
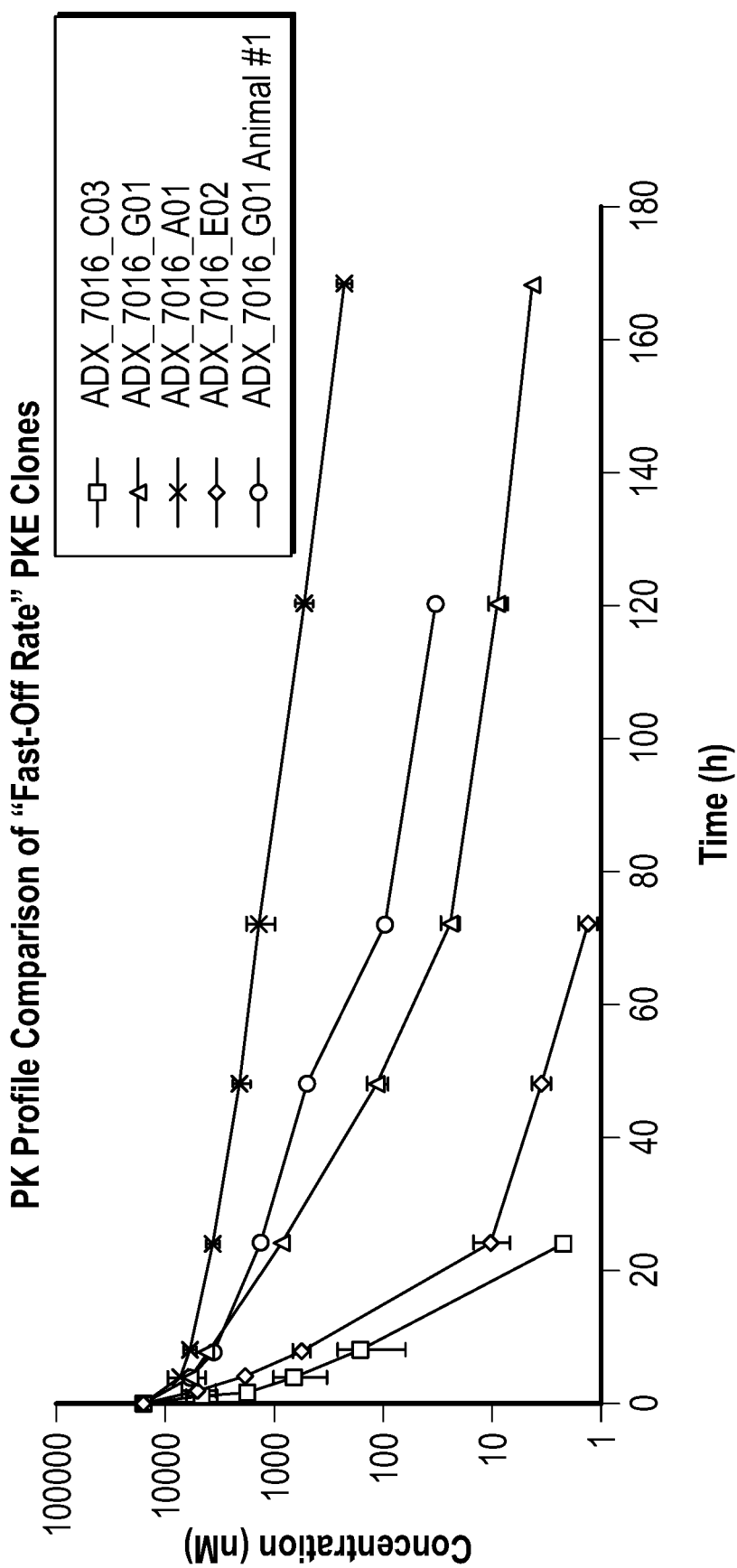
FIG. 6 is a graph depicting the plasma half-lives in mice of the parent Adnectin (ADX_7016_A01; PKE2), and 7016_C03, 7016_E02, and 7016_G01 Adnectins.

As shown in FIG. 5, the parent PKE2 Adnectin (ADX_7016_A01) exhibited the longest half-life, whereas the three PKE3 Adnectins had shorter half-lives. Similar results were observed in mice (FIG. 6).

TABLE 7

SUMMARY OF SEQUENCES

| SEQ ID | Description | Sequence |
|---|---|---|
| 1 | Wild-type human $^{10}$Fn3 domain | VSDVPRDLEVVAA<u>TPTSLLISW</u>DAPAVTVRYYRITY<u>GETGGNSPVQEF</u>TVPGSKSTATISGL<u>KPGVD</u>YTITVYAVTGRGDSPASSKPISINYRT |
| 2 | Wild-type human $^{10}$Fn3 domain w/loop sequences generically defined | VSDVPRDLEVVAA (X)$_u$LLISW (X)$_v$YRITY (X)$_w$FTV (X)$_x$ATISGL (X)$_y$YTITVYA (X)$_z$ISINYRT |
| 3 | N-terminal leader | MGVSDVPRDL |
| 4 | N-terminal leader | GVSDVPRDL |
| 5 | N-terminal leader | X$_n$SDVPRDL |
| 6 | N-terminal leader | X$_n$DVPRDL |
| 7 | N-terminal leader | X$_n$VPRDL |
| 8 | N-terminal leader | X$_n$PRDL |
| 9 | N-terminal leader | X$_n$RDL |
| 10 | N-terminal leader | X$_n$DL |
| 11 | N-terminal leader | MASTSG |
| 12 | C-terminal tail | EIEK |
| 13 | C-terminal tail | EGSGC |
| 14 | C-terminal tail | EIEKPCQ |
| 15 | C-terminal tail | EIEKPSQ |
| 16 | C-terminal tail | EIEKP |
| 17 | C-terminal tail | EIEKPS |
| 18 | C-terminal tail | EIEKPC |
| 19 | C-terminal tail | EIDK |
| 20 | C-terminal tail | EIDKPCQ |
| 21 | C-terminal tail | EIDKPSQ |
| 22 | 6X His tail | HHHHHH |
| 23 | 7016_A01 core (aka 2629_E06; parent PKE2 Adnectin); CD and FG loops are underlined | EVVAATPTSLLISWDAPAVTVRYYRITY<u>GREVQKYSDLGPLYIYQEFT</u>VPGSKSTATISGLKPGVDYTITVYA<u>VTGSGESPASSKP</u>ISINYRT |

TABLE 7-continued

SUMMARY OF SEQUENCES

| SEQ ID | Description | Sequence |
|---|---|---|
| 24 | 7016_A01 | MGVSDVPRDLEVVAATPTSLLISWDAPAVTVRYYRITY<u>GREVQKYSDLGPLYIYQE</u>FTVPGSKSTATISGLKPGVDYTITVYA<u>VTGSGESPASSKP</u>ISINYRTEIDKPSQHHHHHH |
| 25 | 7016_A01 w/o his tag, C-terminal tail, and N-terminal MG | VSDVPRDLEVVAATPTSLLISWDAPAVTVRYYRITY<u>GREVQKYSDLGPLYIYQE</u>FTVPGSKSTATISGLKPGVDYTITVYA<u>VTGSGESPASSKP</u>ISINYRT |
| 26 | 7016_A01 core with C-terminal proline | EVVAATPTSLLISWDAPAVTVRYYRITY<u>GREVQKYSDLGPLYIYQE</u>FTVPGSKSTATISGLKPGVDYTITVYA<u>VTGSGESPASSKP</u>ISINYRTP |
| 27 | 7016_A01 w/o his tag, C-terminail tail, and N-terminal MG and w/ C-terminal proline | VSDVPRDLEVVAATPTSLLISWDAPAVTVRYYRITY<u>GREVQKYSDLGPLYIYQE</u>FTVPGSKSTATISGLKPGVDYTITVYA<u>VTGSGESPASSKP</u>ISINYRTP |
| 28 | 7016_A01 CD loop | GREVQKYSDLGPLYIYQE |
| 29 | 7016_A01 FG loop | VTGSGESPASSKP |
| 30 | 7016_G01 (Y44S) core (aka 6727_G02) | EVVAATPTSLLISWDAPAVTVRYYRITY<u>GREVQKYSDLGPLYI$\underline{S}$QE</u>FTVPGSKSTATISGLKPGVDYTITVYA<u>VTGSGESPASSKP</u>ISINYRT |
| 31 | 7016_G01 | MGVSDVPRDLEVVAATPTSLLISWDAPAVTVRYYRITY<u>GREVQKYSDLGPLYI$\underline{S}$QE</u>FTVPGSKSTATISGLKPGVDYTITVYA<u>VTGSGESPASSKP</u>ISINYRTEIDKPSQHHHHHH |
| 32 | 7016_G01 w/o his tag, C-terminal tail, and N-terminal MG | VSDVPRDLEVVAATPTSLLISWDAPAVTVRYYRITY<u>GREVQKYSDLGPLYI$\underline{S}$QE</u>FTVPGSKSTATISGLKPGVDYTITVYA<u>VTGSGESPASSKP</u>ISINYRT |
| 33 | 7016_G01 core with C-terminal proline | EVVAATPTSLLISWDAPAVTVRYYRITY<u>GREVQKYSDLGPLYI$\underline{S}$QE</u>FTVPGSKSTATISGLKPGVDYTITVYA<u>VTGSGESPASSKP</u>ISINYRTP |
| 34 | 7016_G01 w/o his tag, C-terminail tail, and N-terminal MG and w/ C-terminal proline | VSDVPRDLEVVAATPTSLLISWDAPAVTVRYYRITY<u>GREVQKYSDLGPLYI$\underline{S}$QE</u>FTVPGSKSTATISGLKPGVDYTITVYA<u>VTGSGESPASSKP</u>ISINYRTP |
| 35 | 7016_G01 CD loop | GREVQKYSDLGPLYI$\underline{S}$QE |
| 36 | 7016_E02 (L381) core (aka 6727_E08) | EVVAATPTSLLISWDAPAVTVRYYRITY<u>GREVQKYSD$\underline{T}$GPLYIYQE</u>FTVPGSKSTATISGLKPGVDYTITVYA<u>VTGSGESPASSKP</u>ISINYRT |
| 37 | 7016_E02 | MGVSDVPRDLEVVAATPTSLLISWDAPAVTVRYYRITY<u>GREVQKYSD$\underline{T}$GPLYIYQE</u>FTVPGSKSTATISGLKPGVDYTITVYA<u>VTGSGESPASSKP</u>ISINYRTEIDKPSQHHHHHH |
| 38 | 7016_E02 w/o his tag, C-terminal tail, and N-terminal MG | VSDVPRDLEVVAATPTSLLISWDAPAVTVRYYRITY<u>GREVQKYSD$\underline{T}$GPLYIYQE</u>FTVPGSKSTATISGLKPGVDYTITVYA<u>VTGSGESPASSKP</u>ISINYRT |

TABLE 7-continued

SUMMARY OF SEQUENCES

| SEQ ID | Description | Sequence |
|---|---|---|
| 39 | 7016_E02 core with C-terminal proline | EVVAATPTSLLISWDAPAVTVRYYRITYGREVQKYSDTGPLYIYQEFT VPGSKSTATISGLKPGVDYTITVYAVTGSGESPASSKPISINYRTP |
| 40 | 7016_E02 w/o his tag, C-terminail tail, and N-terminal MG and w/ C-terminal proline | VSDVPRDLEVVAATPTSLLISWDAPAVTVRYYRITYGREVQKYSDTGP LYIYQEFTVPGSKSTATISGLKPGVDYTITVYAVTGSGESPASSKPIS INYRTP |
| 41 | 7016_E02 CD loop | GREVQKYSDTGPLYIYQE |
| 42 | 7016_C03 (Y44Q) core (aka 6727_B03) | EVVAATPTSLLISWDAPAVTVRYYRITYGREVQKYSDLGPLYIQQEFT VPGSKSTATISGLKPGVDYTITVYAVTGSGESPASSKPISINYRT |
| 43 | 7016_C03 | MGVSDVPRDLEVVAATPTSLLISWDAPAVTVRYYRITYGREVQKYSDL GPLYIQQEFTVPGSKSTATISGLKPGVDYTITVYAVTGSGESPASSKP ISINYRTEIDKPSQHHHHHH |
| 44 | 7016_C03 w/o his tag, C-terminal tail, and N-terminal MG | VSDVPRDLEVVAATPTSLLISWDAPAVTVRYYRITYGREVQKYSDLGP LYIQQEFTVPGSKSTATISGLKPGVDYTITVYAVTGSGESPASSKPIS INYRT |
| 45 | 7016_C03 core with C-terminal proline | EVVAATPTSLLISWDAPAVTVRYYRITYGREVQKYSDLGPLYIQQEFT VPGSKSTATISGLKPGVDYTITVYAVTGSGESPASSKPISINYRTP |
| 46 | 7016_C03 w/o his tag, C-terminail tail, and N-terminal MG and w/ C-terminal proline | VSDVPRDLEVVAATPTSLLISWDAPAVTVRYYRITYGREVQKYSDLGP LYIQQEFTVPGSKSTATISGLKPGVDYTITVYAVTGSGESPASSKPIS INYRTP |
| 47 | 7016_C03 CD loop | GREVQKYSDLGPLYIQQE |
| 48 | ADX_6727_C01 (K85A) core | EVVAATPTSLLISWDAPAVTVRYYRITYGREVQKYSDLGPLYIYQEFT VPGSKSTATISGLKPGVDYTITVYAVTGSGESPASSAPISINYRT |
| 49 | ADX_6727_C01 | MGVSDVPRDLEVVAATPTSLLISWDAPAVTVRYYRITYGREVQKYSDL GPLYIYQEFTVPGSKSTATISGLKPGVDYTITVYAVTGSGESPASSAP ISINYRTEIDKPSQHHHHHH |
| 50 | ADX_6727_C01 FG loop | VTGSGESPASSAP |
| 51 | ADX_6727_D01 (K85T) core | EVVAATPTSLLISWDAPAVTVRYYRITYGREVQKYSDLGPLYIYQEFT VPGSKSTATISGLKPGVDYTITVYAVTGSGESPASSTPISINYRT |
| 52 | ADX_6727_D01 | MGVSDVPRDLEVVAATPTSLLISWDAPAVTVRYYRITYGREVQKYSDL GPLYIYQEFTVPGSKSTATISGLKPGVDYTITVYAVTGSGESPASSTP ISINYRTEIDKPSQHHHHHH |
| 53 | ADX_6727_D01 FG loop | VTGSGESPASSTP |

TABLE 7-continued

SUMMARY OF SEQUENCES

| SEQ ID | Description | Sequence |
|---|---|---|
| 54 | ADX_6727_B01 (K85S) core | EVVAATPTSLLISWDAPAVTVRYYRITYGREVQKYSDLGPLYIYQEFT VPGSKSTATISGLKPGVDYTITVYAVTGSGESPASSSPISINYRT |
| 55 | ADX_6727_B01 | MGVSDVPRDLEVVAATPTSLLISWDAPAVTVRYYRITYGREVQKYSDL GPLYIYQEFTVPGSKSTATISGLKPGVDYTITVYAVTGSGESPASSSP ISINYRTEIDKPSQHHHHHH |
| 56 | ADX_6727_B01 FG loop | VTGSGESPASSSP |
| 57 | ADX_6727_B04 (Y35S/K85S) core | EVVAATPTSLLISWDAPAVTVRYYRITYGREVQKSSDLGPLYIYQEFT VPGSKSTATISGLKPGVDYTITVYAVTGSGESPASSSPISINYRT |
| 58 | ADX_6727_B04 | MGVSDVPRDLEVVAATPTSLLISWDAPAVTVRYYRITYGREVQKSSDL GPLYIYQEFTVPGSKSTATISGLKPGVDYTITVYAVTGSGESPASSSP ISINYRTEIDKPSQHHHHHH |
| 59 | ADX_6727_B04 CD loop | GREVQKSSDLGPLYIYQE |
| 56 | ADX_6727_B04 FG loop | VTGSGESPASSSP |
| 60 | ADX_6727_G10 (Y35S/K85A) core | EVVAATPTSLLISWDAPAVTVRYYRITYGREVQKSSDLGPLYIYQEFT VPGSKSTATISGLKPGVDYTITVYAVTGSGESPASSAPISINYRT |
| 61 | ADX_6727_G10 | MGVSDVPRDLEVVAATPTSLLISWDAPAVTVRYYRITYGREVQKSSDL GPLYIYQEFTVPGSKSTATISGLKPGVDYTITVYAVTGSGESPASSAP ISINYRTEIDKPSQHHHHHH |
| 59 | ADX_6727_G10 CD loop | GREVQKSSDLGPLYIYQE |
| 50 | ADX_6727_G10 FG loop | VTGSGESPASSAP |
| 62 | ADX_6727_C07 (R30A/K85S) core | EVVAATPTSLLISWDAPAVTVRYYRITYGAEVQKYSDLGPLYIYQEFT VPGSKSTATISGLKPGVDYTITVYAVTGSGESPASSSPISINYRT |
| 63 | ADX_6727_C07 | MGVSDVPRDLEVVAATPTSLLISWDAPAVTVRYYRITYGAEVQKYSDL GPLYIYQEFTVPGSKSTATISGLKPGVDYTITVYAVTGSGESPASSSP ISINYRTEIDKPSQHHHHHH |
| 64 | ADX_6727_C07 CD loop | GAEVQKYSDLGPLYIYQE |
| 56 | ADX_6727_C07 FG loop | VTGSGESPASSSP |
| 65 | ADX_6727S03 (Y35S) core | EVVAATPTSLLISWDAPAVTVRYYRITYGREVQKSSDLGPLYIYQEFT VPGSKSTATISGLKPGVDYTITVYAVTGSGESPASSKPISINYRT |
| 66 | ADX_6727_C03 | MGVSDVPRDLEVVAATPTSLLISWDAPAVTVRYYRITYGREVQKSSDL GPLYIYQEFTVPGSKSTATISGLKPGVDYTITVYAVTGSGESPASSKP ISINYRTEIDKPSQHHHHHH |

TABLE 7-continued

SUMMARY OF SEQUENCES

| SEQ ID | Description | Sequence |
|---|---|---|
| 59 | ADX_6727_C03 CD loop | GREVQKSSDLGPLYIYQE |
| 67 | ADX_6727_D02 (R30N) core | EVVAATPTSLLISWDAPAVTVRYYRITYGNEVQKYSDLGPLYIYQEFT VPGSKSTATISGLKPGVDYTITVYAVTGSGESPASSKPISINYRT |
| 68 | ADX_6727_D02 | MGVSDVPRDLEVVAATPTSLLISWDAPAVTVRYYRITYGNEVQKYSDL GPLYIYQEFTVPGSKSTATISGLKPGVDYTITVYAVTGSGESPASSKP ISINYRTEIDKPSQHHHHHH |
| 69 | ADX_6727_D02 CD loop | GNEVQKYSDLGPLYIYQE |
| 70 | ADX_6727_F06 (L41A/K85T) core | EVVAATPTSLLISWDAPAVTVRYYRITYGREVQKYSDLGPAYIYQEFT VPGSKSTATISGLKPGVDYTITVYAVTGSGESPASSTPISINYRT |
| 71 | ADX_6727_F06 | MGVSDVPRDLEVVAATPTSLLISWDAPAVTVRYYRITYGREVQKYSDL GPAYIYQEFTVPGSKSTATISGLKPGVDYTITVYAVTGSGESPASSTP ISINYRTEIDKPSQHHHHHH |
| 72 | ADX_6727_F06 CD loop | GREVQKYSDLGPAYIYQE |
| 53 | ADX_6727_F06 FG loop | VTGSGESPASSTP |
| 73 | ADX_6727_G01 (L41A) core | EVVAATPTSLLISWDAPAVTVRYYRITYGREVQKYSDLGPAYIYQEFT VPGSKSTATISGLKPGVDYTITVYAVTGSGESPASSKPISINYRT |
| 74 | ADX_6727_G01 | MGVSDVPRDLEVVAATPTSLLISWDAPAVTVRYYRITYGREVQKYSDL GPAYIYQEFTVPGSKSTATISGLKPGVDYTITVYAVTGSGESPASSKP ISINYRTEIDKPSQHHHHHH |
| 72 | ADX_6727_G01 CD loop | GREVQKYSDLGPAYIYQE |
| 75 | ADX_6727_F03 (I43A) core | EVVAATPTSLLISWDAPAVTVRYYRITYGREVQKYSDLGPLYAYQEFT VPGSKSTATISGLKPGVDYTITVYAVTGSGESPASSKPISINYRT |
| 76 | ADX_6727_F03 | MGVSDVPRDLEVVAATPTSLLISWDAPAVTVRYYRITYGREVQKYSDL GPLYAYQEFTVPGSKSTATISGLKPGVDYTITVYAVTGSGESPASSKP ISINYRTEIDKPSQHHHHHH |
| 77 | ADX_6727_F03 CD loop | GREVQKYSDLGPLYAYQE |
| 78 | ADX_6727_D06 (Y44A/K85S) core | EVVAATPTSLLISWDAPAVTVRYYRITYGREVQKYSDLGPLYIAQEFT VPGSKSTATISGLKPGVDYTITVYAVTGSGESPASSSPISINYRT |
| 79 | ADX_6727_D06 | MGVSDVPRDLEVVAATPTSLLISWDAPAVTVRYYRITYGREVQKYSDL GPLYIAQEFTVPGSKSTATISGLKPGVDYTITVYAVTGSGESPASSSP ISINYRTEIDKPSQHHHHHH |
| 80 | ADX_6727_D06 CD loop | GREVQKYSDLGPLYIAQE |

TABLE 7-continued

SUMMARY OF SEQUENCES

| SEQ ID | Description | Sequence |
|---|---|---|
| 56 | ADX_6727_D06 FG loop | VTGSGESPASSSP |
| 81 | ADX_6727_F04 (Y44A/K85A) core | EVVAATPTSLLISWDAPAVTVRYYRITYGREVQKYSDLGPLYIAQEFT VPGSKSTATISGLKPGVDYTITVYAVTGSGESPASSAPISINYRT |
| 82 | ADX_6727_F04 | MGVSDVPRDLEVVAATPTSLLISWDAPAVTVRYYRITYGREVQKYSDL GPLYIAQEFTVPGSKSTATISGLKPGVDYTITVYAVTGSGESPASSAP ISINYRTEIDKPSQHHHHHH |
| 80 | ADX_6727_F04 CD loop | GREVQKYSDLGPLYIAQE |
| 50 | ADX_6727_F04 FG loop | VTGSGESPASSAP |
| 83 | ADX_6727_B05 (I43S/K85T) core | EVVAATPTSLLISWDAPAVTVRYYRITYGREVQKYSDLGPLYSYQEFT VPGSKSTATISGLKPGVDYTITVYAVTGSGESPASSTPISINYRT |
| 84 | ADX_6727_B05 | MGVSDVPRDLEVVAATPTSLLISWDAPAVTVRYYRITYGREVQKYSDL GPLYSAQEFTVPGSKSTATISGLKPGVDYTITVYAVTGSGESPASSTP ISINYRTEIDKPSQHHHHHH |
| 85 | ADX_6727_B05 CD loop | GREVQKYSDLGPLYSYQE |
| 53 | ADX_6727_B05 FG loop | VTGSGESPASSTP |
| 86 | ADX_6727_B11 (Q33D/K85S) core | EVVAATPTSLLISWDAPAVTVRYYRITYGREVDKYSDLGPLYSYQEFT VPGSKSTATISGLKPGVDYTITVYAVTGSGESPASSSPISINYRT |
| 87 | ADX_6727_B11 | MGVSDVPRDLEVVAATPTSLLISWDAPAVTVRYYRITYGREVDKYSDL GPLYIYQEFTVPGSKSTATISGLKPGVDYTITVYAVTGSGESPASSSP ISINYRTEIDKPSQHHHHHH |
| 88 | ADX_6727_B11 CD loop | GREVDKYSDLGPLYIYQE |
| 56 | ADX_6727_B11 FG loop | VTGSGESPASSSP |
| 89 | ADX_6727_D10 (Q33D/K85T) core | EVVAATPTSLLISWDAPAVTVRYYRITYGREVDKYSDLGPLYSYQEFT VPGSKSTATISGLKPGVDYTITVYAVTGSGESPASSTPISINYRT |
| 90 | ADX_6727_D10 | MGVSDVPRDLEVVAATPTSLLISWDAPAVTVRYYRITYGREVDKYSDL GPLYIYQEFTVPGSKSTATISGLKPGVDYTITVYAVTGSGESPASSTP ISINYRTEIDKPSQHHHHHH |
| 88 | ADX_6727_D10 CD loop | GREVDKYSDLGPLYIYQE |

TABLE 7-continued

SUMMARY OF SEQUENCES

| SEQ ID | Description | Sequence |
|---|---|---|
| 53 | ADX_6727_D10 FG loop | VTGSGESPASSTP |
| 91 | ADX_6727_B09 (L381/K85T) core | EVVAATPTSLLISWDAPAVTVRYYRITYGREVQKYSDTGPLYSYQEFT VPGSKSTATISGLKPGVDYTITVYAVTGSGESPASSTPISINYRT |
| 92 | ADX_6727_B09 | MGVSDVPRDLEVVAATPTSLLISWDAPAVTVRYYRITYGREVQKYSDT GPLYIYQEFTVPGSKSTATISGLKPGVDYTITVYAVTGSGESPASSTP ISINYRTEIDKPSQHHHHHH |
| 41 | ADX_6727_B09 CD loop | GREVQKYSDTGPLYIYQE |
| 53 | ADX_6727_B09 FG loop | VTGSGESPASSTP |
| 93 | ADX_6727_H02 (I43S) core | EVVAATPTSLLISWDAPAVTVRYYRITYGREVQKYSDLGPLYSYQEFT VPGSKSTATISGLKPGVDYTITVYAVTGSGESPASSKPISINYRT |
| 94 | ADX_6727_H02 | MGVSDVPRDLEVVAATPTSLLISWDAPAVTVRYYRITYGREVQKYSDL GPLYSYQEFTVPGSKSTATISGLKPGVDYTITVYAVTGSGESPASSKP ISINYRTEIDKPSQHHHHHH |
| 85 | ADX_6727_H02 CD loop | GREVQKYSDLGPLYSYQE |
| 95 | ADX_6727_G05 (I43S/K85A) core | EVVAATPTSLLISWDAPAVTVRYYRITYGREVQKYSDLGPLYSYQEFT VPGSKSTATISGLKPGVDYTITVYAVTGSGESPASSAPISINYRT |
| 96 | ADX_6727_G05 | MGVSDVPRDLEVVAATPTSLLISWDAPAVTVRYYRITYGREVQKYSDL GPLYSYQEFTVPGSKSTATISGLKPGVDYTITVYAVTGSGESPASSAP ISINYRTEIDKPSQHHHHHH |
| 85 | ADX_6727_G05 CD loop | GREVQKYSDLGPLYSYQE |
| 50 | ADX_6727_G05 FG loop | VTGSGESPASSAP |
| 97 | ADX_6727_G06 (Y35A/K85S) core | EVVAATPTSLLISWDAPAVTVRYYRITYGREVQKASDLGPLYIYQEFT VPGSKSTATISGLKPGVDYTITVYAVTGSGESPASSSPISINYRT |
| 98 | ADX_6727_G06 | MGVSDVPRDLEVVAATPTSLLISWDAPAVTVRYYRITYGREVQKASDL GPLYIYQEFTVPGSKSTATISGLKPGVDYTITVYAVTGSGESPASSSP ISINYRTEIDKPSQHHHHHH |
| 99 | ADX_6727_G06 CD loop | GREVQKASDLGPLYIYQE |
| 56 | ADX_6727_G06 FG loop | VTGSGESPASSSP |
| 100 | ADX_6727_F10 (Y35A/K85T) core | EVVAATPTSLLISWDAPAVTVRYYRITYGREVQKASDLGPLYIYQEFT VPGSKSTATISGLKPGVDYTITVYAVTGSGESPASSTPISINYRT |

TABLE 7-continued

SUMMARY OF SEQUENCES

| SEQ ID | Description | Sequence |
|---|---|---|
| 101 | ADX_6727_F10 | MGVSDVPRDLEVVAATPTSLLISWDAPAVTVRYYRITY<u>GREVQKASDL GPLYIYQE</u>FTVPGSKSTATISGLKPGVDYTITVYA<u>VTGSGESPASSTP</u> ISINYRTEIDKPSQHHHHHH |
| 99 | ADX_6727_F10 CD loop | GREVQKASDLGPLYIYQE |
| 53 | ADX_6727_F10 FG loop | VTGSGESPASSTP |
| 102 | ADX_6727_A07 (Y44S/K85T) core | EVVAATPTSLLISWDAPAVTVRYYRITY<u>GREVQKYSDLGPLYISQE</u>FT VPGSKSTATISGLKPGVDYTITVYA<u>VTGSGESPASSTP</u>ISINYRT |
| 103 | ADX_6727_A07 | MGVSDVPRDLEVVAATPTSLLISWDAPAVTVRYYRITY<u>GREVQKYSDL GPLYISQE</u>FTVPGSKSTATISGLKPGVDYTITVYA<u>VTGSGESPASSTP</u> ISINYRTEIDKPSQHHHHHH |
| 35 | ADX_6727_A07 CD loop | GREVQKYSDLGPLYISQE |
| 53 | ADX_6727_A07 FG loop | VTGSGESPASSTP |
| 104 | ADX_6727_F07 (Y44S/K85A) core | EVVAATPTSLLISWDAPAVTVRYYRITY<u>GREVQKYSDLGPLYISQE</u>FT VPGSKSTATISGLKPGVDYTITVYA<u>VTGSGESPASSAP</u>ISINYRT |
| 105 | ADX_6727_F07 | MGVSDVPRDLEVVAATPTSLLISWDAPAVTVRYYRITY<u>GREVQKYSDL GPLYISQE</u>FTVPGSKSTATISGLKPGVDYTITVYA<u>VTGSGESPASSAP</u> ISINYRTEIDKPSQHHHHHH |
| 35 | ADX_6727_F07 CD loop | GREVQKYSDLGPLYISQE |
| 50 | ADX_6727_F07 FG loop | VTGSGESPASSAP |
| 106 | ADX_6727_G04 (Y44S/K85S) core | EVVAATPTSLLISWDAPAVTVRYYRITY<u>GREVQKYSDLGPLYISQE</u>FT VPGSKSTATISGLKPGVDYTITVYA<u>VTGSGESPASSSP</u>ISINYRT |
| 107 | ADX_6727_G04 | MGVSDVPRDLEVVAATPTSLLISWDAPAVTVRYYRITY<u>GREVQKYSDL GPLYISQE</u>FTVPGSKSTATISGLKPGVDYTITVYA<u>VTGSGESPASSSP</u> ISINYRTEIDKPSQHHHHHH |
| 35 | ADX_6727_G04 CD loop | GREVQKYSDLGPLYISQE |
| 56 | ADX_6727_G04 FG loop | VTGSGESPASSSP |
| 108 | ADX_6727_D03 (L41S) core | EVVAATPTSLLISWDAPAVTVRYYRITY<u>GREVQKYSDLGPSYIYQE</u>FT VPGSKSTATISGLKPGVDYTITVYA<u>VTGSGESPASSKP</u>ISINYRT |
| 109 | ADX_6727_D03 | MGVSDVPRDLEVVAATPTSLLISWDAPAVTVRYYRITY<u>GREVQKYSDL GPSYIYQE</u>FTVPGSKSTATISGLKPGVDYTITVYA<u>VTGSGESPASSKP</u> ISINYRTEIDKPSQHHHHHH |

TABLE 7-continued

SUMMARY OF SEQUENCES

| SEQ ID | Description | Sequence |
|---|---|---|
| 110 | ADX_6727_D03 CD loop | GREVQKYSDLGPSYIYQE |
| 111 | ADX_6727_H10 (L41S/K85S) core | EVVAATPTSLLISWDAPAVTVRYYRITYGREVQKYSDLGPSYIYQEFT VPGSKSTATISGLKPGVDYTITVYAVTGSGESPASSSPISINYRT |
| 112 | ADX_6727_H10 | MGVSDVPRDLEVVAATPTSLLISWDAPAVTVRYYRITYGREVQKYSDL GPSYIYQEFTVPGSKSTATISGLKPGVDYTITVYAVTGSGESPASSSP ISINYRTEIDKPSQHHHHHH |
| 110 | ADX_6727_H10 CD loop | GREVQKYSDLGPSYIYQE |
| 56 | ADX_6727_H10 FG loop | VTGSGESPASSSP |
| 113 | ADX_6727_H08 (L38I/K85T) core | EVVAATPTSLLISWDAPAVTVRYYRITYGREVQKYSDTGPLYIYQEFT VPGSKSTATISGLKPGVDYTITVYAVTGSGESPASSTPISINYRT |
| 114 | ADX_6727_H08 | MGVSDVPRDLEVVAATPTSLLISWDAPAVTVRYYRITYGREVQKYSDT GPLYIYQEFTVPGSKSTATISGLKPGVDYTITVYAVTGSGESPASSTP ISINYRTEIDKPSQHHHHHH |
| 41 | ADX_6727_H08 CD loop | GREVQKYSDTGPLYIYQE |
| 53 | ADX_6727_H08 FG loop | VTGSGESPASSTP |
| 115 | ADX_6727_H06 (Y44Q/K95I) core | EVVAATPTSLLISWDAPAVTVRYYRITYGREVQKYSDLGPLYIQQEFT VPGSKSTATISGLKPGVDYTITVYAVTGSGESPASSTPISINYRT |
| 116 | ADX_6727_H06 | MGVSDVPRDLEVVAATPTSLLISWDAPAVTVRYYRITYGREVQKYSDL GPLYIQQEFTVPGSKSTATISGLKPGVDYTITVYAVTGSGESPASSTP ISINYRTEIDKPSQHHHHHH |
| 47 | ADX_6727_H06 CD loop | GREVQKYSDLGPLYIQQE |
| 53 | ADX_6727_H06 FG loop | VTGSGESPASSTP |
| 117 | ADX_6734_A02 (I43A/Y44E) core | EVVAATPTSLLISWDAPAVTVRYYRITYGREVQKYSDLGPLYAEQEFT VPGSKSTATISGLKPGVDYTITVYAVTGSGESPASSKPISINYRT |
| 118 | ADX_6734_A02 | MGVSDVPRDLEVVAATPTSLLISWDAPAVTVRYYRITYGREVQKYSDL GPLYAEQEFTVPGSKSTATISGLKPGVDYTITVYAVTGSGESPASSKP ISINYRTEIDKPSQHHHHHH |
| 119 | ADX_6734_A02 CD loop | GREVQKYSDLGPLYAEQE |
| 120 | Linker | PSTPPTPSPSTPPTPSPS |
| 121 | Linker | GSGSGSGSGSGSGS |
| 122 | Linker | GGSGSGSGSGSGS |

TABLE 7-continued

SUMMARY OF SEQUENCES

| SEQ ID | Description | Sequence |
|---|---|---|
| 123 | Linker | GGSGSGSGSGSGSGSG |
| 124 | Linker | GSEGSEGSEGSEGSE |
| 125 | Linker | GGSEGGSE |
| 126 | Linker | GSGSGSGS |
| 127 | Linker | GGGGSGGGGSGGGGSGGGGSGGGGSGGGGSGGGGS |
| 128 | Linker | GGGGSGGGGSGGGGSGGGGSGGGGS |
| 129 | Linker | GGGGSGGGGSGGGGSG |
| 130 | Linker | GPGPGPG |
| 131 | Linker | GPGPGPGPGPG |
| 132 | Linker | PAPAPA |
| 133 | Linker | PAPAPAPAPA |
| 134 | Linker | PAPAPAPAPAPAPAPA |
| 135 | Linker | PSPEPPTPEP |
| 136 | Linker | PSPEPPTPEPPSPEPPTPEP |
| 137 | Linker | PSPEPPTPEPPSPEPPTPEPPSPEPPTPEP |
| 138 | Linker | PSPEPPTPEPPSPEPPTPEPPSPEPPTPEPPSPEPPTPEP |
| 139 | Linker | EEEEDE |
| 140 | Linker | EEEEDEEEEDE |
| 141 | Linker | EEEEDEEEEDEEEEDEEEEDE |
| 142 | Linker | EEEEDEEEEDEEEEDEEEEDEEEEDEEEEDE |
| 143 | Linker | RGGEEKKKEKEKEEQEERETKTP |
| 144 | Linker | (PSPEPPTPEP)$_n$ n = 1 - 10 |
| 145 | Linker | (EEEEDE)$_n$E n = 1 - 10 |
| 146 | Exemplary use of linker | NYRTPGPSPEPPTPEP |
| 147 | Exemplary use of linker | PSPEPPTPEPGVSDV |
| 148 | C-terminal tail | EIEPKSS |
| 149 | C-terminal tail | EIDKPC |
| 150 | C-terminal tail | EIDKP |
| 151 | C-terminal tail | EIDKPS |
| 152 | C-terminal tail | EIDKPSQLE |
| 153 | C-terminal tail | EIEDEDEDED |
| 154 | C-terminal tail | EGSGS |
| 155 | C-terminal tail | EIDKPCQLE |
| 156 | C-terminal tail | EIDKPSQHHHHHH |
| 157 | C-terminal tail | GSGCHHHHHH |
| 158 | C-terminal tail | EGSGCHHHHHH |
| 159 | C-terminal tail | PIDK |

TABLE 7-continued

SUMMARY OF SEQUENCES

| SEQ ID | Description | Sequence |
|---|---|---|
| 160 | C-terminal tail | PIEK |
| 161 | C-terminal tail | PIDKP |
| 162 | C-terminal tail | PIEKP |
| 163 | C-terminal tail | PIDKPS |
| 164 | C-terminal tail | PIEKPS |
| 165 | C-terminal tail | PIDKPC |
| 166 | C-terminal tail | PIEKPC |
| 167 | C-terminal tail | PIDKPSQ |
| 168 | C-terminal tail | PIEKPSQ |
| 169 | C-terminal tail | PIDKPCQ |
| 170 | C-terminal tail | PIEKPCQ |
| 171 | C-terminal tail | PHHHHHH |
| 172 | C-terminal tail | PCHHHHHH |
| 173 | 7016_A01 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGCAGGGAGGTTCAGAAGTACTCGGACTTG GGTCCGTTGTACATCTACCAAGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A polypeptide comprising a fibronectin type III tenth ($^{10}$Fn3) domain, wherein the $^{10}$Fn3 domain binds to human serum albumin (HSA) with a $K_D$ of 1 μM or less and comprises AB, BC, CD, DE, EF, and FG loops, wherein the CD loop has 1 amino acid substitution relative to the CD loop of a $^{10}$Fn3 domain comprising the amino acid sequence set forth in SEQ ID NO: 23, and wherein the substitution is selected from the group consisting of:
  (i) the arginine (R) at position 2 of the CD loop (SEQ ID NO: 28) is substituted with an amino acid selected from D, E, A, Q, or N;
  (ii) the glutamine (Q) at position 5 of the CD loop (SEQ ID NO: 28) is substituted with D;
  (iii) the tyrosine (Y) at position 7 of the CD loop (SEQ ID NO: 28) is substituted with an amino acid selected from S or A;
  (iv) the leucine (L) at position 10 of the CD loop (SEQ ID NO: 28) is substituted with an amino acid selected from S, T, or A;
  (v) the leucine (L) at position 13 of the CD loop (SEQ ID NO: 28) is substituted with an amino acid selected from D, S, or A;
  (vi) the tyrosine (Y) at position 14 of the CD loop (SEQ ID NO: 28) is substituted with an amino acid selected from A or T;
  (vii) the isoleucine (I) at position 15 of the CD loop (SEQ ID NO: 28) is substituted with an amino acid selected from D, S, or A; and
  (viii) the tyrosine (Y) at position 16 of the CD loop (SEQ ID NO: 28) is substituted with an amino acid selected from Q, E, S, or A.

2. The polypeptide of claim 1, wherein the tyrosine (Y) at position 16 of the CD loop (SEQ ID NO: 28) is substituted with serine (S).

3. The polypeptide of claim 1, wherein the leucine (L) at position 10 of the CD loop (SEQ ID NO: 28) is substituted with threonine (T).

4. The polypeptide of claim 1, wherein the tyrosine (Y) at position 16 of the CD loop (SEQ ID NO: 28) is substituted with glutamine (Q).

5. The polypeptide of claim 1, wherein the FG loop has 1 amino acid substitution relative to the FG loop of the $^{10}$Fn3 domain comprising the amino acid sequence set forth in SEQ ID NO: 23, wherein the lysine (K) at position 12 of the FG loop (SEQ ID NO: 29) is substituted with an amino acid selected from A, T, or S.

6. The polypeptide of claim 1, wherein the polypeptide comprises an amino acid sequence at least 90% identical to the non-CD loop regions of SEQ ID NOs: 30-34, 36-40, 42-46, 48, 49, 51, 52, 54, 55, 57, 58, 60, 61, 62, 63, 65-68, 70, 71, 73-76, 78, 79, 81-84, 86, 87, 89-98, 100-109, and 111-118.

7. The polypeptide of claim 1, wherein the $^{10}$Fn3 domain binds to domain I-II of HSA.

8. The polypeptide of claim 1, wherein the polypeptide comprises a heterologous protein.

9. A composition comprising the polypeptide of claim 1, and a carrier.

10. A method of producing a polypeptide comprising a fibronectin type III tenth ($^{10}$Fn3) domain that binds to human serum albumin, the method comprising culturing a cell comprising a nucleic acid which encodes the polypeptide of claim 1 under conditions suitable for expressing the polypeptide, and purifying the polypeptide.

11. A method of enhancing the half-life of a moiety, comprising linking to the moiety a human serum albumin binding polypeptide of claim 1.

* * * * *